United States Patent
Frelinger et al.

(10) Patent No.: US 8,734,774 B2
(45) Date of Patent: May 27, 2014

(54) PROTEASE ACTIVATED CYTOKINES

(75) Inventors: John G. Frelinger, Pittsford, NY (US); John Puskas, Lutz, FL (US); Baek Kim, Rochester, NY (US); Mark Sullivan, Fairpoint, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/639,006

(22) PCT Filed: Mar. 31, 2011

(86) PCT No.: PCT/US2011/030787
§ 371 (c)(1),
(2), (4) Date: Nov. 13, 2012

(87) PCT Pub. No.: WO2011/123683
PCT Pub. Date: Oct. 6, 2011

(65) Prior Publication Data
US 2013/0089516 A1   Apr. 11, 2013

Related U.S. Application Data

(60) Provisional application No. 61/320,360, filed on Apr. 2, 2010.

(51) Int. Cl.
*A61K 38/19* (2006.01)
*A61K 38/20* (2006.01)

(52) U.S. Cl.
USPC .......................... 424/85.1; 424/85.2; 514/1.1

(58) Field of Classification Search
USPC .................................. 424/85.1, 85.2; 514/1.1
See application file for complete search history.

(56) References Cited

U.S. PATENT DOCUMENTS

| | | |
|---|---|---|
| 6,670,147 B1 | 12/2003 | Heidtmann et al. |
| 2002/0151478 A1 | 10/2002 | Chernajovsky et al. |
| 2004/0033511 A1 | 2/2004 | Pfizenmaier et al. |
| 2004/0259768 A1 | 12/2004 | Lauermann |
| 2005/0214762 A1 | 9/2005 | Ross et al. |
| 2006/0205926 A1 | 9/2006 | Ross et al. |

FOREIGN PATENT DOCUMENTS

| | | |
|---|---|---|
| WO | 2009/103965 A1 | 8/2009 |
| WO | 2010/020766 A2 | 2/2010 |

OTHER PUBLICATIONS

International Search Report from PCT/US2011/030787, mailed Dec. 26, 2011.
International Preliminary Report on Patentability from PCT/US2011/030787, mailed Oct. 11, 2012.
Stephen D Gilles et al: "Improved 1-15 circulating half-life and efficacy of an antibody-interleukin 2 immunocytokine based on reduced intracellular proteolysis" , Clinical Cancer Research, The American Association for Cancer Research, US, 8(1): 210-216 (2002).
G. Helguera et al: "Antibody-Cytokine Fusion Proteins: Harnessing the Combined Power of Cytokines and Antibodies for Cancer Therapy", Clinical Immunology, 105(3): 233-246 (2002).
Penichet M L et al: "Antibody-IL-2 fusion 1-15 proteins: a novel strategy for immune protection", Human Antibodies 8(3): 106-118 (1997).
John Puskas et al: "Development of an attenuated interleukin-2 fusion protein that can be activated by tumour-expressed proteases", Immunology, 133(2): 206-220 (2011).
EP Extended Search Report for EP Appl. No. 11763460.0, mailed Aug. 7, 2013.
Adams G, Vessillier S, Dreja H, Chernajovsky Y. Targeting cytokines to inflammation sites. Nat Biotechnol 21(11):1314-20 (2003).
Addison CL, Braciak T, Ralston R, Muller WJ, Gauldie J, Graham FL. Intratumoral injection of an adenovirus expressing interleukin 2 induces regression and immunity in a murine breast cancer model. Proc Natl Acad Sci USA 92(18):8522-6 (1995).
Allione A, Consalvo M, Nanni P, et al. Immunizing and curative potential of replicating and nonreplicating murine mammary adenocarcinoma cells engineered with interleukin (IL)-2, IL-4, IL-6, IL-7, IL-10, tumor necrosis factor alpha, graulocyte macrophage colony-stimulating factor, and gamma-interferon gen or admixed with conventional adjuvants. Cancer Res 54(23):6022-6 (1994).
Bachmann MF, Oxenius A. Interleukin 2: from immunostimulation to immunoregulation and back again. EMBO Rep 8(12):1142-8 (2007).
Balk, SP, Ko YJ, Bubley GJ. Biology of prostate-specific antigen. J Clin Oncol 21(2):383-91 (2003).
Becker JC, Varki N, Gillies SD, Furukawa K, Reisfeld RA. Long-lived and transferable tumor immunity in mice after targeted interleukin-2 therapy. J Clin Invest 98(12):2801-4 (1996).
Bergers G, Brekken R, McMahon G, et al. Matrix metalloproteinase-9 triggers the angiogenic switch during carcinogenesis. Nat Cell Biol 2(10):737-44 (2000).
Bersofsky JA, Terabe M. Oh S., Belyakov IM, Ahlers JD, Janik JE, Morris J. Progress on new vaccine strategies for the immunotherapy and prevention of cancer. J Clin Invest 113(11):1515-25 (2004).
Boon T., Coulie PG, Van den Eynde JB, van der Bruggen P., Human T cell responses against melanoma. Annu Rev Immunol 24: 175-208 (2006).
Bremer C, Tung CH, Weissleder R. In vivo molecular target assessment of matrix metalloproteinase inhibition. Nat Med 7(6): 743-8 (2001).
Chambers AF, Matrisian LM. Changing views of the role of matrix metalloproteinases in metastasis. J Natl Cancer Inst 89(17):1260-70 (1997).
Chen EI, Kridel SJ, Howard EW, Li W, Godzik A, Smith JW. A unique substrate recognition profile for matrix metalloproteinase-2. J Biol Chem 277(6):4485-91 (2002).

(Continued)

*Primary Examiner* — Prema Mertz
(74) *Attorney, Agent, or Firm* — Kilpatrick Townsend & Stockton, LLP

(57) ABSTRACT

Provided herein are chimeric nucleic acid sequences encoding chimeric polypeptides. Also provided herein are chimeric polypeptides. Further provided herein are methods of treating a subject with or at risk of developing a cancer. The methods comprise selecting a subject with or at risk of developing a cancer, and administering to the subject an effective amount of the chimeric polypeptides provided herein.

6 Claims, 21 Drawing Sheets

(56) References Cited

OTHER PUBLICATIONS

Figure 1A:
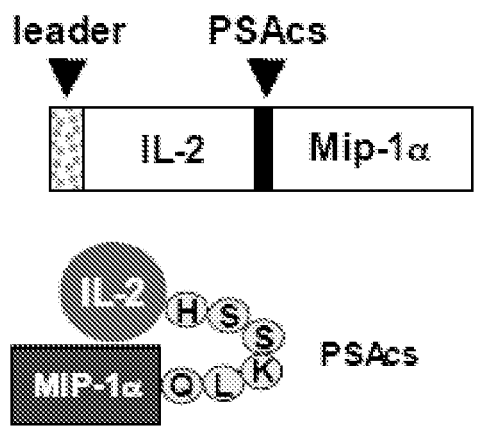

Curiel TJ. Regulatory T cells and treatment of cancer. Curr Opin Immunol 20(2):241-6 (2008).

Dela Cruz JS, Huang TH, Penichet ML, Morrison SL. Antibody-cytokine fusion proteins: innovative weapons in the war against cancer. Clin Exp Med 4(2):57-64 (2004).

Denmeade SR, Lou W, Lovgren J, Malm J, Lilja H, Isaacs JT. Specific and efficient peptide substrates for assaying the proteolytic activity of prostate-specific antigen. Cancer Res 57(21):4924-30 (1997).

Den Otter W. Jacobs JJ, Battermann JJ, et al. Local therapy of cancer with free IL-2. Cancer Immunol Immunother 57(7):931-50 (2008).

Dranoff G, Jaffee E, Lazenby A, et al. Vaccination with irradiated tumor cells engineered to secrete murine granulocyte-macrophage colony-stimulating factor stimulates potent, specific, and long-lasting anti-tumor immunity. Proc Natl Acad Sci USA 90(8):3539-43 (1993).

Egeblad M, Web Z. New functions for the matrix metalloproteinases in cancer progression. Nat Rev Cancer 2(3):161-74 (2002).

Egilmez NK, Jong YS, Sabel MS, Jacob JS, Mathiowitz E, Bankert RB. In situ tumor vaccination with interleukin-12-encapsulated biodegradable microspheres induction of tumor regression and potent antitumor immunity. Cancer Res 60(14):3832-7 (2000).

Finn OJ. Cancer Immunology, N. Engl J. Med 358(25):2704-15 (2008).

Fisher TL, Nocera M, Willis RA, et al. Generation of monoclonal antibodies specific for human kallidrein 2 (hK2) using hK2-expressing tumors. Prostate 51(3):153-65 (2002).

Gabrilovich DI, Nagaraj S. Myeloid-derived suppressor cells as regulators of the immune system. Nat Rev Immunol 9(3):162-74 (2009).

Gansbacher B, Zier K, Daniels B, Cronin K, Bannerji R, Gilboa E. Interleukin 2 gene transfer into tumor cells abrogates tumorigenicity and induces protective immunity. J Exp Med 172(4):1217-24 (1990).

Gerber SA, Rybalko VY, Bigelow CE, Lugade AA, Foster TH, JG, Lord EM, Preferential attachment of peritoneal tumor metastases to omental immune aggregates and possible role of a unique vascular microenvironment in metastatic survival and growth. Am J Pathol 169(5):1739-52 (2006).

Haidaris CG, Malone J, Sherrill LA, Bliss JM, Gaspari AA, Insel RA, Sullivan MA. Recombinant human antibody single chain variable fragments reactive with *Candida albicans* surface antigens. J Immunol Methods 257(1-2):185-202 (2001).

Hanes J, Sills A, Zhao Z, et al. Controlled local delivery of interleukin-2 by biodegradable polymers protects animals from experimental brain tumors and liver tumors. Pharm Res 18(7):899-906 (2001).

Heaney ML, Golde DW. Soluble cytokine receptors. Blood 87(3):847-57 (1996).

Hofmann UB, Westphal JR, Van Muijen GN, Ruiter DJ. Matrix metalloproteinases in human melanoma. J Invest Dermatol 115(3):337-44 (2000).

Kantoff PW, Higano CS, Shore ND, et al. Sipuleucel-T immunotherapy for castration-resistant prostate cancer. N Engl J Med 363(5):411-22 (2010).

Krist LF, Kerremans M, Broekhuis-Fluitsma DM, Eestermans IL, Meyer S, Beelen RH. Milky spots in the greater omentum are predominant sites of local tumour cell proliferation and accumulation in the peritoneal cavity. Cancer Immunol Immunother 47(4):205-12 (1998).

Lee PP, Yee C, Savage PA, et al. Characterization of circulating T cells specific for tumor-associated antigens in melanoma patients. Nat Med 5(6):677-85 (1999).

Lilja H. Biology of prostate-specific antigen. Urology 62(5 Suppl 1):27-33 (2003).

Longo DL. New therapies for castration-resistant prostate cancer. N Engl J Med 363(5):479-81 (2010).

Lord EM, Burkhardt G. Assessment of in situ host immunity to syngeneic tumors utilizing the multicellular spheroid model. Cell Immunol 85(2):340-50 (1984).

Malek TR. The biology of interleukin-2. Annu Rev Immunol 26:453-79 (2008).

Malone J, Sullivan MA. Analysis of antibody selection by phage display utilizing anti-phenobarbital antibodies. J Mol Recognit 9(5-6):738-45 (1996).

McAdam AJ, Pulaski BA, Harkins SS, Hutter EK, Lord EM, Frelinger JG. Synergistic effects of co-expression of the TH1 cytokines IL-2 and IFN-gamma on generation of murine tumor-reactive cytotoxic cells. Int J Cancer 61(5):628-34 (1995).

McAdam AJ, Pulaski BA, Storozynsky E, Yeh KY, Sickel JZ, Frelinger JG, Lord EM. Analysis of the effect of cytokines (interleeukins 2, 3, 4, and 6, granulocyte-monocyte colony-stimulating factor, and interferon-gamma) on generation of primary cytotoxic T lymphocytes against a weekly immunogenic tumor. Cell Immunol 165(2):183-92 (1995).

McKarney I. Sipuleucel-T (Provenge): active cellular immunotherapy for advanced prostate cancer. Issues Emerg Health Technol 101:1-4 (2007).

Mehlin C, Boni E, Buckner FS, et al. Heterologous expression of proteins from *Plasmodium falciparum*: results from 1000 genes. Mol Biochem Parasitol 148(2):144-60 (2006).

Minami Y, Kono T, Miyazaki T, Taniguchi T. The IL-2 receptor complex: its structure, function, and target genes. Annu Rev Immunol 11:245-68 (1993).

Morgan RA, Dudley ME, Wunderlich JR, et al. Cancer regression in patients after transfer of genetically engineered lymphocytes. Science 314(5796):126-9 (2006).

Mosmann T. Rapid colorimetric assay for cellular growth and survival: application to proliferation and cytotoxicity assays. J Immunol Methods 65(1-2):55-63 (1983).

Nikkola J, Vihinen P, Vuoristo MS, Kellokumpu-Lehtinen P, Kahari VM, Pyrhonen S. High serum levels of matrix metalloproteinase-9 and matrix metalloproteinase-1 are associated with rapid progression in patients with metastatic melanoma. Clin Cancer Res 11(14):5158-66 (2005).

Oosterling SJ, van der Bij GJ, Bogels M, van der Sijp JR, Bellen RH, Meijer S, van Egmond M. Insufficient ability of omental milky spots to prevent peritoneal tumor outgrowth supports omentectomy in minimal residual disease. Cancer Immunol Immunother 55(9):1043-51 (2006).

Ostrand-Rosenberg S., Sinha P. Myeloid-derived suppressor cells: linking inflammation and cancer. J Immunol 182(8):4499-506 (2009).

Pardoll DM. Paracrine cytokine adjuvants in cancer immunotherapy. Annu Rev Immunol 13:399-415 (1995).

Parmiani G., De Filippo A, Novellino L., Castelli C. Unique human tumor antigens: immunobiology and use in clinical trials, J. Immunol 178 (4):1975-9 (2007).

Porgador A, Gansbacher B, Bannerji R, Tzehoval E, Gilboa E, Feldman M, Eisenbach L. Anti-metastatic vaccination of tumor-bearing mice with IL-2-gene-inserted tumor cells. Int J Cancer 53(3):471-7 (1993).

Rabinovich GA, Gabrilovich D, Sotomayor EM. Immunosuppressive strategies that are mediated by tumor cells. Annu Rev Immunol 25:267-96 (2007).

Rose RC, Bonnez W, Strike DG, Reichman RC. Expression of the full-length products of the human papillomavirus type 6b (HPV-6b) and HPC-11 L2 open reading frames by recombinant baculovirus, and antigenic comparisons with HPV-11 whole virus particles. J Gen Virol 71 (Pt 11):2725-9 (1990).

Rose RC, Bonnez W, Da Rin C, McCance DJ, Reichman RC. Serological differentiation of human papillomavirus types 11, 16 and 18 using recombinant virus-like particles. J Gen Virol 75(Pt 9):2445-9 (1994).

Rosenberg, SA. Progress in human tumour immunology and immunotherapy. Nature 411(6835):380-4 (2001).

Rosenberg SA, Restifo NP, Yang JC, Morgan RA, Dudley ME, Adoptive cell transfer: a clinical path to effective cancer immunotherapy. Nat Rev Cancer 8(4):299-308 (2008).

Rosenberg SA, Yang JC, Topalian SL, et al. Treatment of 283 consecutive patients with metastatic melanoma or renal cell cancer using high-dose bolus interleukin 2. Jama 271(12):907-13 (1994).

Roth C, Mir LM, Cressent M, Quintin-Colonna F, Ley V, Fradelizi D, Kourilsky P. Inhibition of tumor growth by histoincompatible cells expressing interleukin-2. Int Immunol 4(12):1429-36 (1992).

(56) References Cited

OTHER PUBLICATIONS

Sabel MA, Arora A, Su G, Mathiowitz E, Reineke JJ, Chang AE. Synergestic effect of intratumoral IL-12 and TNF-alpha microspheres: systemic anti-tumor immunity is mediated by both CD8+ CTL and NK cells. Surgery 142(5):749-60 (2007).
Sangro B, Mazzolini G, Ruiz J, et al. Phase I trial of intratumoral injection of an adenovirus encoding interleukin-12 for advanced digestive tumors. J Clin Oncol 22(8):1389-97 (2004).
Schrama D, Reisfeld RA, Becker JC. Antibody targeted drugs as cancer therapeutics. Nat Rev Drug Discov 5(2):147-59 (2006).
Schroder FH, Roach M, 3$^{rd}$, Scardino P. Clinical decisions. Management of prostate cancer. N Engl J Med 359(24):2605-9 (2008).
Shimotsuma M, Shields JW, Simpson-Morgan MW, Sakuyama A, Shirasu M, Hagiwara A, Takahashi T. Morpho-physiological function and role of omental milky spots as omentum-associated lymphoid tissue (OALT) in the peritoneal cavity. Lymphology 26(2):90-101 (1993).
Slingluff CL, Jr., Chianese-Bullock KA, Bullock TN, et al., Immunity to melanoma antigens: from self-tolerance to immunotherapy. Adv Immunol 90:243-95 (2006).
Smith KA. The structure of IL2 bound to the three chains of the IL2 receptor and how signaling occurs. Med Immunol 5:3 (2006).
Sorensen EW, Gerber SA, Sedlacek AL, RybalkoVY, Chan WM, Lord EM. Omental immune aggregates and tumor metastasis within the peritoneal cavity. Immunol Res 45: 185-194 (2009).
Trinchieri G. Interleukin-12 and the regulation of innate resistance and adaptive immunity. Nat Rev Immunol 3(2):133-46 (2003).
Trinh R, Gurbaxani B, Morrison SL, Seyfzadeh M. Optimization of codon pair use within the (GGGGS)3 linker sequence results in enhanced protein expression. Mol Immunol 40(10):717-22 (2004).
Triozzi PL, Allen KO, Carlisle RR, Craig M, LoBuglio AF, Conry RM. Phase I study of the intratumoral administration of recombinant canarypox viruses expressing B7.1 and interleukin 12 in patients with metastatic melanoma. Clin Cancer Res 11(11):4168-75 (2005).
Turner MJ, Abdul-Alim CS, Willis RA, Risher TL, Lord EM, Frelinger JG. T-cell antigen discovery (T-CAD) assay: a novel technique for identifying T cell epitopes. J Immunol Methods 256(1-2):107-19 (2001).
van Deventer HW, Serody JS, McKinnon KP, Clements C, Brickey WJ, Ting JP. Transfection of macrophage inflammatory protein 1 alpha into B16F10 melanoma cells inhibits growth of pulmonary metastases but not subcutaneous tumors. J Immunol 169(3):1634-9 (2002).
Vlad AM, Budiu RA, Lenzner DE, et al. A phase II trial of intraperitoneal interleukin-2 in patients with platinum-resistant or platinum-refractory ovarian cancer. Cancer Immunol Immunother 59(2): 293-301 (2010)—.
Wei C, Willis RA, Tilton BR, Looney RJ, Lord EM, Barth RK, Frelinger JG. Tissue-specific expression of the human prostate-specific antigen gene in transgenic mice: implications for tolerance and immunotherapy. Proc Natl Acad Sci USA 94(12):6369-74 (1997).
Woods ML, McAdam AJ, Frelinger JG, Lord EM. Isolation and expansion of tumor-infiltrating lymphocytes. Biotechniques 15(6):970-2 (1993).
Yee C, Savage PA, Lee PP, Davis MM, Greenberg PD. Isolation of high avidity melanoma-reactive CTL from heterogeneous populations using peptide-MHC tetramers. J Immunol 162(4):2227-34 (1999).
Young FM, Phungtamdet W, Sanderson BJ. Modification of MTT assay conditions to examine the cytotoxic effects of amitraz on the human lymphoblastoid cell line, WIL2NS. Toxicol In Vitro 19(8):1051-9 (2005)—.
Zou W. Immunosuppressive networks in the tumour environment and their therapeutic relevance. Nat Rev Cancer 5(4):263-74 (2005).

SEQUENCE LISTING

<160> NUMBER OF SEQ ID NOS: 68

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

His Ser Ser Lys Leu Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Gly Pro Leu Gly Val Arg Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Ile Pro Val Ser Leu Arg Ser Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Val Pro Leu Ser Leu Tyr Ser Gly
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Ser Gly Glu Ser Pro Ala Tyr Tyr Thr Ala
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Gly Gly Gly Gly Ser

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Gly Ser Gly Ser Gly Ser
1               5

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

Gly Ser Gly Gly Gly Ser Gly Gly Gly Ser Gly Gly Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Gly Gly Gly Gly Ser Gly Gly Gly Gly Ser
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Synthetic Construct

<400> SEQUENCE: 10

Gly Gly Gly Gly Ser Gly Gly Gly Gly Ser Gly Gly Gly Gly Ser Gly
1               5                   10                  15

Gly Gly Gly Ser
            20

<210> SEQ ID NO 11
<211> LENGTH: 1236
<212> TYPE: DNA
<213> ORGANISM: Artificial Sequence
<220> FEATURE:
<223> OTHER INFORMATION: Synthetic Construct

<400> SEQUENCE: 11
gtcgacatgt acagcatgca gctcgcatcc tgtgtcacat tgacacttgt gctccttgtc      60
aacagcgcac ccacttcaag ctccacttca agctctacag cggaagcaca gcagcagcag     120
cagcagcagc agcagcagca gcagcacctg gagcagctgt tgatggacct acaggagctc     180
ctgagcagga tggagaatta caggaacctg aaactcccca ggatgctcac cttcaaattt     240
tacttgccca gcaggccaca agaattgaaa gatcttcagt gcctagaaga tgaacttgga     300
cctctgcggc atgttctgga tttgactcaa agcaaaagct ttcaattgga agatgctgag     360
aatttcatca gcaatatcag agtaactgtt gtaaaactaa agggctctga caacacattt     420

```
gagtgccaat tcgatgatga gtcagcaact gtggtggact ttctgaggag atggatagcc      480
ttctgtcaaa gcatcatctc aacaagccct caacacagca gcaagctgca ggaattcggt      540
ggcggtggct ctggtggcgg tggctctggt accgaactgt gtctgtatga cccacccgag      600
gtccccaatg ccacattcaa agccctctcc tacaagaacg caccatcct aaactgtgaa       660 tgcaagagag gtttccgaag actaaaggaa ttggtctata tgcgttgctt aggaaactcc      720
tggagcagca actgccagtg caccagcaac tcccatgaca aatcgagaaa gcaagttaca      780
gctcaacttg aacaccagaa agagcaacaa accacaacag acatgcagaa gccaacacag      840
tctatgcacc aagagaacct tacaggtcac tgcagggagc cacctccttg gaacatgaa       900 gattccaaga gaatctatca tttcgtggaa ggacagagtg ttcactacga gtgtattccg      960
ggatacaagg ctctacagag aggtcctgct attagcatct gcaagatgaa gtgtgggaaa     1020
acggggtgga ctcagcccca gctcacatgt gtagatgaaa gagaacacca ccgatttctg     1080
gctagtgagg aatctcaagg aagcagaaat tcttctcccg agagtgagac ttcctgcccc     1140
ataaccacca cagacttccc acaacccaca gaaacaactg caatgacgga gacatttgtg     1200
ctcacaatgg agtataaggt agcataatga ggatcc                               1236

<210> SEQ ID NO 12
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 12
gtcgacatgt acagcatgca gctcgcatcc tgtgtcacat tgacacttgt gctccttgtc       60
aacagcgcac ccacttcaag ctccacttca agctctacag cggaagcaca gcagcagcag      120
cagcagcagc agcagcagca gcagcacctg gagcagctgt tgatggacct acaggagctc      180
ctgagcagga tggagaatta caggaacctg aaactcccca ggatgctcac cttcaaattt      240
tacttgccca gcaggccac agaattgaaa gatcttcagt gcctagaaga tgaacttgga       300
cctctgcggc atgttctgga tttgactcaa agcaaaagct ttcaattgga gatgctgag       360 aatttcatca gcaatatcag agtaactgtt gtaaaactaa agggctctga caacacattt      420
gagtgccaat tcgatgatga gtcagcaact gtggtggact ttctgaggag atggatagcc      480
ttctgtcaaa gcatcatctc aacaagccct caacacagca gcaagctgca ggaattcggt      540
ggcggtggct ctggtggcgg tggctctggt accgaactgt gtctgtatga cccacccgag      600
gtccccaatg ccacattcaa agccctctcc tacaagaacg caccatcct aaactgtgaa       660 tgcaagagag gtttccgaag actaaaggaa ttggtctata tgcgttgctt aggaaactcc      720
tggagcagca actgccagtg caccagcaac tcccatgaca aatcgagaaa gcaagttaca      780
gctcaacttg aacaccagaa agagcaacaa accacaacag acatgcagaa gccaacacag      840
tctatgcacc aagagaacct tacaggtcac tgcagggagc cacctccttg gaacatgaa       900 gattccaaga gaatctatca tttcgtggaa ggacagagtg ttcactacga gtgtattccg      960
ggatacaagg ctctacagag aggtcctgct attagcatct gcaagatgaa gtgtgggaaa     1020
acggggtgga ctcagcccca gctcacatgt gtagatgaaa gagaacacca ccgatttctg     1080
gctagtgagg aatctcaagg aagcagaaat tcttctcccg agagtgagac ttcctgcccc     1140
ataaccacca cagacttccc acaacccaca gaaacaactg caatgacgga gacatttgtg     1200
ctcacaatgg agtataaggt agcacaccac caccaccacc actaatgagg atcc           1254
```

<210> SEQ ID NO 13
<211> LENGTH: 1266
<212> TYPE: DNA
<213> ORGANISM: Artificial Sequence
<220> FEATURE:
<223> OTHER INFORMATION: Synthetic Construct

<400> SEQUENCE: 13

```
gtcgacatgt acagcatgca gctcgcatcc tgtgtcacat tgacacttgt gctccttgtc      60
aacagcgcac ccacttcaag ctccacttca agctctacag cggaagcaca gcagcagcag     120
cagcagcagc agcagcagca gcagcacctg gagcagctgt tgatggacct acaggagctc     180
ctgagcagga tggagaatta caggaacctg aaactcccca ggatgctcac cttcaaattt     240
tacttgccca agcaggccac agaattgaaa gatcttcagt gcctagaaga tgaacttgga     300
cctctgcggc atgttctgga tttgactcaa agcaaaagct ttcaattgga agatgctgag     360
aatttcatca gcaatatcag agtaactgtt gtaaaactaa agggctctga acacacattt     420
gagtgccaat tcgatgatga gtcagcaact gtggtggact ttctgaggag atggatagcc     480
ttctgtcaaa gcatcatctc aacaagccct caacacagca gcaagctgca ggaattcggt     540
ggcggtggct ctggtggcgg tggctctggt ggcggtggct ctggtggcgg tggctctggt     600
accgaactgt gtctgtatga cccacccgag gtccccaatg ccacattcaa gcccctctcc     660
tacaagaacg gcaccatcct aaactgtgaa tgcaagagag gtttccgaag actaaaggaa     720
ttggtctata tgcgttgctt aggaaactcc tggagcagca actgccagtg caccagcaac     780
tcccatgaca aatcgagaaa gcaagttaca gctcaacttg aacaccagaa agagcaacaa     840
accacaacag acatgcagaa gccaacacag tctatgcacc aagagaacct acaggtcac     900
tgcagggagc cacctccttg ggaacatgaa gattccaaga gaatctatca tttcgtggaa     960
ggacagagtg ttcactacga gtgtattccg ggatacaagg ctctacagag aggtcctgct    1020
attagcatct gcaagatgaa gtgtgggaaa acggggtgga ctcagcccca gctcacatgt    1080
gtagatgaaa gagaacacca ccgatttctg gctagtgagg aatctcaagg aagcagaaat    1140
tcttctcccg agagtgagac ttcctgcccc ataaccacca cagacttccc acaacccaca    1200
gaaacaactg caatgacgga gacatttgtg ctcacaatgg agtataaggt agcataatga    1260
ggatcc                                                              1266
```

<210> SEQ ID NO 14
<211> LENGTH: 1284
<212> TYPE: DNA
<213> ORGANISM: Artificial Sequence
<220> FEATURE:
<223> OTHER INFORMATION: Synthetic Construct

<400> SEQUENCE: 14

```
gtcgacatgt acagcatgca gctcgcatcc tgtgtcacat tgacacttgt gctccttgtc      60
aacagcgcac ccacttcaag ctccacttca agctctacag cggaagcaca gcagcagcag     120
cagcagcagc agcagcagca gcagcacctg gagcagctgt tgatggacct acaggagctc     180
ctgagcagga tggagaatta caggaacctg aaactcccca ggatgctcac cttcaaattt     240
tacttgccca agcaggccac agaattgaaa gatcttcagt gcctagaaga tgaacttgga     300
cctctgcggc atgttctgga tttgactcaa agcaaaagct ttcaattgga agatgctgag     360
aatttcatca gcaatatcag agtaactgtt gtaaaactaa agggctctga acacacattt     420
gagtgccaat tcgatgatga gtcagcaact gtggtggact ttctgaggag atggatagcc     480
```

```
ttctgtcaaa gcatcatctc aacaagccct caacacagca gcaagctgca ggaattcggt    540
ggcggtggct ctggtggcgg tggctctggt ggcggtggct ctggtggcgg tggctctggt    600
accgaactgt gtctgtatga cccacccgag gtccccaatg ccacattcaa agccctctcc    660
tacaagaacg gcaccatcct aaactgtgaa tgcaagagag gtttccgaag actaaaggaa    720
ttggtctata tgcgttgctt aggaaactcc tggagcagca actgccagtg caccagcaac    780
tcccatgaca aatcgagaaa gcaagttaca gctcaacttg aacaccagaa agagcaacaa    840
accacaacag acatgcagaa gccaacacag tctatgcacc aagagaacct acaggtcac     900 tgcagggagc cacctccttg ggaacatgaa gattccaaga gaatctatca tttcgtggaa    960
ggacagagtg ttcactacga gtgtattccg ggatacaagg ctctacagag aggtcctgct   1020
attagcatct gcaagatgaa gtgtgggaaa acggggtgga ctcagcccca gctcacatgt   1080
gtagatgaaa gagaacacca ccgatttctg gctagtgagg aatctcaagg aagcagaaat   1140
tcttctcccg agagtgagac ttcctgcccc ataaccacca cagacttccc acaacccaca   1200
gaaacaactg caatgacgga gacatttgtg ctcacaatgg agtataaggt agcacaccac   1260
caccaccacc actaatgagg atcc                                           1284
```

<210> SEQ ID NO 15
<211> LENGTH: 1287
<212> TYPE: DNA
<213> ORGANISM: Artificial Sequence
<220> FEATURE:
<223> OTHER INFORMATION: Synthetic Construct

<400> SEQUENCE: 15

```
gtcgacatgt acagcatgca gctcgcatcc tgtgtcacat tgacacttgt gctccttgtc     60
aacagcgcac ccacttcaag ctccacttca agctctacag cggaagcaca gcagcagcag    120
cagcagcagc agcagcagca gcagcacctg gagcagctgt tgatggacct acaggagctc    180
ctgagcagga tggagaatta caggaacctg aaactcccca ggatgctcac cttcaaattt    240
tacttgccca gcaggccacc agaattgaaa gatcttcagt gcctagaaga tgaacttgga    300
cctctgcggc atgttctgga tttgactcaa agcaaaagct ttcaattgga agatgctgag    360
aatttcatca gcaatatcag agtaactgtt gtaaaactaa agggctctga caacacattt    420
gagtgccaat tcgatgatga gtcagcaact gtggtggact ttctgaggag atggatagcc    480
ttctgtcaaa gcatcatctc aacaagccct caaggtcctc tgggtgtcag aggtgaattc    540
ggtggcggtg gctctggtgg cggtggctct ggtggcggtg gctctggtgg cggtggctct    600
ggtaccgaac tgtgtctgta tgacccaccc gaggtcccca tgccacatt caaagccctc    660 tcctacaaga acggcaccat cctaaactgt gaatgcaaga gaggtttccg aagactaaag    720
gaattggtct atatgcgttg cttaggaaac tcctggagca gcaactgcca gtgcaccagc    780
aactcccatg acaaatcgag aaagcaagtt acagctcaac ttgaacacca gaaagagcaa    840
caaaccacaa cagacatgca gaagccaaca cagtctatgc accaagagaa ccttacaggt    900
cactgcaggg agccacctcc ttgggaacat gaagattcca agagaatcta tcatttcgtg    960
gaaggacaga gtgttcacta cgagtgtatt ccgggataca aggctctaca gagaggtcct   1020
gctattagca tctgcaagat gaagtgtggg aaaacggggt ggactcagcc ccagctcaca   1080
tgtgtagatg aaagagaaca ccaccgattt ctggctagtg aggaatctca aggaagcaga   1140
aattcttctc ccgagagtga gacttcctgc cccataacca ccacagactt cccacaaccc   1200
acagaaacaa ctgcaatgac ggagacattt gtgctcacaa tggagtataa ggtagcacac   1260
```

```
caccaccacc accactaatg aggatcc                                        1287
```

<210> SEQ ID NO 16
<211> LENGTH: 1290
<212> TYPE: DNA
<213> ORGANISM: Artificial Sequence
<220> FEATURE:
<223> OTHER INFORMATION: Synthetic Construct

<400> SEQUENCE: 16

```
gtcgacatgt acagcatgca gctcgcatcc tgtgtcacat tgacacttgt gctccttgtc     60
aacagcgcac ccacttcaag ctccacttca agctctacag cggaagcaca gcagcagcag    120
cagcagcagc agcagcagca gcagcacctg gagcagctgt tgatggacct acaggagctc    180
ctgagcagga tggagaatta caggaacctg aaactcccca ggatgctcac cttcaaattt    240
tacttgccca gcaggccac agaattgaaa gatcttcagt gcctagaaga tgaacttgga     300
cctctgcggc atgttctgga tttgactcaa agcaaaagct ttcaattgga agatgctgag    360
aatttcatca gcaatatcag agtaactgtt gtaaaactaa agggctctga caacacattt    420
gagtgccaat tcgatgatga gtcagcaact gtggtggact ttctgaggag atggatagcc    480
ttctgtcaaa gcatcatctc aacaagccct caaatccctg tcagcctgag aagcggtgaa    540
ttcggtggcg gtggctctgg tggcggtggc tctggtggcg gtggctctgg tggcggtggc    600
tctggtaccg aactgtgtct gtatgaccca cccgaggtcc ccaatgccac attcaaagcc    660
ctctcctaca gaacggcac catcctaaac tgtgaatgca agagaggttt ccgaagacta    720
aaggaattgg tctatatgcg ttgcttagga aactcctgga gcagcaactg ccagtgcacc    780
agcaactccc atgacaaatc gagaaagcaa gttacagctc aacttgaaca ccagaaagag    840
caacaaacca aacagacat gcagaagcca acacagtcta tgcaccaaga gaaccttaca    900
ggtcactgca gggagccacc tcctgggaa catgaagatt ccaagagaat ctatcatttc    960
gtggaaggac agagtgttca ctacgagtgt attccgggat acaaggctct acagagaggt   1020
cctgctatta gcatctgcaa gatgaagtgt gggaaaacgg ggtggactca gcccagctc    1080
acatgtgtag atgaaagaga acaccaccga tttctggcta gtgaggaatc tcaaggaagc   1140
agaaattctt ctcccgagag tgagacttcc tgccccataa ccaccacaga cttcccacaa   1200
cccacagaaa caactgcaat gacggagaca tttgtgctca caatggagta taggtagca    1260
caccaccacc accaccacta atgaggatcc                                    1290
```

<210> SEQ ID NO 17
<211> LENGTH: 1290
<212> TYPE: DNA
<213> ORGANISM: Artificial Sequence
<220> FEATURE:
<223> OTHER INFORMATION: Synthetic Construct

<400> SEQUENCE: 17

```
gtcgacatgt acagcatgca gctcgcatcc tgtgtcacat tgacacttgt gctccttgtc     60
aacagcgcac ccacttcaag ctccacttca agctctacag cggaagcaca gcagcagcag    120
cagcagcagc agcagcagca gcagcacctg gagcagctgt tgatggacct acaggagctc    180
ctgagcagga tggagaatta caggaacctg aaactcccca ggatgctcac cttcaaattt    240
tacttgccca gcaggccac agaattgaaa gatcttcagt gcctagaaga tgaacttgga     300
cctctgcggc atgttctgga tttgactcaa agcaaaagct ttcaattgga agatgctgag    360
aatttcatca gcaatatcag agtaactgtt gtaaaactaa agggctctga caacacattt    420
```

```
gagtgccaat tcgatgatga gtcagcaact gtggtggact ttctgaggag atggatagcc    480
ttctgtcaaa gcatcatctc aacaagccct caagtccctc tgagcctgta cagcggtgaa    540
ttcggtggcg gtggctctgg tggcggtggc tctggtggcg gtggctctgg tggcggtggc    600
tctggtaccg aactgtgtct gtatgaccca cccgaggtcc ccaatgccac attcaaagcc    660
ctctcctaca gaacggcac catcctaaac tgtgaatgca agagaggttt ccgaagacta    720
aaggaattgg tctatatgcg ttgcttagga aactcctgga gcagcaactg ccagtgcacc    780
agcaactccc atgacaaatc gagaaagcaa gttacagctc aacttgaaca ccagaaagag    840
caacaaacca caacagacat gcagaagcca acacagtcta tgcaccaaga gaaccttaca    900
ggtcactgca gggagccacc tccttgggaa catgaagatt ccaagagaat ctatcatttc    960
gtggaaggac agagtgttca ctacgagtgt attccgggat acaaggctct acagagaggt   1020
cctgctatta gcatctgcaa gatgaagtgt gggaaaacgg ggtggactca gccccagctc   1080
acatgtgtag atgaaagaga acaccaccga tttctggcta gtgaggaatc tcaaggaagc   1140
agaaattctt ctcccgagag tgagacttcc tgccccataa ccaccacaga cttcccacaa   1200
cccacagaaa caactgcaat gacgagacta tttgtgctca aatggagta taaggtagca   1260
caccaccacc accaccacta atgaggatcc                                    1290
```

<210> SEQ ID NO 18
<211> LENGTH: 1296
<212> TYPE: DNA
<213> ORGANISM: Artificial Sequence
<220> FEATURE:
<223> OTHER INFORMATION: Synthetic Construct

<400> SEQUENCE: 18

```
gtcgacatgt acagcatgca gctcgcatcc tgtgtcacat tgacacttgt gctccttgtc     60
aacagcgcac ccacttcaag ctccacttca agctctacag cggaagcaca gcagcagcag    120
cagcagcagc agcagcagca gcagcacctg gagcagctgt tgatggacct acaggagctc    180
ctgagcagga tggagaatta caggaacctg aaactcccca ggatgctcac cttcaaattt    240
tacttgccca gcaggccac agaattgaaa gatcttcagt gcctagaaga tgaacttgga    300
cctctgcggc atgttctgga tttgactcaa agcaaaagct ttcaattgga agatgctgag    360
aatttcatca gcaatatcag agtaactgtt gtaaaactaa agggctctga caacacattt    420
gagtgccaat tcgatgatga gtcagcaact gtggtggact ttctgaggag atggatagcc    480
ttctgtcaaa gcatcatctc aacaagccct caaagcggtg aaagccctgc ttactacacc    540
gctgaattcg gtggcggtgg ctctggtggc ggtggctctg gtggcggtgg ctctggtggc    600
ggtggctctg gtaccgaact gtgtctgtat gacccacccg aggtccccaa tgccacattc    660
aaagccctct cctacaagaa cggcaccatc ctaaactgtg aatgcaagag aggtttccga    720
agactaaagg aattggtcta tatgcgttgc ttaggaaact cctggagcag caactgccag    780
tgcaccagca actcccatga caaatcgaga aagcaagtta cagctcaact tgaacaccag    840
aaagagcaac aaaccacaac agacatgcag aagccaacac agtctatgca ccaagagaac    900
cttacaggtc actgcaggga gccacctcct tgggaacatg aagattccaa gagaatctat    960
catttcgtgg aaggacagag tgttcactac gagtgtattc cgggatacaa ggctctacag   1020
agaggtcctg ctattagcat ctgcaagatg aagtgtggga aaacggggtg gactcagccc   1080
cagctcacat gtgtagatga aagagaacac caccgatttc tggctagtga ggaatctcaa   1140
ggaagcagaa attcttctcc cgagagtgag acttcctgcc ccataaccac cacagacttc   1200
```

```
ccacaaccca cagaaacaac tgcaatgacg gagacatttg tgctcacaat ggagtataag    1260
gtagcacacc accaccacca ccactaatga ggatcc                              1296

<210> SEQ ID NO 19
<211> LENGTH: 1278
<212> TYPE: DNA
<213> ORGANISM: Artificial Sequence
<220> FEATURE:
<223> OTHER INFORMATION: Synthetic Construct

<400> SEQUENCE: 19
gtcgacatgt acaggatgca actcctgtct tgcattgcac taagtcttgc acttgtcaca      60
aacagtgcac ctacttcaag ttctacaaag aaaacacagc tacaactgga gcatttactt    120
ctggatttac agatgatttt gaatggaatt aataattaca agaatcccaa actcaccagg    180
atgctcacat ttaagtttta catgcccaag aaggccacag aactgaaaca tcttcagtgt    240
ctagaagaag aactcaaacc tctggaggaa gtgctaaatt tagctcaaag caaaaacttt    300
cacttaagac ccagggactt aatcagcaat atcaacgtaa tagttctgga actaaaggga    360
tctgaaacaa cattcatgtg tgaatatgct gatgagacag caaccattgt agaatttctg    420
aacagatgga ttaccttttg tcaaagcatc atctcaacac tgactcacag cagcaagctg    480
caggaattcg tgtgcggtgg ctctggtggc ggtggctctg gtaccagtc tgtgctgact    540 cagccaccct cagtgtctgg ggccccagga cagagggtca ccatctcctg cactgggacc    600
agctccaaca tcggggcaca ttatgatgta cattggtatc agcagtttcc aggaacagcc    660
cccaagcgcc tcatttatgg taacaataat cggccctcag gggtccctgc ccgattctct    720
ggctccaagt ctggcacctc agcctccctg gccatcactg gctccaggc tgaggatgag    780 gctgattatt actgccagtc ctatgacagg agcctgcgtg gttgggtgtt cggcggaggg    840
accaagctga ccgtcctagg tgagggtaaa tcttccggat ctggttccga atccaaagct    900
agcgaggtgc agctggtgga gtctggggga ggcttggtac agcctggcag gtccctgaga    960
ctctcctgtg cagcctctgg attcaccttt gatgattatg ccatgcactg ggtccggcaa   1020
gctccaggga agggcctgga gtgggtctca ggtattagtt ggaatagtgg tagcataggc   1080
tatgcggact ctgtgaaggg ccgattcacc atctccagag acaattccaa gaacacgctg   1140
tatctgcaaa tgaacagcct gagagccgag gacacggccg tatattactg tgcgaaagac   1200
gttaactgga actacggcta ctactttgac tactggggcc agggcaccct ggtcaccgtc   1260
tcctcataat gaggatcc                                                 1278

<210> SEQ ID NO 20
<211> LENGTH: 1296
<212> TYPE: DNA
<213> ORGANISM: Artificial Sequence
<220> FEATURE:
<223> OTHER INFORMATION: Synthetic Construct

<400> SEQUENCE: 20
gtcgacatgt acaggatgca actcctgtct tgcattgcac taagtcttgc acttgtcaca      60
aacagtgcac ctacttcaag ttctacaaag aaaacacagc tacaactgga gcatttactt    120
ctggatttac agatgatttt gaatggaatt aataattaca agaatcccaa actcaccagg    180
atgctcacat ttaagtttta catgcccaag aaggccacag aactgaaaca tcttcagtgt    240
ctagaagaag aactcaaacc tctggaggaa gtgctaaatt tagctcaaag caaaaacttt    300
cacttaagac ccagggactt aatcagcaat atcaacgtaa tagttctgga actaaaggga    360
```

```
tctgaaacaa cattcatgtg tgaatatgct gatgagacag caaccattgt agaatttctg      420
aacagatgga ttacctttg tcaaagcatc atctcaacac tgactcacag cagcaagctg       480
caggaattcg gtggcggtgg ctctggtggc ggtggctctg gtacccagtc tgtgctgact      540
cagccaccct cagtgtctgg ggccccagga cagagggtca ccatctcctg cactgggacc     600
agctccaaca tcggggcaca ttatgatgta cattggtatc agcagtttcc aggaacagcc      660
cccaagcgcc tcatttatgg taacaataat cggccctcag gggtccctgc ccgattctct      720
ggctccaagt ctggcacctc agcctccctg gccatcactg gctccaggc tgaggatgag       780 gctgattatt actgccagtc ctatgacagg agcctgcgtg ttgggtgtt cggcggaggg       840 accaagctga ccgtcctagg tgagggtaaa tcttccggat ctggttccga atccaaagct      900
agcgaggtgc agctggtgga gtctggggga ggcttggtac agcctggcag gtccctgaga      960
ctctcctgtg cagcctctgg attcaccttt gatgattatg ccatgcactg ggtccggcaa     1020
gctccaggga agggcctgga gtgggtctca ggtattagtt ggaatagtgg tagcataggc     1080
tatgcggact ctgtgaaggg ccgattcacc atctccagag acaattccaa gaacacgctg     1140
tatctgcaaa tgaacagcct gagagccgag gacacggccg tatattactg tgcgaaagac     1200
gttaactgga actacggcta ctactttgac tactggggcc agggcaccct ggtcaccgtc     1260
tcctcacacc accaccacca ccactaatga ggatcc                              1296
```

<210> SEQ ID NO 21
<211> LENGTH: 1293
<212> TYPE: DNA
<213> ORGANISM: Artificial Sequence
<220> FEATURE:
<223> OTHER INFORMATION: Synthetic Construct

<400> SEQUENCE: 21

```
gtcgacatgt acaggatgca actcctgtct tgcattgcac taagtcttgc acttgtcaca       60
aacagtgcac ctacttcaag ttctacaaag aaaacacagc tacaactgga gcatttactt      120
ctggatttac agatgatttt gaatggaatt aataattaca agaatcccaa actcaccagg      180
atgctcacat ttaagttta catgcccaag aaggccacag aactgaaaca tcttcagtgt       240
ctagaagaag aactcaaacc tctggaggaa gtgctaaatt tagctcaaag caaaaacttt      300
cacttaagac ccagggactt aatcagcaat atcaacgtaa tagttctgga actaaaggga     360
tctgaaacaa cattcatgtg tgaatatgct gatgagacag caaccattgt agaatttctg      420
aacagatgga ttacctttg tcaaagcatc atctcaacac tgactcacag cagcaagctg       480
caggaattcg gtggcggtgg ctctggtggc ggtggctctg gtggcggtgg ctctggtacc     540
cagtctgtgc tgactcagcc accctcagtg tctggggccc caggacagag ggtcaccatc     600
tcctgcactg ggaccagctc caacatcggg gcacattatg atgtacattg gtatcagcag     660
tttccaggaa cagccccaa gcgcctcatt tatggtaaca ataatcggcc ctcagggtc      720 cctgcccgat ctctggctc caagtctggc acctcagcct ccctggccat cactggctc      780 caggctgagg atgaggctga ttattactgc cagtcctatg acaggagcct gcgtggttgg     840
gtgttcggcg agggaccaa gctgaccgtc ctaggtgagg gtaaatcttc cggatctggt      900
tccgaatcca aagctagcga ggtgcagctg gtggagtctg ggggaggctt ggtacagcct     960
ggcaggtccc tgagactctc ctgtgcagcc tctggattca cctttgatga ttatgccatg    1020
cactgggtcc ggcaagctcc agggaagggc ctggagtggg tctcaggtat tagttggaat    1080
agtggtagca taggctatgc ggactctgtg aagggccgat tcaccatctc cagagacaat    1140
```

```
tccaagaaca cgctgtatct gcaaatgaac agcctgagag ccgaggacac ggccgtatat    1200
tactgtgcga aagacgttaa ctggaactac ggctactact ttgactactg gggccagggc    1260
accctggtca ccgtctcctc ataatgagga tcc                                 1293
```

<210> SEQ ID NO 22
<211> LENGTH: 1311
<212> TYPE: DNA
<213> ORGANISM: Artificial Sequence
<220> FEATURE:
<223> OTHER INFORMATION: Synthetic Construct

<400> SEQUENCE: 22

```
gtcgacatgt acaggatgca actcctgtct tgcattgcac taagtcttgc acttgtcaca      60
aacagtgcac ctacttcaag ttctacaaag aaaacacagc tacaactgga gcatttactt     120
ctggatttac agatgatttt gaatggaatt aataattaca agaatcccaa actcaccagg     180
atgctcacat ttaagtttta catgcccaag aaggccacag aactgaaaca tcttcagtgt     240
ctagaagaag aactcaaacc tctggaggaa gtgctaaatt tagctcaaag caaaaacttt     300
cacttaagac ccagggactt aatcagcaat atcaacgtaa tagttctgga actaaaggga     360
tctgaaacaa cattcatgtg tgaatatgct gatgagacag caaccattgt agaatttctg     420
aacagatgga ttacctttg tcaaagcatc atctcaacac tgactcacag cagcaagctg     480
caggaattcg gtggcggtgg ctctggtggc ggtggctctg gtggcggtgg ctctggtacc     540
cagtctgtgc tgactcagcc accctcagtg tctggggccc caggacagag ggtcaccatc     600
tcctgcactg gaccagctc caacatcggg gcacattatg atgtacattg gtatcagcag     660
tttccaggaa cagccccca gcgcctcatt tatggtaaca ataatcggcc ctcaggggtc     720
cctgcccgat tctctggctc caagtctggc acctcagcct ccctggccat cactgggctc     780
caggctgagg atgaggctga ttattactgc cagtcctatg acaggagcct gcgtggttgg     840
gtgttcggcg agggaccaa gctgaccgtc ctaggtgagg gtaaatcttc cggatctggt     900
tccgaatcca aagctagcga ggtgcagctg gtggagtctg ggggaggctt ggtacagcct     960
ggcaggtccc tgagactctc ctgtgcagcc tctggattca cctttgatga ttatgccatg    1020
cactgggtcc ggcaagctcc agggaagggc ctggagtggg tctcaggtat tagttggaat    1080
agtggtagca taggctatgc ggactctgtg aagggccgat tcaccatctc cagagacaat    1140
tccaagaaca cgctgtatct gcaaatgaac agcctgagag ccgaggacac ggccgtatat    1200
tactgtgcga aagacgttaa ctggaactac ggctactact ttgactactg gggccagggc    1260
accctggtca ccgtctcctc acaccaccac caccaccact aatgaggatc c             1311
```

<210> SEQ ID NO 23
<211> LENGTH: 1308
<212> TYPE: DNA
<213> ORGANISM: Artificial Sequence
<220> FEATURE:
<223> OTHER INFORMATION: Synthetic Construct

<400> SEQUENCE: 23

```
gtcgacatgt acaggatgca actcctgtct tgcattgcac taagtcttgc acttgtcaca      60
aacagtgcac ctacttcaag ttctacaaag aaaacacagc tacaactgga gcatttactt     120
ctggatttac agatgatttt gaatggaatt aataattaca agaatcccaa actcaccagg     180
atgctcacat ttaagtttta catgcccaag aaggccacag aactgaaaca tcttcagtgt     240
ctagaagaag aactcaaacc tctggaggaa gtgctaaatt tagctcaaag caaaaacttt     300
```

```
cacttaagac ccagggactt aatcagcaat atcaacgtaa tagttctgga actaaaggga       360
tctgaaacaa cattcatgtg tgaatatgct gatgagacag caaccattgt agaatttctg       420
aacagatgga ttacctttttg tcaaagcatc atctcaacac tgactcacag cagcaagctg     480
caggaattcg gtggcggtgg ctctggtggc ggtggctctg gtggcggtgg ctctggtggc       540
ggtggctctg gtacccagtc tgtgctgact cagccaccct cagtgtctgg ggccccagga       600
cagagggtca ccatctcctg cactgggacc agctccaaca tcggggcaca ttatgatgta       660
cattggtatc agcagtttcc aggaacagcc cccaagcgcc tcatttatgg taacaataat       720
cggccctcag gggtccctgc ccgattctct ggctccaagt ctggcacctc agcctccctg       780
gccatcactg gctccaggc tgaggatgag gctgattatt actgccagtc ctatgacagg       840
agcctgcgtg gttgggtgtt cggcggaggg accaagctga ccgtcctagg tgagggtaaa      900
tcttccggat ctggttccga atccaaagct agcgaggtgc agctggtgga gtctggggga     960
ggcttggtac agcctggcag gtccctgaga ctctcctgtg cagcctctgg attcaccttt       1020
gatgattatg ccatgcactg ggtccggcaa gctccaggga agggcctgga gtgggtctca      1080
ggtattagtt ggaatagtgg tagcataggc tatgcggact ctgtgaaggg ccgattcacc      1140
atctccagag acaattccaa gaacacgctg tatctgcaaa tgaacagcct gagagccgag      1200
gacacggccg tatattactg tgcgaaagac gttaactgga actacggcta ctactttgac      1260
tactggggcc agggcaccct ggtcaccgtc tcctcataat gaggatcc                   1308
```

<210> SEQ ID NO 24
<211> LENGTH: 1326
<212> TYPE: DNA
<213> ORGANISM: Artificial Sequence
<220> FEATURE:
<223> OTHER INFORMATION: Synthetic Construct

<400> SEQUENCE: 24

```
gtcgacatgt acaggatgca actcctgtct tgcattgcac taagtcttgc acttgtcaca       60
aacagtgcac ctacttcaag ttctacaaag aaaacacagc tacaactgga gcatttactt       120
ctggatttac agatgatttt gaatggaatt aataattaca agaatcccaa actcaccagg       180
atgctcacat ttaagttttta catgcccaag aaggccacag aactgaaaca tcttcagtgt     240
ctagaagaag aactcaaacc tctggaggaa gtgctaaatt tagctcaaag caaaaacttt       300
cacttaagac ccagggactt aatcagcaat atcaacgtaa tagttctgga actaaaggga       360
tctgaaacaa cattcatgtg tgaatatgct gatgagacag caaccattgt agaatttctg       420
aacagatgga ttacctttttg tcaaagcatc atctcaacac tgactcacag cagcaagctg     480
caggaattcg gtggcggtgg ctctggtggc ggtggctctg gtggcggtgg ctctggtggc       540
ggtggctctg gtacccagtc tgtgctgact cagccaccct cagtgtctgg ggccccagga       600
cagagggtca ccatctcctg cactgggacc agctccaaca tcggggcaca ttatgatgta       660
cattggtatc agcagtttcc aggaacagcc cccaagcgcc tcatttatgg taacaataat       720
cggccctcag gggtccctgc ccgattctct ggctccaagt ctggcacctc agcctccctg       780
gccatcactg gctccaggc tgaggatgag gctgattatt actgccagtc ctatgacagg       840
agcctgcgtg gttgggtgtt cggcggaggg accaagctga ccgtcctagg tgagggtaaa      900
tcttccggat ctggttccga atccaaagct agcgaggtgc agctggtgga gtctggggga     960
ggcttggtac agcctggcag gtccctgaga ctctcctgtg cagcctctgg attcaccttt       1020
gatgattatg ccatgcactg ggtccggcaa gctccaggga agggcctgga gtgggtctca      1080
```

```
ggtattagtt ggaatagtgg tagcataggc tatgcggact ctgtgaaggg ccgattcacc   1140
atctccagag acaattccaa gaacacgctg tatctgcaaa tgaacagcct gagagccgag   1200
gacacggccg tatattactg tgcgaaagac gttaactgga actacggcta ctactttgac   1260
tactggggcc agggcaccct ggtcaccgtc tcctcacacc accaccacca ccactaatga   1320
ggatcc                                                              1326
```

<210> SEQ ID NO 25
<211> LENGTH: 1194
<212> TYPE: DNA
<213> ORGANISM: Artificial Sequence
<220> FEATURE:
<223> OTHER INFORMATION: Synthetic Construct

<400> SEQUENCE: 25

```
gtcgacatgt acaggatgca actcctgtct tgcattgcac taagtcttgc acttgtcaca     60
aacagtgcac ctacttcaag ttctacaaag aaaacacagc tacaactgga gcatttactt    120
ctggatttac agatgatttt gaatggaatt aataattaca gaatcccaa actcaccagg     180 atgctcacat ttaagtttta catgcccaag aaggccacag aactgaaaca tcttcagtgt    240
ctagaagaag aactcaaacc tctggaggaa gtgctaaatt tagctcaaag caaaaacttt    300
cacttaagac ccagggactt aatcagcaat atcaacgtaa tagttctgga actaaaggga   360
tctgaaacaa cattcatgtg tgaatatgct gatgagacag caaccattgt agaatttctg    420
aacagatgga ttaccttttg tcaaagcatc atctcaacac tgactcacag cagcaagctg   480
caggaattcg gtggcggtgg ctctggtggc ggtggctctg gtaccgagct ctgtgacgat    540
gacccgccag atcccacac gccacattc aaagccatgg cctacaagga aggaaccatg    600
ttgaactgtg aatgcaagag aggtttccgc agaataaaaa gcgggtcact ctatatgctc    660
tgtacaggaa actctagcca ctcgtcctgg acaaccaat gtcaatgcac aagctctgcc    720
actcggaaca aacgaaaca agtgacacct caacctgaag aacagaaaga aggaaaaacc   780
acagaaatgc aaagtccaat gcagccagtg gaccaagcga gccttccagg tcactgcagg   840
gaacctccac catgggaaaa tgaagccaca gagagaattt atcatttcgt ggtggggcag    900
atggtttatt atcagtgcgt ccagggatac agggctctac acagaggtcc tgctgagagc    960
gtctgcaaaa tgacccacgg gaagacaagg tggacccagc cccagctcat atgcacaggt   1020
gaaatggaga ccagtcagtt tccaggtgaa gagaagcctc aggcaagccc cgaaggccgt   1080
cctgagagtg agacttcctg cctcgtcaca acaacagatt ttcaaataca gacagaaatg   1140
gctgcaacca tggagacgtc catatttaca acagagtacc agtaatgagg atcc         1194
```

<210> SEQ ID NO 26
<211> LENGTH: 1209
<212> TYPE: DNA
<213> ORGANISM: Artificial Sequence
<220> FEATURE:
<223> OTHER INFORMATION: Synthetic Construct

<400> SEQUENCE: 26

```
gtcgacatgt acaggatgca actcctgtct tgcattgcac taagtcttgc acttgtcaca     60
aacagtgcac ctacttcaag ttctacaaag aaaacacagc tacaactgga gcatttactt    120
ctggatttac agatgatttt gaatggaatt aataattaca gaatcccaa actcaccagg     180 atgctcacat ttaagtttta catgcccaag aaggccacag aactgaaaca tcttcagtgt    240
ctagaagaag aactcaaacc tctggaggaa gtgctaaatt tagctcaaag caaaaacttt    300
```

```
cacttaagac ccagggactt aatcagcaat atcaacgtaa tagttctgga actaaaggga      360
tctgaaacaa cattcatgtg tgaatatgct gatgagacag caaccattgt agaatttctg      420
aacagatgga ttaccttttg tcaaagcatc atctcaacac tgactcacag cagcaagctg      480
caggaattcg gtggcggtgg ctctggtggc ggtggctctg gtggcggtgg ctctggtacc      540
gagctctgtg acgatgaccc gccagagatc ccacacgcca cattcaaagc catggcctac      600
aaggaaggaa ccatgttgaa ctgtgaatgc aagagaggtt ccgcagaat aaaaagcggg       660 tcactctata tgctctgtac aggaaactct agccactcgt cctgggacaa ccaatgtcaa      720
tgcacaagct ctgccactcg gaacacaacg aaacaagtga cacctcaacc tgaagaacag      780
aaagaaggaa aaaccacaga aatgcaaagt ccaatgcagc cagtggacca agcgagcctt      840
ccaggtcact gcagggaacc tccaccatgg gaaaatgaag ccacagagag aatttatcat      900
ttcgtggtgg ggcagatggt ttattatcag tgcgtccagg gatacagggc tctacacaga      960
ggtcctgctg agagcgtctg caaaatgacc cacgggaaga caaggtggac ccagccccag     1020
ctcatatgca caggtgaaat ggagaccagt cagtttccag gtgaagagaa gcctcaggca     1080
agccccgaag gccgtcctga gagtgagact tcctgcctcg tcacaacaac agattttcaa     1140
atacagacag aaatggctgc aaccatggag acgtccatat ttacaacaga gtaccagtaa     1200
tgaggatcc                                                            1209
```

<210> SEQ ID NO 27
<211> LENGTH: 1227
<212> TYPE: DNA
<213> ORGANISM: Artificial Sequence
<220> FEATURE:
<223> OTHER INFORMATION: Synthetic Construct

<400> SEQUENCE: 27

```
gtcgacatgt acaggatgca actcctgtct tgcattgcac taagtcttgc acttgtcaca       60
aacagtgcac ctacttcaag ttctacaaag aaaacacagc tacaactgga gcatttactt      120
ctggatttac agatgatttt gaatggaatt aataattaca agaatcccaa actcaccagg      180
atgctcacat ttaagtttta catgcccaag aaggccacag aactgaaaca tcttcagtgt      240
ctagaagaag aactcaaacc tctggaggaa gtgctaaatt tagctcaaag caaaaacttt      300
cacttaagac ccagggactt aatcagcaat atcaacgtaa tagttctgga actaaaggga      360
tctgaaacaa cattcatgtg tgaatatgct gatgagacag caaccattgt agaatttctg      420
aacagatgga ttaccttttg tcaaagcatc atctcaacac tgactcacag cagcaagctg      480
caggaattcg gtggcggtgg ctctggtggc ggtggctctg gtggcggtgg ctctggtacc      540
gagctctgtg acgatgaccc gccagagatc ccacacgcca cattcaaagc catggcctac      600
aaggaaggaa ccatgttgaa ctgtgaatgc aagagaggtt ccgcagaat aaaaagcggg       660 tcactctata tgctctgtac aggaaactct agccactcgt cctgggacaa ccaatgtcaa      720
tgcacaagct ctgccactcg gaacacaacg aaacaagtga cacctcaacc tgaagaacag      780
aaagaaggaa aaaccacaga aatgcaaagt ccaatgcagc cagtggacca agcgagcctt      840
ccaggtcact gcagggaacc tccaccatgg gaaaatgaag ccacagagag aatttatcat      900
ttcgtggtgg ggcagatggt ttattatcag tgcgtccagg gatacagggc tctacacaga      960
ggtcctgctg agagcgtctg caaaatgacc cacgggaaga caaggtggac ccagccccag     1020
ctcatatgca caggtgaaat ggagaccagt cagtttccag gtgaagagaa gcctcaggca     1080
agccccgaag gccgtcctga gagtgagact tcctgcctcg tcacaacaac agattttcaa     1140
```

```
atacagacag aaatggctgc aaccatggag acgtccatat ttacaacaga gtaccagcac    1200
caccaccacc accactaatg aggatcc                                       1227

<210> SEQ ID NO 28
<211> LENGTH: 1215
<212> TYPE: DNA
<213> ORGANISM: Artificial Sequence
<220> FEATURE:
<223> OTHER INFORMATION: Synthetic Construct

<400> SEQUENCE: 28
gtcgacatgt acaggatgca actcctgtct tgcattgcac taagtcttgc acttgtcaca     60
aacagtgcac ctacttcaag ttctacaaag aaaacacagc tacaactgga gcatttactt    120
ctggatttac agatgatttt gaatggaatt aataattaca agaatcccaa actcaccagg    180
atgctcacat ttaagtttta catgcccaag aaggccacag aactgaaaca tcttcagtgt    240
ctagaagaag aactcaaacc tctggaggaa gtgctaaatt tagctcaaag caaaaacttt    300
cacttaagac ccagggactt aatcagcaat atcaacgtaa tagttctgga actaaaggga    360
tctgaaacaa cattcatgtg tgaatatgct gatgagacag caaccattgt agaatttctg    420
aacagatgga ttaccttttg tcaaagcatc atctcaacac tgactcacag cagcaagctg    480
caggaattcg gtggcggtgg ctctggtggc ggtggctctg gtggcggtgg ctctggtacc    540
gagctctgtg acgatgaccc gccagagatc ccacacgcca cattcaaagc catggcctac    600
aaggaaggaa ccatgttgaa ctgtgaatgc aagagaggtt ccgcagaat aaaaagcggg    660 tcactctata tgctctgtac aggaaactct agccactcgt cctgggacaa ccaatgtcaa    720
tgcacaagct ctgccactcg gaacacaacg aaacaagtga cacctcaacc tgaagaacag    780
aaagaaagga aaaccacaga aatgcaaagt ccaatgcagc cagtggacca agcgagcctt    840
ccaggtcact gcagggaacc tccaccatgg gaaaatgaag ccacagagag aatttatcat    900
ttcgtggtgg ggcagatggt ttattatcag tgcgtccagg gatacagggc tctacacaga    960
ggtcctgctg agagcgtctg caaaatgacc cacgggaaga caaggtggac ccagcccag    1020 ctcatatgca caggtgaaat ggagaccagt cagtttccag gtgaagagaa gcctcaggca    1080
agccccgaag gccgtcctga gagtgagact tcctgcctcg tcacaacaac agattttcaa    1140
atacagacag aaatggctgc aaccatggag acgtccatat ttacaacaga gtaccaggta    1200
gcataatgag gatcc                                                    1215

<210> SEQ ID NO 29
<211> LENGTH: 1233
<212> TYPE: DNA
<213> ORGANISM: Artificial Sequence
<220> FEATURE:
<223> OTHER INFORMATION: Synthetic Construct

<400> SEQUENCE: 29
gtcgacatgt acaggatgca actcctgtct tgcattgcac taagtcttgc acttgtcaca     60
aacagtgcac ctacttcaag ttctacaaag aaaacacagc tacaactgga gcatttactt    120
ctggatttac agatgatttt gaatggaatt aataattaca agaatcccaa actcaccagg    180
atgctcacat ttaagtttta catgcccaag aaggccacag aactgaaaca tcttcagtgt    240
ctagaagaag aactcaaacc tctggaggaa gtgctaaatt tagctcaaag caaaaacttt    300
cacttaagac ccagggactt aatcagcaat atcaacgtaa tagttctgga actaaaggga    360
tctgaaacaa cattcatgtg tgaatatgct gatgagacag caaccattgt agaatttctg    420
```

```
aacagatgga ttaccttttg tcaaagcatc atctcaacac tgactcacag cagcaagctg      480
caggaattcg gtggcggtgg ctctggtggc ggtggctctg gtggcggtgg ctctggtacc      540
gagctctgtg acgatgaccc gccagagatc ccacacgcca cattcaaagc catggcctac      600
aaggaaggaa ccatgttgaa ctgtgaatgc aagagaggtt tccgcagaat aaaaagcggg      660
tcactctata tgctctgtac aggaaactct agccactcgt cctgggacaa ccaatgtcaa      720
tgcacaagct ctgccactcg gaacacaacg aaacaagtga cacctcaacc tgaagaacag      780
aaagaaagga aaaccacaga aatgcaaagt ccaatgcagc cagtggacca agcgagcctt      840
ccaggtcact gcagggaacc tccaccatgg gaaaatgaag ccacagagag aatttatcat      900
ttcgtggtgg ggcagatggt ttattatcag tgcgtccagg gatacagggc tctacacaga      960
ggtcctgctg agagcgtctg caaaatgacc cacgggaaga caaggtggac ccagcccag     1020 ctcatatgca caggtgaaat ggagaccagt cagtttccag gtgaagagaa gcctcaggca     1080
agccccgaag gccgtcctga gagtgagact tcctgcctcg tcaacaacaa cagattttcaa    1140 atacagacag aaatggctgc aaccatggag acgtccatat ttacaacaga gtaccaggta     1200
gcacaccacc accaccacca ctaatgagga tcc                                  1233

<210> SEQ ID NO 30
<211> LENGTH: 1245
<212> TYPE: DNA
<213> ORGANISM: Artificial Sequence
<220> FEATURE:
<223> OTHER INFORMATION: Synthetic Construct

<400> SEQUENCE: 30
gtcgacatgt acaggatgca actcctgtct tgcattgcac taagtcttgc acttgtcaca       60
aacagtgcac ctacttcaag ttctacaaag aaaacacagc tacaactgga gcatttactt      120
ctggatttac agatgatttt gaatggaatt aataattaca gaatcccaa actcaccagg       180 atgctcacat ttaagtttta catgcccaag aaggccacag aactgaaaca tcttcagtgt      240
ctagaagaag aactcaaacc tctggaggaa gtgctaaatt tagctcaaag caaaaacttt      300
cacttaagac ccagggactt aatcagcaat atcaacgtaa tagttctgga actaaaggga     360
tctgaaacaa cattcatgtg tgaatatgct gatgagacag caaccattgt agaatttctg      420
aacagatgga ttaccttttg tcaaagcatc atctcaacac tgactcacag cagcaagctg      480
caggaattcg gtggcggtgg ctctggtggc ggtggctctg gtggcggtgg ctctggtggc      540
ggtggctctg gtggcggtgg ctctggtacc gagctctgtg acgatgaccc gccagagatc      600
ccacacgcca cattcaaagc catggcctac aaggaaggaa ccatgttgaa ctgtgaatgc      660
aagagaggtt tccgcagaat aaaaagcggg tcactctata tgctctgtac aggaaactct      720
agccactcgt cctgggacaa ccaatgtcaa tgcacaagct ctgccactcg gaacacaacg      780
aaacaagtga cacctcaacc tgaagaacag aaagaaagga aaaccacaga atgcaaagt      840 ccaatgcagc cagtggacca agcgagcctt ccaggtcact gcagggaacc tccaccatgg      900
gaaaatgaag ccacagagag aatttatcat ttcgtggtgg ggcagatggt ttattatcag      960
tgcgtccagg gatacagggc tctacacaga ggtcctgctg agagcgtctg caaaatgacc     1020
cacgggaaga caaggtggac ccagcccag ctcatatgca caggtgaaat ggagaccagt     1080
cagtttccag gtgaagagaa gcctcaggca agccccgaag gccgtcctga gagtgagact     1140
tcctgcctcg tcaacaacaa cagattttcaa atacagacag aaatggctgc aaccatggag    1200
acgtccatat ttacaacaga gtaccaggta gcataatgag gatcc                     1245
```

<210> SEQ ID NO 31
<211> LENGTH: 406
<212> TYPE: PRT
<213> ORGANISM: Artificial Sequence
<220> FEATURE:
<223> OTHER INFORMATION: Synthetic Construct

<400> SEQUENCE: 31

```
Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln His Ser Ser Lys Leu Gln Glu
                165                 170                 175

Phe Gly Gly Gly Gly Ser Gly Gly Gly Gly Ser Gly Thr Glu Leu Cys
            180                 185                 190

Leu Tyr Asp Pro Pro Glu Val Pro Asn Ala Thr Phe Lys Ala Leu Ser
        195                 200                 205

Tyr Lys Asn Gly Thr Ile Leu Asn Cys Glu Cys Lys Arg Gly Phe Arg
    210                 215                 220

Arg Leu Lys Glu Leu Val Tyr Met Arg Cys Leu Gly Asn Ser Trp Ser
225                 230                 235                 240

Ser Asn Cys Gln Cys Thr Ser Asn Ser His Asp Lys Ser Arg Lys Gln
                245                 250                 255

Val Thr Ala Gln Leu Glu His Gln Lys Glu Gln Gln Thr Thr Thr Asp
            260                 265                 270

Met Gln Lys Pro Thr Gln Ser Met His Gln Glu Asn Leu Thr Gly His
        275                 280                 285

Cys Arg Glu Pro Pro Trp Glu His Glu Asp Ser Lys Arg Ile Tyr
    290                 295                 300

His Phe Val Glu Gly Gln Ser Val His Tyr Glu Cys Ile Pro Gly Tyr
305                 310                 315                 320

Lys Ala Leu Gln Arg Gly Pro Ala Ile Ser Ile Cys Lys Met Lys Cys
                325                 330                 335

Gly Lys Thr Gly Trp Thr Gln Pro Gln Leu Thr Cys Val Asp Glu Arg
            340                 345                 350

Glu His His Arg Phe Leu Ala Ser Glu Glu Ser Gln Gly Ser Arg Asn
        355                 360                 365
```

Ser Ser Pro Glu Ser Glu Thr Ser Cys Pro Ile Thr Thr Thr Asp Phe
            370                 375                 380

Pro Gln Pro Thr Glu Thr Thr Ala Met Thr Glu Thr Phe Val Leu Thr
385                 390                 395                 400

Met Glu Tyr Lys Val Ala
            405

<210> SEQ ID NO 32
<211> LENGTH: 412
<212> TYPE: PRT
<213> ORGANISM: Artificial Sequence
<220> FEATURE:
<223> OTHER INFORMATION: Synthetic Construct

<400> SEQUENCE: 32

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
            50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
            85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln His Ser Ser Lys Leu Gln Glu
            165                 170                 175

Phe Gly Gly Gly Gly Ser Gly Gly Gly Ser Gly Thr Glu Leu Cys
            180                 185                 190

Leu Tyr Asp Pro Pro Glu Val Pro Asn Ala Thr Phe Lys Ala Leu Ser
            195                 200                 205

Tyr Lys Asn Gly Thr Ile Leu Asn Cys Glu Cys Lys Arg Gly Phe Arg
210                 215                 220

Arg Leu Lys Glu Leu Val Tyr Met Arg Cys Leu Gly Asn Ser Trp Ser
225                 230                 235                 240

Ser Asn Cys Gln Cys Thr Ser Asn Ser His Asp Lys Ser Arg Lys Gln
            245                 250                 255

Val Thr Ala Gln Leu Glu His Gln Lys Glu Gln Gln Thr Thr Thr Asp
            260                 265                 270

Met Gln Lys Pro Thr Gln Ser Met His Gln Glu Asn Leu Thr Gly His
            275                 280                 285

Cys Arg Glu Pro Pro Trp Glu His Glu Asp Ser Lys Arg Ile Tyr
            290                 295                 300

His Phe Val Glu Gly Gln Ser Val His Tyr Glu Cys Ile Pro Gly Tyr
305                 310                 315                 320

Lys Ala Leu Gln Arg Gly Pro Ala Ile Ser Ile Cys Lys Met Lys Cys

```
                    325                 330                 335
Gly Lys Thr Gly Trp Thr Gln Pro Gln Leu Thr Cys Val Asp Glu Arg
            340                 345                 350

Glu His His Arg Phe Leu Ala Ser Glu Glu Ser Gln Gly Ser Arg Asn
            355                 360                 365

Ser Ser Pro Glu Ser Glu Thr Ser Cys Pro Ile Thr Thr Asp Phe
370                 375                 380

Pro Gln Pro Thr Glu Thr Thr Ala Met Thr Glu Thr Phe Val Leu Thr
385                 390                 395                 400

Met Glu Tyr Lys Val Ala His His His His His His
            405                 410

<210> SEQ ID NO 33
<211> LENGTH: 416
<212> TYPE: PRT
<213> ORGANISM: Artificial Sequence
<220> FEATURE:
<223> OTHER INFORMATION: Synthetic Construct

<400> SEQUENCE: 33

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln His Ser Ser Lys Leu Gln Glu
                165                 170                 175

Phe Gly Gly Gly Gly Ser Gly Gly Gly Ser Gly Gly Gly Gly Ser
            180                 185                 190

Gly Gly Gly Gly Ser Gly Thr Glu Leu Cys Leu Tyr Asp Pro Pro Glu
        195                 200                 205

Val Pro Asn Ala Thr Phe Lys Ala Leu Ser Tyr Lys Asn Gly Thr Ile
210                 215                 220

Leu Asn Cys Glu Cys Lys Arg Gly Phe Arg Arg Leu Lys Glu Leu Val
225                 230                 235                 240

Tyr Met Arg Cys Leu Gly Asn Ser Trp Ser Ser Asn Cys Gln Cys Thr
                245                 250                 255

Ser Asn Ser His Asp Lys Ser Arg Lys Gln Val Thr Ala Gln Leu Glu
            260                 265                 270

His Gln Lys Glu Gln Gln Thr Thr Thr Asp Met Gln Lys Pro Thr Gln
        275                 280                 285
```

Ser Met His Gln Glu Asn Leu Thr Gly His Cys Arg Glu Pro Pro
    290                 295                 300

Trp Glu His Glu Asp Ser Lys Arg Ile Tyr His Phe Val Glu Gly Gln
305                 310                 315                 320

Ser Val His Tyr Glu Cys Ile Pro Gly Tyr Lys Ala Leu Gln Arg Gly
                325                 330                 335

Pro Ala Ile Ser Ile Cys Lys Met Lys Cys Gly Lys Thr Gly Trp Thr
            340                 345                 350

Gln Pro Gln Leu Thr Cys Val Asp Glu Arg Glu His His Arg Phe Leu
        355                 360                 365

Ala Ser Glu Glu Ser Gln Gly Ser Arg Asn Ser Ser Pro Glu Ser Glu
    370                 375                 380

Thr Ser Cys Pro Ile Thr Thr Thr Asp Phe Pro Gln Pro Thr Glu Thr
385                 390                 395                 400

Thr Ala Met Thr Glu Thr Phe Val Leu Thr Met Glu Tyr Lys Val Ala
                405                 410                 415

<210> SEQ ID NO 34
<211> LENGTH: 422
<212> TYPE: PRT
<213> ORGANISM: Artificial Sequence
<220> FEATURE:
<223> OTHER INFORMATION: Synthetic Construct

<400> SEQUENCE: 34

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln His Ser Ser Lys Leu Gln Glu
                165                 170                 175

Phe Gly Gly Gly Gly Ser Gly Gly Gly Ser Gly Gly Gly Gly Ser
            180                 185                 190

Gly Gly Gly Gly Ser Gly Thr Glu Leu Cys Leu Tyr Asp Pro Pro Glu
        195                 200                 205

Val Pro Asn Ala Thr Phe Lys Ala Leu Ser Tyr Lys Asn Gly Thr Ile
210                 215                 220

Leu Asn Cys Glu Cys Lys Arg Gly Phe Arg Arg Leu Lys Glu Leu Val
225                 230                 235                 240

```
Tyr Met Arg Cys Leu Gly Asn Ser Trp Ser Asn Cys Gln Cys Thr
                245                 250                 255

Ser Asn Ser His Asp Lys Ser Arg Lys Gln Val Thr Ala Gln Leu Glu
            260                 265                 270

His Gln Lys Glu Gln Gln Thr Thr Thr Asp Met Gln Lys Pro Thr Gln
            275                 280                 285

Ser Met His Gln Glu Asn Leu Thr Gly His Cys Arg Glu Pro Pro Pro
290                 295                 300

Trp Glu His Glu Asp Ser Lys Arg Ile Tyr His Phe Val Glu Gly Gln
305                 310                 315                 320

Ser Val His Tyr Glu Cys Ile Pro Gly Tyr Lys Ala Leu Gln Arg Gly
                325                 330                 335

Pro Ala Ile Ser Ile Cys Lys Met Lys Cys Gly Lys Thr Gly Trp Thr
                340                 345                 350

Gln Pro Gln Leu Thr Cys Val Asp Glu Arg Glu His His Arg Phe Leu
                355                 360                 365

Ala Ser Glu Glu Ser Gln Gly Ser Arg Asn Ser Ser Pro Glu Ser Glu
            370                 375                 380

Thr Ser Cys Pro Ile Thr Thr Thr Asp Phe Pro Gln Pro Thr Glu Thr
385                 390                 395                 400

Thr Ala Met Thr Glu Thr Phe Val Leu Thr Met Glu Tyr Lys Val Ala
                405                 410                 415

His His His His His His
            420

<210> SEQ ID NO 35
<211> LENGTH: 423
<212> TYPE: PRT
<213> ORGANISM: Artificial Sequence
<220> FEATURE:
<223> OTHER INFORMATION: Synthetic Construct

<400> SEQUENCE: 35

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Pro Leu Gly Val Arg Gly
                165                 170                 175

Glu Phe Gly Gly Gly Gly Ser Gly Gly Gly Gly Ser Gly Gly Gly Gly
```

```
                  180                 185                 190
Ser Gly Gly Gly Ser Gly Thr Glu Leu Cys Leu Tyr Asp Pro Pro
            195                 200                 205

Glu Val Pro Asn Ala Thr Phe Lys Ala Leu Ser Tyr Lys Asn Gly Thr
            210                 215                 220

Ile Leu Asn Cys Glu Cys Lys Arg Gly Phe Arg Arg Leu Lys Glu Leu
225                 230                 235                 240

Val Tyr Met Arg Cys Leu Gly Asn Ser Trp Ser Ser Asn Cys Gln Cys
                245                 250                 255

Thr Ser Asn Ser His Asp Lys Ser Arg Lys Gln Val Thr Ala Gln Leu
            260                 265                 270

Glu His Gln Lys Glu Gln Gln Thr Thr Thr Asp Met Gln Lys Pro Thr
            275                 280                 285

Gln Ser Met His Gln Glu Asn Leu Thr Gly His Cys Arg Glu Pro Pro
            290                 295                 300

Pro Trp Glu His Glu Asp Ser Lys Arg Ile Tyr His Phe Val Glu Gly
305                 310                 315                 320

Gln Ser Val His Tyr Glu Cys Ile Pro Gly Tyr Lys Ala Leu Gln Arg
                325                 330                 335

Gly Pro Ala Ile Ser Ile Cys Lys Met Lys Cys Gly Lys Thr Gly Trp
            340                 345                 350

Thr Gln Pro Gln Leu Thr Cys Val Asp Glu Arg Glu His His Arg Phe
            355                 360                 365

Leu Ala Ser Glu Glu Ser Gln Gly Ser Arg Asn Ser Ser Pro Glu Ser
            370                 375                 380

Glu Thr Ser Cys Pro Ile Thr Thr Thr Asp Phe Pro Gln Pro Thr Glu
385                 390                 395                 400

Thr Thr Ala Met Thr Glu Thr Phe Val Leu Thr Met Glu Tyr Lys Val
                405                 410                 415

Ala His His His His His His
            420

<210> SEQ ID NO 36
<211> LENGTH: 424
<212> TYPE: PRT
<213> ORGANISM: Artificial Sequence
<220> FEATURE:
<223> OTHER INFORMATION: Synthetic Construct

<400> SEQUENCE: 36

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
        50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125
```

Val Lys Leu Lys Gly Ser Asp Asn Thr Phe Glu Cys Gln Phe Asp Asp
            130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Ile Pro Val Ser Leu Arg Ser
                165                 170                 175

Gly Glu Phe Gly Gly Gly Gly Ser Gly Gly Gly Gly Ser Gly Gly Gly
            180                 185                 190

Gly Ser Gly Gly Gly Gly Ser Gly Thr Glu Leu Cys Leu Tyr Asp Pro
            195                 200                 205

Pro Glu Val Pro Asn Ala Thr Phe Lys Ala Leu Ser Tyr Lys Asn Gly
            210                 215                 220

Thr Ile Leu Asn Cys Glu Cys Lys Arg Gly Phe Arg Arg Leu Lys Glu
225                 230                 235                 240

Leu Val Tyr Met Arg Cys Leu Gly Asn Ser Trp Ser Ser Asn Cys Gln
                245                 250                 255

Cys Thr Ser Asn Ser His Asp Lys Ser Arg Lys Gln Val Thr Ala Gln
            260                 265                 270

Leu Glu His Gln Lys Glu Gln Gln Thr Thr Asp Met Gln Lys Pro
            275                 280                 285

Thr Gln Ser Met His Gln Glu Asn Leu Thr Gly His Cys Arg Glu Pro
            290                 295                 300

Pro Pro Trp Glu His Glu Asp Ser Lys Arg Ile Tyr His Phe Val Glu
305                 310                 315                 320

Gly Gln Ser Val His Tyr Glu Cys Ile Pro Gly Tyr Lys Ala Leu Gln
                325                 330                 335

Arg Gly Pro Ala Ile Ser Ile Cys Lys Met Lys Cys Gly Lys Thr Gly
            340                 345                 350

Trp Thr Gln Pro Gln Leu Thr Cys Val Asp Glu Arg Glu His His Arg
                355                 360                 365

Phe Leu Ala Ser Glu Glu Ser Gln Gly Ser Arg Asn Ser Ser Pro Glu
            370                 375                 380

Ser Glu Thr Ser Cys Pro Ile Thr Thr Thr Asp Phe Pro Gln Pro Thr
385                 390                 395                 400

Glu Thr Thr Ala Met Thr Glu Thr Phe Val Leu Thr Met Glu Tyr Lys
                405                 410                 415

Val Ala His His His His His His
            420

<210> SEQ ID NO 37
<211> LENGTH: 424
<212> TYPE: PRT
<213> ORGANISM: Artificial Sequence
<220> FEATURE:
<223> OTHER INFORMATION: Synthetic Construct

<400> SEQUENCE: 37

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
        50                  55                  60

Tyr Arg Asn Leu Lys Leu Pro Arg Met Leu Thr Phe Lys Phe Tyr Leu
 65                  70                  75                  80

Pro Lys Gln Ala Thr Glu Leu Lys Asp Leu Gln Cys Leu Glu Asp Glu
                 85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Val Pro Leu Ser Leu Tyr Ser
                165                 170                 175

Gly Glu Phe Gly Gly Gly Ser Gly Gly Gly Ser Gly Gly
            180                 185                 190

Gly Ser Gly Gly Gly Ser Gly Thr Glu Leu Cys Leu Tyr Asp Pro
        195                 200                 205

Pro Glu Val Pro Asn Ala Thr Phe Lys Ala Leu Ser Tyr Lys Asn Gly
210                 215                 220

Thr Ile Leu Asn Cys Glu Cys Lys Arg Gly Phe Arg Arg Leu Lys Glu
225                 230                 235                 240

Leu Val Tyr Met Arg Cys Leu Gly Asn Ser Trp Ser Asn Cys Gln
                245                 250                 255

Cys Thr Ser Asn Ser His Asp Lys Ser Arg Lys Gln Val Thr Ala Gln
                260                 265                 270

Leu Glu His Gln Lys Glu Gln Gln Thr Thr Thr Asp Met Gln Lys Pro
            275                 280                 285

Thr Gln Ser Met His Gln Glu Asn Leu Thr Gly His Cys Arg Glu Pro
        290                 295                 300

Pro Pro Trp Glu His Glu Asp Ser Lys Arg Ile Tyr His Phe Val Glu
305                 310                 315                 320

Gly Gln Ser Val His Tyr Glu Cys Ile Pro Gly Tyr Lys Ala Leu Gln
                325                 330                 335

Arg Gly Pro Ala Ile Ser Ile Cys Lys Met Lys Cys Gly Lys Thr Gly
                340                 345                 350

Trp Thr Gln Pro Gln Leu Thr Cys Val Asp Glu Arg Glu His His Arg
            355                 360                 365

Phe Leu Ala Ser Glu Glu Ser Gln Gly Ser Arg Asn Ser Ser Pro Glu
        370                 375                 380

Ser Glu Thr Ser Cys Pro Ile Thr Thr Thr Asp Phe Pro Gln Pro Thr
385                 390                 395                 400

Glu Thr Thr Ala Met Thr Glu Thr Phe Val Leu Thr Met Glu Tyr Lys
                405                 410                 415

Val Ala His His His His His His
            420

<210> SEQ ID NO 38
<211> LENGTH: 426
<212> TYPE: PRT
<213> ORGANISM: Artificial Sequence
<220> FEATURE:
<223> OTHER INFORMATION: Synthetic Construct

<400> SEQUENCE: 38

Met Tyr Ser Met Gln Leu Ala Ser Cys Val Thr Leu Thr Leu Val Leu

-continued

```
1               5               10              15
Leu Val Asn Ser Ala Pro Thr Ser Ser Thr Ser Ser Ser Thr Ala
            20              25              30
Glu Ala Gln Gln Gln Gln Gln Gln Gln Gln Gln Gln Gln His Leu
            35              40              45
Glu Gln Leu Leu Met Asp Leu Gln Glu Leu Leu Ser Arg Met Glu Asn
        50              55              60
Tyr Arg Asn Leu Lys Leu Pro Arg Met Leu Thr Phe Lys Phe Tyr Leu
65              70              75              80
Pro Lys Gln Ala Thr Glu Leu Lys Asp Leu Gln Cys Leu Glu Asp Glu
            85              90              95
Leu Gly Pro Leu Arg His Val Leu Asp Leu Thr Gln Ser Lys Ser Phe
            100             105             110
Gln Leu Glu Asp Ala Glu Asn Phe Ile Ser Asn Ile Arg Val Thr Val
            115             120             125
Val Lys Leu Lys Gly Ser Asp Asn Thr Phe Glu Cys Gln Phe Asp Asp
            130             135             140
Glu Ser Ala Thr Val Val Asp Phe Leu Arg Arg Trp Ile Ala Phe Cys
145             150             155             160
Gln Ser Ile Ile Ser Thr Ser Pro Gln Ser Gly Glu Ser Pro Ala Tyr
            165             170             175
Tyr Thr Ala Glu Phe Gly Gly Gly Ser Gly Gly Gly Ser Gly
            180             185             190
Gly Gly Gly Ser Gly Gly Gly Ser Gly Thr Glu Leu Cys Leu Tyr
            195             200             205
Asp Pro Pro Glu Val Pro Asn Ala Thr Phe Lys Ala Leu Ser Tyr Lys
            210             215             220
Asn Gly Thr Ile Leu Asn Cys Glu Cys Lys Arg Gly Phe Arg Arg Leu
225             230             235             240
Lys Glu Leu Val Tyr Met Arg Cys Leu Gly Asn Ser Trp Ser Ser Asn
            245             250             255
Cys Gln Cys Thr Ser Asn Ser His Asp Lys Ser Arg Lys Gln Val Thr
            260             265             270
Ala Gln Leu Glu His Gln Lys Glu Gln Gln Thr Thr Thr Asp Met Gln
            275             280             285
Lys Pro Thr Gln Ser Met His Gln Glu Asn Leu Thr Gly His Cys Arg
            290             295             300
Glu Pro Pro Pro Trp Glu His Glu Asp Ser Lys Arg Ile Tyr His Phe
305             310             315             320
Val Glu Gly Gln Ser Val His Tyr Glu Cys Ile Pro Gly Tyr Lys Ala
            325             330             335
Leu Gln Arg Gly Pro Ala Ile Ser Ile Cys Lys Met Lys Cys Gly Lys
            340             345             350
Thr Gly Trp Thr Gln Pro Gln Leu Thr Cys Val Asp Glu Arg Glu His
            355             360             365
His Arg Phe Leu Ala Ser Glu Glu Ser Gln Gly Ser Arg Asn Ser Ser
            370             375             380
Pro Glu Ser Glu Thr Ser Cys Pro Ile Thr Thr Thr Asp Phe Pro Gln
385             390             395             400
Pro Thr Glu Thr Thr Ala Met Thr Glu Thr Phe Val Leu Thr Met Glu
            405             410             415
Tyr Lys Val Ala His His His His His His
            420             425
```

<210> SEQ ID NO 39
<211> LENGTH: 420
<212> TYPE: PRT
<213> ORGANISM: Artificial Sequence
<220> FEATURE:
<223> OTHER INFORMATION: Synthetic Construct

<400> SEQUENCE: 39

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Ser Gly Gly Gly Ser Gly Thr Gln Ser Val
                165                 170                 175

Leu Thr Gln Pro Pro Ser Val Ser Gly Ala Pro Gly Gln Arg Val Thr
            180                 185                 190

Ile Ser Cys Thr Gly Thr Ser Ser Asn Ile Gly Ala His Tyr Asp Val
        195                 200                 205

His Trp Tyr Gln Gln Phe Pro Gly Thr Ala Pro Lys Arg Leu Ile Tyr
210                 215                 220

Gly Asn Asn Asn Arg Pro Ser Gly Val Pro Ala Arg Phe Ser Gly Ser
225                 230                 235                 240

Lys Ser Gly Thr Ser Ala Ser Leu Ala Ile Thr Gly Leu Gln Ala Glu
                245                 250                 255

Asp Glu Ala Asp Tyr Tyr Cys Gln Ser Tyr Asp Arg Ser Leu Arg Gly
            260                 265                 270

Trp Val Phe Gly Gly Gly Thr Lys Leu Thr Val Leu Gly Glu Gly Lys
        275                 280                 285

Ser Ser Gly Ser Gly Ser Glu Ser Lys Ala Ser Glu Val Gln Leu Val
290                 295                 300

Glu Ser Gly Gly Gly Leu Val Gln Pro Gly Arg Ser Leu Arg Leu Ser
305                 310                 315                 320

Cys Ala Ala Ser Gly Phe Thr Phe Asp Asp Tyr Ala Met His Trp Val
                325                 330                 335

Arg Gln Ala Pro Gly Lys Gly Leu Glu Trp Val Ser Gly Ile Ser Trp
            340                 345                 350

Asn Ser Gly Ser Ile Gly Tyr Ala Asp Ser Val Lys Gly Arg Phe Thr
        355                 360                 365

Ile Ser Arg Asp Asn Ser Lys Asn Thr Leu Tyr Leu Gln Met Asn Ser
```

```
            370                 375                 380
Leu Arg Ala Glu Asp Thr Ala Val Tyr Tyr Cys Ala Lys Asp Val Asn
385                 390                 395                 400

Trp Asn Tyr Gly Tyr Tyr Phe Asp Tyr Trp Gly Gln Gly Thr Leu Val
                405                 410                 415

Thr Val Ser Ser
            420

<210> SEQ ID NO 40
<211> LENGTH: 426
<212> TYPE: PRT
<213> ORGANISM: Artificial Sequence
<220> FEATURE:
<223> OTHER INFORMATION: Synthetic Construct

<400> SEQUENCE: 40

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Gly Ser Gly Thr Gln Ser Val
                165                 170                 175

Leu Thr Gln Pro Pro Ser Val Ser Gly Ala Pro Gly Gln Arg Val Thr
            180                 185                 190

Ile Ser Cys Thr Gly Thr Ser Ser Asn Ile Gly Ala His Tyr Asp Val
            195                 200                 205

His Trp Tyr Gln Gln Phe Pro Gly Thr Ala Pro Lys Arg Leu Ile Tyr
            210                 215                 220

Gly Asn Asn Asn Arg Pro Ser Gly Val Pro Ala Arg Phe Ser Gly Ser
225                 230                 235                 240

Lys Ser Gly Thr Ser Ala Ser Leu Ala Ile Thr Gly Leu Gln Ala Glu
                245                 250                 255

Asp Glu Ala Asp Tyr Tyr Cys Gln Ser Tyr Asp Arg Ser Leu Arg Gly
            260                 265                 270

Trp Val Phe Gly Gly Gly Thr Lys Leu Thr Val Leu Gly Glu Gly Lys
            275                 280                 285

Ser Ser Gly Ser Gly Ser Glu Ser Lys Ala Ser Glu Val Gln Leu Val
            290                 295                 300

Glu Ser Gly Gly Gly Leu Val Gln Pro Gly Arg Ser Leu Arg Leu Ser
305                 310                 315                 320
```

```
Cys Ala Ala Ser Gly Phe Thr Phe Asp Asp Tyr Ala Met His Trp Val
                325                 330                 335

Arg Gln Ala Pro Gly Lys Gly Leu Glu Trp Val Ser Gly Ile Ser Trp
            340                 345                 350

Asn Ser Gly Ser Ile Gly Tyr Ala Asp Ser Val Lys Gly Arg Phe Thr
        355                 360                 365

Ile Ser Arg Asp Asn Ser Lys Asn Thr Leu Tyr Leu Gln Met Asn Ser
    370                 375                 380

Leu Arg Ala Glu Asp Thr Ala Val Tyr Tyr Cys Ala Lys Asp Val Asn
385                 390                 395                 400

Trp Asn Tyr Gly Tyr Tyr Phe Asp Tyr Trp Gly Gln Gly Thr Leu Val
                405                 410                 415

Thr Val Ser Ser His His His His His His
                420                 425

<210> SEQ ID NO 41
<211> LENGTH: 425
<212> TYPE: PRT
<213> ORGANISM: Artificial Sequence
<220> FEATURE:
<223> OTHER INFORMATION: Synthetic Construct

<400> SEQUENCE: 41

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Gly Ser Gly Gly Gly Gly Ser
                165                 170                 175

Gly Thr Gln Ser Val Leu Thr Gln Pro Pro Ser Val Ser Gly Ala Pro
            180                 185                 190

Gly Gln Arg Val Thr Ile Ser Cys Thr Gly Thr Ser Ser Asn Ile Gly
        195                 200                 205

Ala His Tyr Asp Val His Trp Tyr Gln Gln Phe Pro Gly Thr Ala Pro
    210                 215                 220

Lys Arg Leu Ile Tyr Gly Asn Asn Asn Arg Pro Ser Gly Val Pro Ala
225                 230                 235                 240

Arg Phe Ser Gly Ser Lys Ser Gly Thr Ser Ala Ser Leu Ala Ile Thr
                245                 250                 255
```

Gly Leu Gln Ala Glu Asp Glu Ala Asp Tyr Tyr Cys Gln Ser Tyr Asp
                260                 265                 270

Arg Ser Leu Arg Gly Trp Val Phe Gly Gly Thr Lys Leu Thr Val
            275                 280                 285

Leu Gly Glu Gly Lys Ser Ser Gly Ser Gly Ser Glu Ser Lys Ala Ser
        290                 295                 300

Glu Val Gln Leu Val Glu Ser Gly Gly Gly Leu Val Gln Pro Gly Arg
305                 310                 315                 320

Ser Leu Arg Leu Ser Cys Ala Ala Ser Gly Phe Thr Phe Asp Asp Tyr
                325                 330                 335

Ala Met His Trp Val Arg Gln Ala Pro Gly Lys Gly Leu Glu Trp Val
            340                 345                 350

Ser Gly Ile Ser Trp Asn Ser Gly Ser Ile Gly Tyr Ala Asp Ser Val
        355                 360                 365

Lys Gly Arg Phe Thr Ile Ser Arg Asp Asn Ser Lys Asn Thr Leu Tyr
            370                 375                 380

Leu Gln Met Asn Ser Leu Arg Ala Glu Asp Thr Ala Val Tyr Tyr Cys
385                 390                 395                 400

Ala Lys Asp Val Asn Trp Asn Tyr Gly Tyr Tyr Phe Asp Tyr Trp Gly
                405                 410                 415

Gln Gly Thr Leu Val Thr Val Ser Ser
            420                 425

<210> SEQ ID NO 42
<211> LENGTH: 431
<212> TYPE: PRT
<213> ORGANISM: Artificial Sequence
<220> FEATURE:
<223> OTHER INFORMATION: Synthetic Construct

<400> SEQUENCE: 42

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Ser
                165                 170                 175

Gly Thr Gln Ser Val Leu Thr Gln Pro Pro Ser Val Ser Gly Ala Pro
            180                 185                 190

Gly Gln Arg Val Thr Ile Ser Cys Thr Gly Thr Ser Ser Asn Ile Gly

```
                195                 200                 205
Ala His Tyr Asp Val His Trp Tyr Gln Gln Phe Pro Gly Thr Ala Pro
    210                 215                 220

Lys Arg Leu Ile Tyr Gly Asn Asn Arg Pro Ser Gly Val Pro Ala
225                 230                 235                 240

Arg Phe Ser Gly Ser Lys Ser Gly Thr Ser Ala Ser Leu Ala Ile Thr
                245                 250                 255

Gly Leu Gln Ala Glu Asp Glu Ala Asp Tyr Tyr Cys Gln Ser Tyr Asp
            260                 265                 270

Arg Ser Leu Arg Gly Trp Val Phe Gly Gly Gly Thr Lys Leu Thr Val
        275                 280                 285

Leu Gly Glu Gly Lys Ser Ser Gly Ser Gly Ser Glu Ser Lys Ala Ser
    290                 295                 300

Glu Val Gln Leu Val Glu Ser Gly Gly Gly Leu Val Gln Pro Gly Arg
305                 310                 315                 320

Ser Leu Arg Leu Ser Cys Ala Ala Ser Gly Phe Thr Phe Asp Asp Tyr
                325                 330                 335

Ala Met His Trp Val Arg Gln Ala Pro Gly Lys Gly Leu Glu Trp Val
            340                 345                 350

Ser Gly Ile Ser Trp Asn Ser Gly Ser Ile Gly Tyr Ala Asp Ser Val
        355                 360                 365

Lys Gly Arg Phe Thr Ile Ser Arg Asp Asn Ser Lys Asn Thr Leu Tyr
    370                 375                 380

Leu Gln Met Asn Ser Leu Arg Ala Glu Asp Thr Ala Val Tyr Tyr Cys
385                 390                 395                 400

Ala Lys Asp Val Asn Trp Asn Tyr Gly Tyr Tyr Phe Asp Tyr Trp Gly
                405                 410                 415

Gln Gly Thr Leu Val Thr Val Ser Ser His His His His His
            420                 425                 430

<210> SEQ ID NO 43
<211> LENGTH: 430
<212> TYPE: PRT
<213> ORGANISM: Artificial Sequence
<220> FEATURE:
<223> OTHER INFORMATION: Synthetic Construct

<400> SEQUENCE: 43

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140
```

```
Cys Gln Ser Ile Ile Ser Thr Leu Thr His Ser Ser Lys Leu Gln Glu
145                 150                 155                 160

Phe Gly Gly Gly Ser Gly Gly Gly Ser Gly Gly Gly Ser
            165                 170                 175

Gly Gly Gly Gly Ser Gly Thr Gln Ser Val Leu Thr Gln Pro Pro Ser
            180                 185                 190

Val Ser Gly Ala Pro Gly Gln Arg Val Thr Ile Ser Cys Thr Gly Thr
            195                 200                 205

Ser Ser Asn Ile Gly Ala His Tyr Asp Val His Trp Tyr Gln Gln Phe
    210                 215                 220

Pro Gly Thr Ala Pro Lys Arg Leu Ile Tyr Gly Asn Asn Asn Arg Pro
225                 230                 235                 240

Ser Gly Val Pro Ala Arg Phe Ser Gly Ser Lys Ser Gly Thr Ser Ala
                245                 250                 255

Ser Leu Ala Ile Thr Gly Leu Gln Ala Glu Asp Glu Ala Asp Tyr Tyr
            260                 265                 270

Cys Gln Ser Tyr Asp Arg Ser Leu Arg Gly Trp Val Phe Gly Gly Gly
        275                 280                 285

Thr Lys Leu Thr Val Leu Gly Glu Gly Lys Ser Ser Gly Ser Gly Ser
    290                 295                 300

Glu Ser Lys Ala Ser Glu Val Gln Leu Val Glu Ser Gly Gly Gly Leu
305                 310                 315                 320

Val Gln Pro Gly Arg Ser Leu Arg Leu Ser Cys Ala Ala Ser Gly Phe
                325                 330                 335

Thr Phe Asp Asp Tyr Ala Met His Trp Val Arg Gln Ala Pro Gly Lys
            340                 345                 350

Gly Leu Glu Trp Val Ser Gly Ile Ser Trp Asn Ser Gly Ser Ile Gly
        355                 360                 365

Tyr Ala Asp Ser Val Lys Gly Arg Phe Thr Ile Ser Arg Asp Asn Ser
    370                 375                 380

Lys Asn Thr Leu Tyr Leu Gln Met Asn Ser Leu Arg Ala Glu Asp Thr
385                 390                 395                 400

Ala Val Tyr Tyr Cys Ala Lys Asp Val Asn Trp Asn Tyr Gly Tyr Tyr
                405                 410                 415

Phe Asp Tyr Trp Gly Gln Gly Thr Leu Val Thr Val Ser Ser
            420                 425                 430

<210> SEQ ID NO 44
<211> LENGTH: 436
<212> TYPE: PRT
<213> ORGANISM: Artificial Sequence
<220> FEATURE:
<223> OTHER INFORMATION: Synthetic Construct

<400> SEQUENCE: 44

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80
```

```
Glu Glu Leu Lys Pro Leu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr His Ser Ser Lys Leu Gln Glu
145                 150                 155                 160

Phe Gly Gly Gly Ser Gly Gly Gly Ser Gly Gly Gly Ser
                165                 170                 175

Gly Gly Gly Gly Ser Gly Thr Gln Ser Val Leu Thr Gln Pro Pro Ser
        180                 185                 190

Val Ser Gly Ala Pro Gly Gln Arg Val Thr Ile Ser Cys Thr Gly Thr
    195                 200                 205

Ser Ser Asn Ile Gly Ala His Tyr Asp Val His Trp Tyr Gln Gln Phe
    210                 215                 220

Pro Gly Thr Ala Pro Lys Arg Leu Ile Tyr Gly Asn Asn Asn Arg Pro
225                 230                 235                 240

Ser Gly Val Pro Ala Arg Phe Ser Gly Ser Lys Ser Gly Thr Ser Ala
                245                 250                 255

Ser Leu Ala Ile Thr Gly Leu Gln Ala Glu Asp Glu Ala Asp Tyr Tyr
            260                 265                 270

Cys Gln Ser Tyr Asp Arg Ser Leu Arg Gly Trp Val Phe Gly Gly Gly
        275                 280                 285

Thr Lys Leu Thr Val Leu Gly Glu Gly Lys Ser Ser Gly Ser Gly Ser
    290                 295                 300

Glu Ser Lys Ala Ser Glu Val Gln Leu Val Glu Ser Gly Gly Gly Leu
305                 310                 315                 320

Val Gln Pro Gly Arg Ser Leu Arg Leu Ser Cys Ala Ala Ser Gly Phe
                325                 330                 335

Thr Phe Asp Asp Tyr Ala Met His Trp Val Arg Gln Ala Pro Gly Lys
            340                 345                 350

Gly Leu Glu Trp Val Ser Gly Ile Ser Trp Asn Ser Gly Ser Ile Gly
        355                 360                 365

Tyr Ala Asp Ser Val Lys Gly Arg Phe Thr Ile Ser Arg Asp Asn Ser
    370                 375                 380

Lys Asn Thr Leu Tyr Leu Gln Met Asn Ser Leu Arg Ala Glu Asp Thr
385                 390                 395                 400

Ala Val Tyr Tyr Cys Ala Lys Asp Val Asn Trp Asn Tyr Gly Tyr Tyr
                405                 410                 415

Phe Asp Tyr Trp Gly Gln Gly Thr Leu Val Thr Val Ser Ser His His
            420                 425                 430

His His His His
        435

<210> SEQ ID NO 45
<211> LENGTH: 392
<212> TYPE: PRT
<213> ORGANISM: Artificial Sequence
<220> FEATURE:
<223> OTHER INFORMATION: Synthetic Construct

<400> SEQUENCE: 45

Met Tyr Arg Met Gln Leu Leu Ser Cys Ile Ala Leu Ser Leu Ala Leu
```

```
                1               5                  10                 15
Val Thr Asn Ser Ala Pro Thr Ser Ser Thr Lys Lys Thr Gln Leu
                    20                  25                 30

Gln Leu Glu His Leu Leu Asp Leu Gln Met Ile Leu Asn Gly Ile
                    35                  40                 45

Asn Asn Tyr Lys Asn Pro Lys Leu Thr Arg Met Leu Thr Phe Lys Phe
 50                  55                      60

Tyr Met Pro Lys Lys Ala Thr Glu Leu Lys His Leu Gln Cys Leu Glu
 65                      70                  75                  80

Glu Glu Leu Lys Pro Leu Glu Glu Val Leu Asn Leu Ala Gln Ser Lys
                        85                  90                  95

Asn Phe His Leu Arg Pro Arg Asp Leu Ile Ser Asn Ile Asn Val Ile
                    100                 105                110

Val Leu Glu Leu Lys Gly Ser Glu Thr Thr Phe Met Cys Glu Tyr Ala
                    115                 120                 125

Asp Glu Thr Ala Thr Ile Val Glu Phe Leu Asn Arg Trp Ile Thr Phe
                    130                 135                 140

Cys Gln Ser Ile Ile Ser Thr Leu Thr His Ser Ser Lys Leu Gln Glu
145                     150                 155                 160

Phe Gly Gly Gly Ser Gly Gly Gly Ser Gly Thr Glu Leu Cys
                    165                 170                 175

Asp Asp Asp Pro Pro Glu Ile Pro His Ala Thr Phe Lys Ala Met Ala
                    180                 185                 190

Tyr Lys Glu Gly Thr Met Leu Asn Cys Glu Cys Lys Arg Gly Phe Arg
                    195                 200                 205

Arg Ile Lys Ser Gly Ser Leu Tyr Met Leu Cys Thr Gly Asn Ser Ser
        210                 215                 220

His Ser Ser Trp Asp Asn Gln Cys Gln Cys Thr Ser Ser Ala Thr Arg
225                 230                 235                 240

Asn Thr Thr Lys Gln Val Thr Pro Gln Pro Glu Glu Gln Lys Glu Arg
                    245                 250                 255

Lys Thr Thr Glu Met Gln Ser Pro Met Gln Pro Val Asp Gln Ala Ser
                    260                 265                 270

Leu Pro Gly His Cys Arg Glu Pro Pro Trp Glu Asn Glu Ala Thr
                275                 280                 285

Glu Arg Ile Tyr His Phe Val Val Gly Gln Met Val Tyr Tyr Gln Cys
        290                 295                 300

Val Gln Gly Tyr Arg Ala Leu His Arg Gly Pro Ala Glu Ser Val Cys
305                 310                 315                 320

Lys Met Thr His Gly Lys Thr Arg Trp Thr Gln Pro Gln Leu Ile Cys
                    325                 330                 335

Thr Gly Glu Met Glu Thr Ser Gln Phe Pro Gly Glu Glu Lys Pro Gln
                    340                 345                 350

Ala Ser Pro Glu Gly Arg Pro Glu Ser Glu Thr Ser Cys Leu Val Thr
                    355                 360                 365

Thr Thr Asp Phe Gln Ile Gln Thr Glu Met Ala Ala Thr Met Glu Thr
                    370                 375                 380

Ser Ile Phe Thr Thr Glu Tyr Gln
385                 390

<210> SEQ ID NO 46
<211> LENGTH: 397
<212> TYPE: PRT
<213> ORGANISM: Artificial Sequence
<220> FEATURE:
```

<223> OTHER INFORMATION: Synthetic Construct

<400> SEQUENCE: 46

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65              70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Gly Ser
                165                 170                 175

Gly Thr Glu Leu Cys Asp Asp Asp Pro Pro Glu Ile Pro His Ala Thr
                180                 185                 190

Phe Lys Ala Met Ala Tyr Lys Glu Gly Thr Met Leu Asn Cys Glu Cys
            195                 200                 205

Lys Arg Gly Phe Arg Arg Ile Lys Ser Gly Ser Leu Tyr Met Leu Cys
            210                 215                 220

Thr Gly Asn Ser Ser His Ser Ser Trp Asp Asn Gln Cys Gln Cys Thr
225                 230                 235                 240

Ser Ser Ala Thr Arg Asn Thr Thr Lys Gln Val Thr Pro Gln Pro Glu
            245                 250                 255

Glu Gln Lys Glu Arg Lys Thr Thr Glu Met Gln Ser Pro Met Gln Pro
            260                 265                 270

Val Asp Gln Ala Ser Leu Pro Gly His Cys Arg Glu Pro Pro Pro Trp
            275                 280                 285

Glu Asn Glu Ala Thr Glu Arg Ile Tyr His Phe Val Val Gly Gln Met
            290                 295                 300

Val Tyr Tyr Gln Cys Val Gln Gly Tyr Arg Ala Leu His Arg Gly Pro
305                 310                 315                 320

Ala Glu Ser Val Cys Lys Met Thr His Gly Lys Thr Arg Trp Thr Gln
                325                 330                 335

Pro Gln Leu Ile Cys Thr Gly Glu Met Glu Thr Ser Gln Phe Pro Gly
            340                 345                 350

Glu Glu Lys Pro Gln Ala Ser Pro Glu Gly Arg Pro Glu Ser Glu Thr
            355                 360                 365

Ser Cys Leu Val Thr Thr Thr Asp Phe Gln Ile Gln Thr Glu Met Ala
            370                 375                 380

Ala Thr Met Glu Thr Ser Ile Phe Thr Thr Glu Tyr Gln
385                 390                 395
```

```
<210> SEQ ID NO 47
<211> LENGTH: 403
<212> TYPE: PRT
<213> ORGANISM: Artificial Sequence
<220> FEATURE:
<223> OTHER INFORMATION: Synthetic Construct

<400> SEQUENCE: 47

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Gly Ser
                165                 170                 175

Gly Thr Glu Leu Cys Asp Asp Asp Pro Pro Glu Ile Pro His Ala Thr
            180                 185                 190

Phe Lys Ala Met Ala Tyr Lys Glu Gly Thr Met Leu Asn Cys Glu Cys
        195                 200                 205

Lys Arg Gly Phe Arg Arg Ile Lys Ser Gly Ser Leu Tyr Met Leu Cys
210                 215                 220

Thr Gly Asn Ser Ser His Ser Ser Trp Asp Asn Gln Cys Gln Cys Thr
225                 230                 235                 240

Ser Ser Ala Thr Arg Asn Thr Thr Lys Gln Val Thr Pro Gln Pro Glu
                245                 250                 255

Glu Gln Lys Glu Arg Lys Thr Thr Glu Met Gln Ser Pro Met Gln Pro
            260                 265                 270

Val Asp Gln Ala Ser Leu Pro Gly His Cys Arg Glu Pro Pro Pro Trp
        275                 280                 285

Glu Asn Glu Ala Thr Glu Arg Ile Tyr His Phe Val Val Gly Gln Met
290                 295                 300

Val Tyr Tyr Gln Cys Val Gln Gly Tyr Arg Ala Leu His Arg Gly Pro
305                 310                 315                 320

Ala Glu Ser Val Cys Lys Met Thr His Gly Lys Thr Arg Trp Thr Gln
                325                 330                 335

Pro Gln Leu Ile Cys Thr Gly Glu Met Glu Thr Ser Gln Phe Pro Gly
            340                 345                 350

Glu Glu Lys Pro Gln Ala Ser Pro Glu Gly Arg Pro Glu Ser Glu Thr
        355                 360                 365

Ser Cys Leu Val Thr Thr Thr Asp Phe Gln Ile Gln Thr Glu Met Ala
370                 375                 380
```

```
Ala Thr Met Glu Thr Ser Ile Phe Thr Thr Glu Tyr Gln His His
385                 390                 395                 400

His His His

<210> SEQ ID NO 48
<211> LENGTH: 399
<212> TYPE: PRT
<213> ORGANISM: Artificial Sequence
<220> FEATURE:
<223> OTHER INFORMATION: Synthetic Construct

<400> SEQUENCE: 48

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Asp Leu Gln Met Ile Leu Asn Gly Ile
                35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Gly Ser
                165                 170                 175

Gly Thr Glu Leu Cys Asp Asp Asp Pro Pro Glu Ile Pro His Ala Thr
                180                 185                 190

Phe Lys Ala Met Ala Tyr Lys Glu Gly Thr Met Leu Asn Cys Glu Cys
            195                 200                 205

Lys Arg Gly Phe Arg Arg Ile Lys Ser Gly Ser Leu Tyr Met Leu Cys
            210                 215                 220

Thr Gly Asn Ser Ser His Ser Ser Trp Asp Asn Gln Cys Gln Cys Thr
225                 230                 235                 240

Ser Ser Ala Thr Arg Asn Thr Thr Lys Gln Val Thr Pro Gln Pro Glu
                245                 250                 255

Glu Gln Lys Glu Arg Lys Thr Thr Glu Met Gln Ser Pro Met Gln Pro
                260                 265                 270

Val Asp Gln Ala Ser Leu Pro Gly His Cys Arg Glu Pro Pro Pro Trp
            275                 280                 285

Glu Asn Glu Ala Thr Glu Arg Ile Tyr His Phe Val Val Gly Gln Met
            290                 295                 300

Val Tyr Tyr Gln Cys Val Gln Gly Tyr Arg Ala Leu His Arg Gly Pro
305                 310                 315                 320

Ala Glu Ser Val Cys Lys Met Thr His Gly Lys Thr Arg Trp Thr Gln
                325                 330                 335

Pro Gln Leu Ile Cys Thr Gly Glu Met Glu Thr Ser Gln Phe Pro Gly
```

```
                    340                 345                 350
Glu Glu Lys Pro Gln Ala Ser Pro Glu Gly Arg Pro Glu Ser Glu Thr
            355                 360                 365

Ser Cys Leu Val Thr Thr Thr Asp Phe Gln Ile Gln Thr Glu Met Ala
370                 375                 380

Ala Thr Met Glu Thr Ser Ile Phe Thr Thr Glu Tyr Gln Val Ala
385                 390                 395

<210> SEQ ID NO 49
<211> LENGTH: 405
<212> TYPE: PRT
<213> ORGANISM: Artificial Sequence
<220> FEATURE:
<223> OTHER INFORMATION: Synthetic Construct

<400> SEQUENCE: 49

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Gly Ser
                165                 170                 175

Gly Thr Glu Leu Cys Asp Asp Asp Pro Pro Glu Ile Pro His Ala Thr
            180                 185                 190

Phe Lys Ala Met Ala Tyr Lys Glu Gly Thr Met Leu Asn Cys Glu Cys
        195                 200                 205

Lys Arg Gly Phe Arg Arg Ile Lys Ser Gly Ser Leu Tyr Met Leu Cys
210                 215                 220

Thr Gly Asn Ser Ser His Ser Ser Trp Asp Asn Gln Cys Gln Cys Thr
225                 230                 235                 240

Ser Ser Ala Thr Arg Asn Thr Lys Gln Val Thr Pro Gln Pro Glu
                245                 250                 255

Glu Gln Lys Glu Arg Lys Thr Thr Glu Met Gln Ser Pro Met Gln Pro
            260                 265                 270

Val Asp Gln Ala Ser Leu Pro Gly His Cys Arg Glu Pro Pro Pro Trp
        275                 280                 285

Glu Asn Glu Ala Thr Glu Arg Ile Tyr His Phe Val Val Gly Gln Met
290                 295                 300

Val Tyr Tyr Gln Cys Val Gln Gly Tyr Arg Ala Leu His Arg Gly Pro
305                 310                 315                 320
```

```
Ala Glu Ser Val Cys Lys Met Thr His Gly Lys Thr Arg Trp Thr Gln
                325                 330                 335

Pro Gln Leu Ile Cys Thr Gly Glu Met Glu Thr Ser Gln Phe Pro Gly
            340                 345                 350

Glu Glu Lys Pro Gln Ala Ser Pro Glu Gly Arg Pro Ser Glu Thr
            355                 360                 365

Ser Cys Leu Val Thr Thr Thr Asp Phe Gln Ile Gln Thr Glu Met Ala
370                 375                 380

Ala Thr Met Glu Thr Ser Ile Phe Thr Thr Glu Tyr Gln Val Ala His
385                 390                 395                 400

His His His His His
                405

<210> SEQ ID NO 50
<211> LENGTH: 409
<212> TYPE: PRT
<213> ORGANISM: Artificial Sequence
<220> FEATURE:
<223> OTHER INFORMATION: Synthetic Construct

<400> SEQUENCE: 50

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr His Ser Ser Lys Leu Gln Glu
145                 150                 155                 160

Phe Gly Gly Gly Gly Ser Gly Gly Gly Ser Gly Gly Gly Gly Ser
                165                 170                 175

Gly Gly Gly Gly Ser Gly Gly Gly Ser Gly Thr Glu Leu Cys Asp
            180                 185                 190

Asp Asp Pro Pro Glu Ile Pro His Ala Thr Phe Lys Ala Met Ala Tyr
            195                 200                 205

Lys Glu Gly Thr Met Leu Asn Cys Glu Cys Lys Arg Gly Phe Arg Arg
            210                 215                 220

Ile Lys Ser Gly Ser Leu Tyr Met Leu Cys Thr Gly Asn Ser Ser His
225                 230                 235                 240

Ser Ser Trp Asp Asn Gln Cys Gln Cys Thr Ser Ser Ala Thr Arg Asn
                245                 250                 255

Thr Thr Lys Gln Val Thr Pro Gln Pro Glu Glu Gln Lys Glu Arg Lys
            260                 265                 270
```

Thr Thr Glu Met Gln Ser Pro Met Gln Pro Val Asp Gln Ala Ser Leu
    275                 280                 285
Pro Gly His Cys Arg Glu Pro Pro Trp Glu Asn Glu Ala Thr Glu
    290                 295                 300
Arg Ile Tyr His Phe Val Val Gly Gln Met Val Tyr Tyr Gln Cys Val
305                 310                 315                 320
Gln Gly Tyr Arg Ala Leu His Arg Gly Pro Ala Glu Ser Val Cys Lys
                325                 330                 335
Met Thr His Gly Lys Thr Arg Trp Thr Gln Pro Gln Leu Ile Cys Thr
                340                 345                 350
Gly Glu Met Glu Thr Ser Gln Phe Pro Gly Glu Glu Lys Pro Gln Ala
                355                 360                 365
Ser Pro Glu Gly Arg Pro Glu Ser Glu Thr Ser Cys Leu Val Thr Thr
    370                 375                 380
Thr Asp Phe Gln Ile Gln Thr Glu Met Ala Ala Thr Met Glu Thr Ser
385                 390                 395                 400

Ile Phe Thr Thr Glu Tyr Gln Val Ala
                405

<210> SEQ ID NO 51
<211> LENGTH: 35
<212> TYPE: DNA
<213> ORGANISM: Artificial Sequence
<220> FEATURE:
<223> OTHER INFORMATION: Synthetic Construct

<400> SEQUENCE: 51
cataggtcga catgtacagc atgcagctcg catcc                              35

<210> SEQ ID NO 52
<211> LENGTH: 54
<212> TYPE: DNA
<213> ORGANISM: Artificial Sequence
<220> FEATURE:
<223> OTHER INFORMATION: Synthetic Construct

<400> SEQUENCE: 52
catagggaat tcctgcagct tgctgctgtg ttgagggctt gttgagatga tgct         54

<210> SEQ ID NO 53
<211> LENGTH: 57
<212> TYPE: DNA
<213> ORGANISM: Artificial Sequence
<220> FEATURE:
<223> OTHER INFORMATION: Synthetic Construct

<400> SEQUENCE: 53
ccgcgcgaat tcacctctga cacccagagg accttgaggg cttgttgaga tgatgct      57

<210> SEQ ID NO 54
<211> LENGTH: 32
<212> TYPE: DNA
<213> ORGANISM: Artificial Sequence
<220> FEATURE:
<223> OTHER INFORMATION: Synthetic Construct

<400> SEQUENCE: 54
catagggaat tcgcgccata tggagctgac ac                                 32

<210> SEQ ID NO 55
<211> LENGTH: 32
<212> TYPE: DNA
<213> ORGANISM: Artificial Sequence

```
<220> FEATURE:
<223> OTHER INFORMATION: Synthetic Construct

<400> SEQUENCE: 55
cctatgggat ccggcattca gttccaggtc ag                                    32

<210> SEQ ID NO 56
<211> LENGTH: 35
<212> TYPE: DNA
<213> ORGANISM: Artificial Sequence
<220> FEATURE:
<223> OTHER INFORMATION: Synthetic Construct

<400> SEQUENCE: 56
gcgcgggtac cgaactgtgt ctgtatgacc caccc                                 35

<210> SEQ ID NO 57
<211> LENGTH: 38
<212> TYPE: DNA
<213> ORGANISM: Artificial Sequence
<220> FEATURE:
<223> OTHER INFORMATION: Synthetic Construct

<400> SEQUENCE: 57
cggccggatc ctcattatgc taccttatac tccattgt                              38

<210> SEQ ID NO 58
<211> LENGTH: 56
<212> TYPE: DNA
<213> ORGANISM: Artificial Sequence
<220> FEATURE:
<223> OTHER INFORMATION: Synthetic Construct

<400> SEQUENCE: 58
cggccggatc ctcattagtg gtggtggtgg tggtgtgcta ccttatactc cattgt          56

<210> SEQ ID NO 59
<211> LENGTH: 32
<212> TYPE: DNA
<213> ORGANISM: Artificial Sequence
<220> FEATURE:
<223> OTHER INFORMATION: Synthetic Construct

<400> SEQUENCE: 59
gatacgtcga catgtacagg atgcaactcc tg                                    32

<210> SEQ ID NO 60
<211> LENGTH: 50
<212> TYPE: DNA
<213> ORGANISM: Artificial Sequence
<220> FEATURE:
<223> OTHER INFORMATION: Synthetic Construct

<400> SEQUENCE: 60
tcggagaatt cctgcagctt gctgctgtga gtcagtgttg agatgatgct                 50

<210> SEQ ID NO 61
<211> LENGTH: 56
<212> TYPE: DNA
<213> ORGANISM: Artificial Sequence
<220> FEATURE:
<223> OTHER INFORMATION: Synthetic Construct

<400> SEQUENCE: 61
ggccggaatt cggtggcggt ggctctggtg gcggtggctc tggtggcggt ggctct          56
```

<210> SEQ ID NO 62
<211> LENGTH: 60
<212> TYPE: DNA
<213> ORGANISM: Artificial Sequence
<220> FEATURE:
<223> OTHER INFORMATION: Synthetic Construct

<400> SEQUENCE: 62
gcgggtacca gagccaccgc caccagagcc accgccacca gagccaccgc caccagagcc    60

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gcgcgggtac ccagtctgtg ctgactcagc ca                                  32

<210> SEQ ID NO 64
<211> LENGTH: 32
<212> TYPE: DNA
<213> ORGANISM: Artificial Sequence
<220> FEATURE:
<223> OTHER INFORMATION: Synthetic Construct

<400> SEQUENCE: 64
ccggcggatc ctgaggagac ggtgaccagg gt                                  32

<210> SEQ ID NO 65
<211> LENGTH: 44
<212> TYPE: DNA
<213> ORGANISM: Artificial Sequence
<220> FEATURE:
<223> OTHER INFORMATION: Synthetic Construct

<400> SEQUENCE: 65
ccggcggatc cgtggtggtg gtggtggtgt gaggagacca ggt                      44

<210> SEQ ID NO 66
<211> LENGTH: 37
<212> TYPE: DNA
<213> ORGANISM: Artificial Sequence
<220> FEATURE:
<223> OTHER INFORMATION: Synthetic Construct

<400> SEQUENCE: 66
gcgccgcggc cgcgtcgaca tgtacaggat gcaactc                             37

<210> SEQ ID NO 67
<211> LENGTH: 41
<212> TYPE: DNA
<213> ORGANISM: Artificial Sequence
<220> FEATURE:
<223> OTHER INFORMATION: Synthetic Construct

<400> SEQUENCE: 67
ggcgcggatc ctcattatga ggagacggtg accagggtgc c                        41

<210> SEQ ID NO 68
<211> LENGTH: 56
<212> TYPE: DNA
<213> ORGANISM: Artificial Sequence
<220> FEATURE:
<223> OTHER INFORMATION: Synthetic Construct -continued

```
<400> SEQUENCE: 68
cgcgcggatc ctcattagtg gtggtggtgg tggtgtgagg agacggtgac cagggt         56
```

US 8,734,774 B2

PROTEASE ACTIVATED CYTOKINES

CROSS-REFERENCE TO RELATED APPLICATIONS

This application claims the benefit of U.S. Provisional Application No. 61/320,360, filed on Apr. 2, 2010, which is incorporated by reference herein in its entirety.

REFERENCE TO SEQUENCE LISTING

The Sequence Listing submitted Oct. 2, 2012, as a text file named "10028_027US1_2012_10_02_Sequence_Listing.txt," created on Oct. 2, 2012 and having a size of 113,768 bytes is hereby incorporated by reference pursuant to 37 C.F.R. §1.52(e)(5).

STATEMENT REGARDING FEDERALLY FUNDED RESEARCH

This invention was made with government funding under Grant No. 5T32AI00728 from the National Institutes of Health. The government has certain rights in this invention.

BACKGROUND

Active agents used in the treatment of diseases and infection are often administered systemically at higher doses. Such systemic administration often has profound side-effects, which can be toxic or poorly tolerated. Local administration, however, is not always feasible because such administration is invasive or the targeted location is poorly defined or widely dispersed.

SUMMARY

Provided herein are chimeric nucleic acid sequences encoding chimeric polypeptides. The chimeric nucleic acid sequences comprise a first nucleic acid sequence encoding an interleukin-2 (IL-2) cytokine polypeptide or a fragment thereof; a second nucleic acid sequence encoding an amino acid sequence, wherein the amino acid sequence is capable of being cleaved by a protease; and a third nucleic acid sequence encoding a polypeptide, wherein the polypeptide is capable of blocking the activity of the IL-2 cytokine polypeptide or fragment thereof.

Also provided herein are chimeric polypeptides. The chimeric polypeptides comprise a first polypeptide comprising an interleukin-2 (IL-2) cytokine polypeptide or a fragment thereof; a second polypeptide comprising an amino acid sequence, wherein the amino acid sequence is capable of being cleaved by a protease; and a third polypeptide comprising a polypeptide, wherein the polypeptide is capable of blocking activity of the IL-2 cytokine polypeptide or fragment thereof.

Further provided are methods of treating a subject with or at risk of developing a cancer or an infection. The methods comprise selecting a subject with or at risk of developing a cancer or an infection; and administering to the subject an effective amount of a chimeric polypeptide. The chimeric polypeptide comprises a first polypeptide comprising an interleukin-2 (IL-2) cytokine polypeptide or a fragment thereof; a second polypeptide comprising an amino acid sequence, wherein the amino acid sequence is capable of being cleaved by a protease expressed in the cancer or at the site of infection; and a third polypeptide comprising a polypeptide, wherein the polypeptide is capable of blocking the activity of the IL-2 cytokine polypeptide or fragment thereof.

DESCRIPTION OF DRAWINGS

FIGS. 1A-1D show that the mouse IL-2/MIP-1α fusion protein can be cleaved but IL-2 function does not increase after cleavage. FIG. 1A shows a schematic of secreted IL-2/PSAcs/Mip-1α fusion protein. The PSA cleavage sequence (PSAcs) designates the amino acid sequence HSSKLQ (SEQ ID NO:1) as cleaved by the PSA protease. FIG. 1B shows a histogram of an ELISA analysis of fusion protein using capture antibodies for mouse IL-2 (JES6-1A12) and mouse Mip-1α (39624.11) to detect the IL-2 and Mip-1α portions of the fusion protein. FIG. 1C shows an image of a Western blot of mouse IL-2/PSAcs/Mip-1α fusion protein treated with PSA for 1 hour at 37° C. and analyzed by immunoblot using an anti mouse IL-2 antibody (JES6-1A12). Full length fusion protein and the predicted cleavage product containing IL-2 have been denoted by arrowheads. An increase in the intensity of this band can be seen in the PSA treated fusion protein. FIG. 1D shows an IL-2 functional assay of fusion protein. PSA treatment (○), no PSA treatment (●), or control media only (▲).

FIGS. 2A-2C show the characterization of mouse IL-2/IL-2Rα fusion proteins. FIG. 2A shows a schematic diagram of mouse IL-2/PSAcs/linker/IL-2Rα fusion proteins. The PSA cleavage sequence (PSAcs) designates the amino acid sequence HSSKLQ (SEQ ID NO:1) as cleaved by the PSA protease followed by the $(GGGGS)_2$ (SEQ ID NO:9) (shown) or $(GGGGS)_4$ (SEQ ID NO:10) linker lengths. FIG. 2B shows a histogram of an ELISA analysis of fusion proteins using capture antibodies to IL-2 (JES6-1A12) or IL-2Rα (PC61) and a different biotin-labeled anti-IL-2 detecting antibody (JES5H4) showing that both IL-2 and the IL-2Rα moieties are present on the same molecule. 2× indicates $(GGGGS)_2$ (SEQ ID NO:9) linker, 4× indicates $(GGGGS)_4$ (SEQ ID NO:10) linker, and (+) indicates the construct contains the 6× His tag. FIG. 2C shows an immunoblot analysis of the fusion proteins using antibodies reactive with IL-2 (JES6-1A12), IL-2Rα (PC61) and 6× His epitope tag (MM5-156P). Molecular weight standards are indicated. The full-length fusion proteins have an approximate molecular weight of 50 kDa.

FIGS. 3A-3F show PSA treatment enhances antibody accessibility and IL-2 functional activity in mouse IL-2/IL-2Rα fusion proteins. Fusion proteins (2× and 4× linker lengths) were treated with PSA or buffer controls for 1 hour at 37° C. and aliquots were analyzed by immunoblot, ELISA, or by functional analysis. FIG. 3A shows an image of an IL-2 immunoblot analysis of fusion proteins before and after treatment with PSA. Bars indicate molecular weight markers, (+) indicates treatment with PSA, (−) indicates treatment with control buffer, and full length and predicted cleavage product containing IL-2 have been denoted (arrowheads). FIG. 3B shows an image of an immunoblot analysis of a titration of PSA using mouse IL-2/PSAcs/2× linker/IL-2Rα fusion protein at 37° C. for 1 hour. The immunoblot analysis was performed using an anti-mouse IL-2 antibody (JES6-1A12). Bars and numbers indicate molecular weight markers. Full length and cleaved fusion protein have been denoted. Amount of PSA (μg) in the reaction (Cortex) used is as follows: 11.25, 5.6, 2.8, 1.4 and 0. FIG. 3C shows an image of an immunoblot analysis of a PSA time course using mouse IL-2/PSAcs/4× linker/IL-2Rα fusion protein digested for 0, 1, 3, 6, 12 and 24 hours at 37° C. The immunoblot analysis was performed using an anti-mouse IL-2 antibody (JES6-1A12). FIG. 3D shows a histogram of an ELISA used to measure the amount of IL-2 before and after treatment with PSA. An apparent increase in IL-2 can be seen after PSA incubation for both fusion proteins tested. FIGS. 3E and 3F show functional analyses of IL-2 before and after cleavage. Biologically active IL-2 from the fusion proteins was measured using the CTLL-2 functional assay as described in the general methods. Fusion protein treated with PSA (○), or with buffer control (●), IL-2 standard (■), and media control (▲). The first point in the dilution series represents approximately 16 ng of each fusion protein (circles). For the IL-2 standard the first point represents 0.5 ng recombinant IL-2 (■). Points represent the average of 3 replicates and error bars indicate standard deviation. Representative of 3 independent experiments.

Figure 4A:
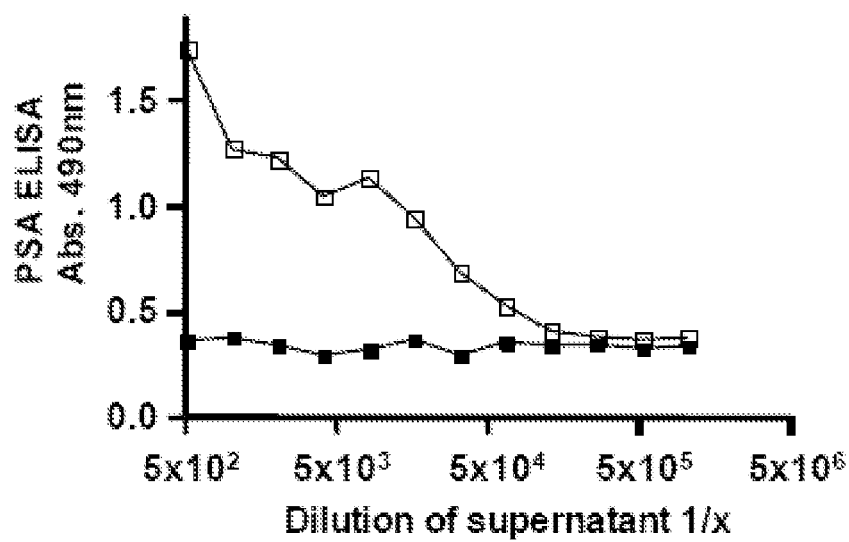
Figure 4B:
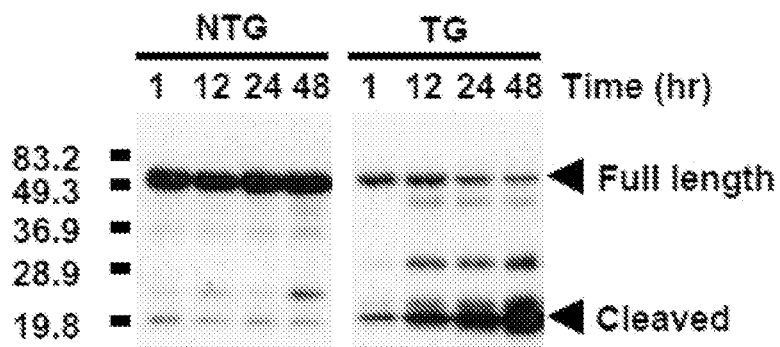
Figure 4C:
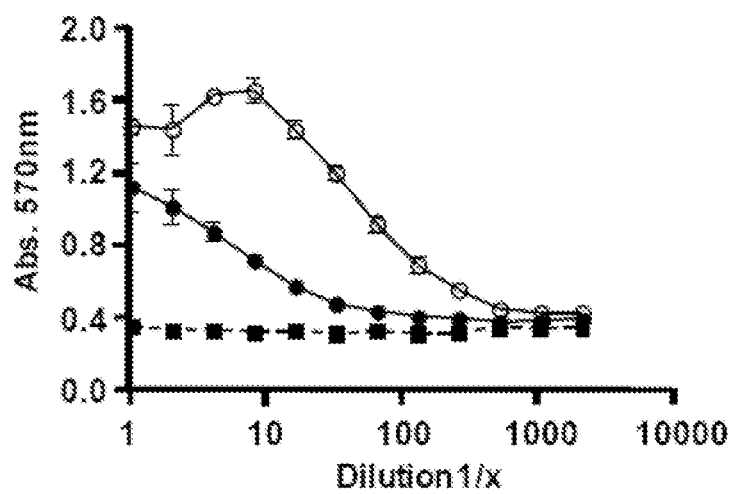
Figure 4D:
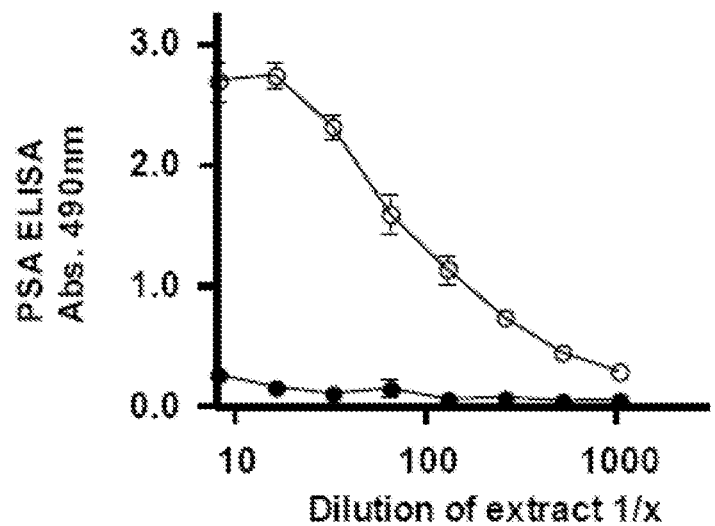
Figure 4E:
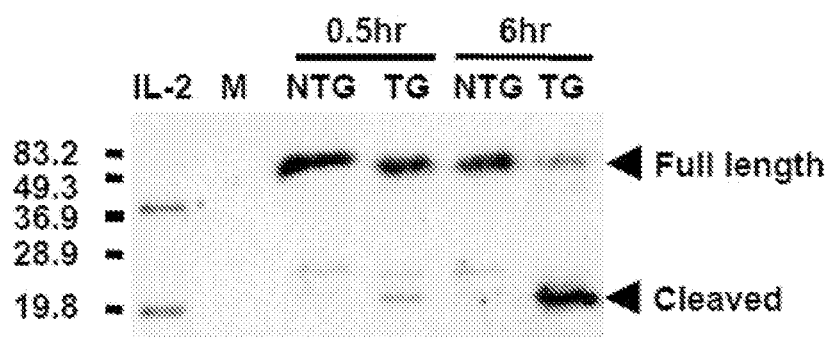
Figure 4F:
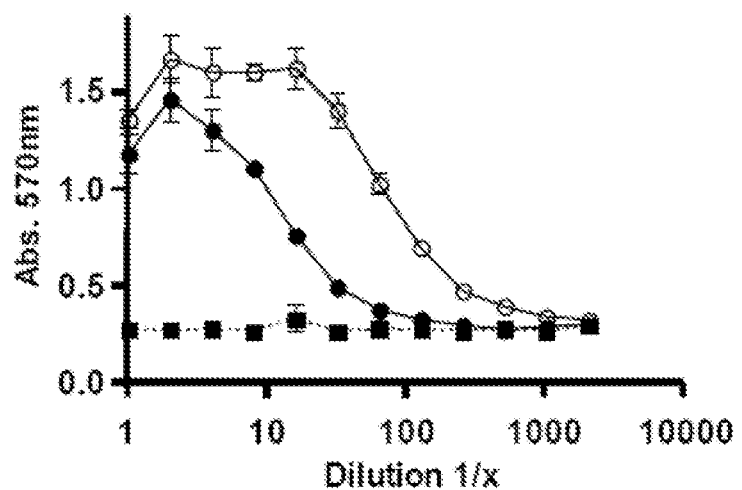

FIGS. 4A-4F show IL-2 bioactivity increases when IL-2/PSAcs/4× linker/IL-2Rα fusion protein is cultured with explanted prostates or homogenized prostate extracts. Prostates were removed from nontransgenic (NTG) or PSA transgenic (TG) C57BL/6J mice, cultured at 37° C. with fusion protein and aliquots of media containing fusion protein were removed at 1, 12, 24, 48 hours for analysis. FIG. 4A shows detection of PSA in TG (□) or NTG (■) supernatant aliquots at 48 hours by ELISA. FIG. 4B shows an image of an immunoblot analysis of the culture supernatants at the indicated time points. Bars and numbers indicate molecular weight markers. Full length and the predicted cleavage product containing IL-2 are indicated by arrowheads. FIG. 4C shows IL-2 functional assay at 48 hours. Supernatant from cultures containing TG prostate explants (○), NTG explants (●), media control (■). First dilution point represents equal amounts of fusion protein for both conditions tested. FIG. 4D shows analysis of PSA by ELISA in homogenized prostate extracts from TG (○) and NTG (●) mice. The first well represents approximately 40 ng of NTG or TG extract. FIG. 4E shows an image of an immunoblot analysis of the samples containing prostate extracts and the fusion protein at 0.5 or 6 hours at 37° C. Bacterially derived non-glycosylated recombinant mouse IL-2 (10 ng) was used as a standard and has an approximate molecular weight of 18.5 kDa. The band at approximately 37 kDa in the control lane likely represents a dimer of IL-2. Full-length fusion protein and the predicted cleavage product containing IL-2 have been denoted by arrowheads. FIG. 4F shows an IL-2 functional assay of fusion proteins after incubation with prostate extracts. TG prostate extracts (○), NTG extracts (●) and media control (■). The first well has equal amounts of fusion protein for both conditions.

Figure 5A:
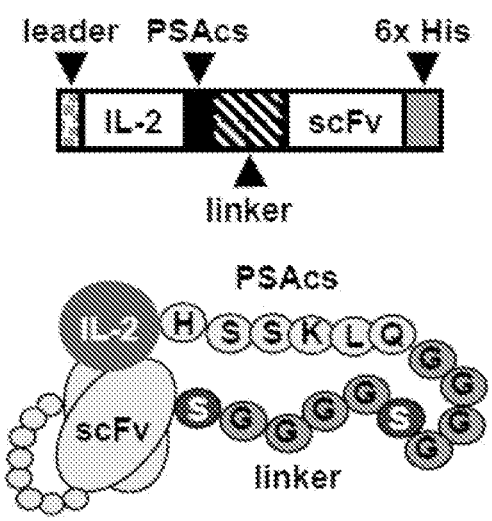
Figure 5B:
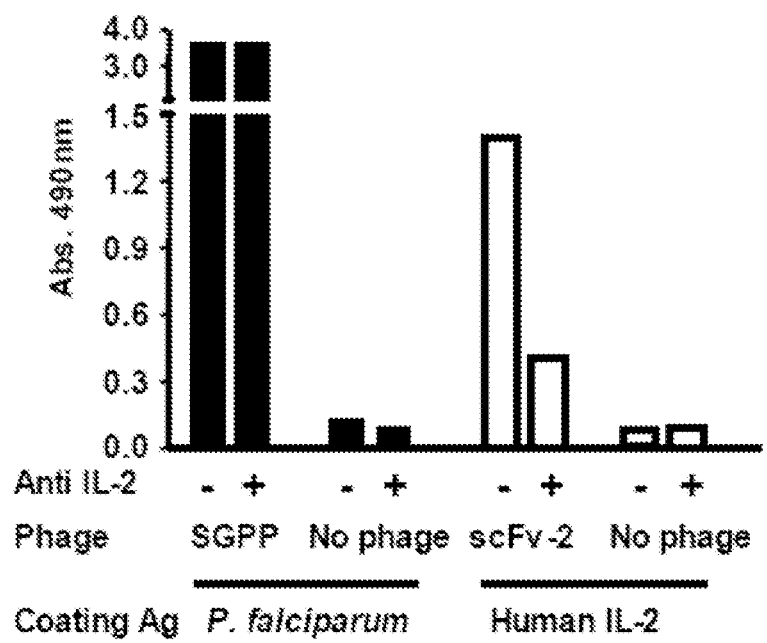
Figure 5C:
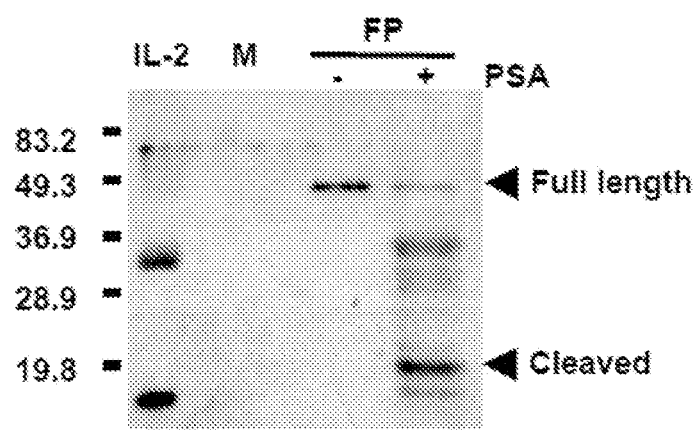
Figure 5D:
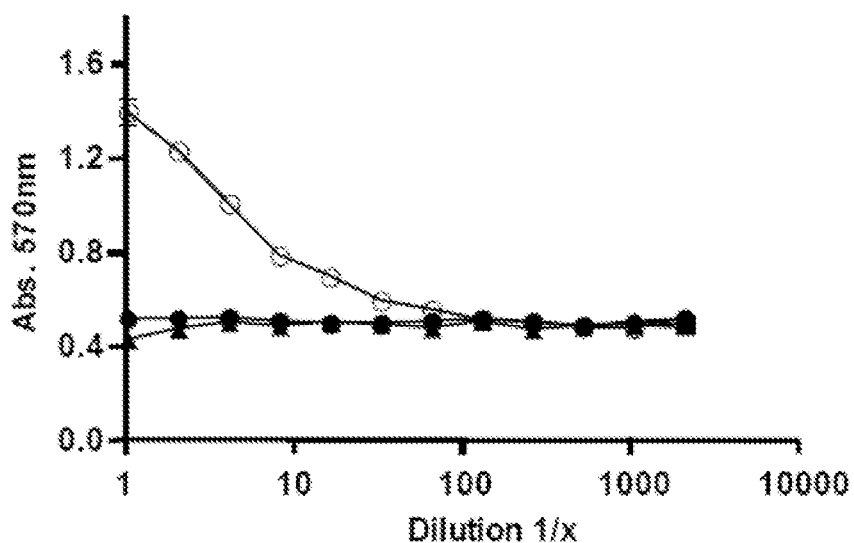

FIGS. 5A-5D show the characterization and analyses of human IL-2/scFv fusion proteins. FIG. 5A shows a schematic diagram of human IL-2/scFv fusion proteins containing human IL-2 fused to the PSAcs, a (GGGGS)$_2$ (SEQ ID NO:9) or (GGGGS)$_4$ (SEQ ID NO:10) linker unit followed by VL and VH fragments of an antibody tethered together by a linker (scFv) and a 6× His carboxyl tag. FIG. 5B shows a histogram of the results of a modified ELISA assay using scFv phage. The modified ELISA assay was performed and a phage clone expressing scFv (phscFv) that binds human IL-2 (scFv-2) was screened for the ability to be inhibited by the anti-human IL-2 neutralizing antibody (MQ1-17H12). Black columns indicate recombinant *P. falciparum* protein (SGPP) coating antigen, white columns indicate human IL-2 as the coating antigen. A phage which bound SGPP served as a control and this binding was not inhibited by the anti-human IL-2 neutralizing antibody while the phage clone scFv-2 could be partially blocked by the antibody. FIG. 5C shows an image of an anti-human IL-2 immunoblot analysis of fusion protein treated with purified PSA or with control PSA buffer treatment at 37° C. for 24 hours. Bars and numbers indicate molecular weight markers. Full-length fusion protein and the predicted cleavage product containing IL-2 have been denoted with arrowheads. Media negative control (M). Bacterially derived non-glycosylated recombinant human IL-2 (50 ng) was used as a standard and has an approximate molecular weight of 15.5 kDa. The fusion protein IL-2 was derived from insect cells and may be post-translationally modified accounting for its slightly higher molecular weight. FIG. 5D shows a graph presenting the results of an IL-2 functional assay on fusion protein. Treatment with PSA (○), control buffer (●) or media control (▲). Equal amounts of Ni-NTA purified fusion protein loaded in first well for both conditions tested.

Figure 6A:
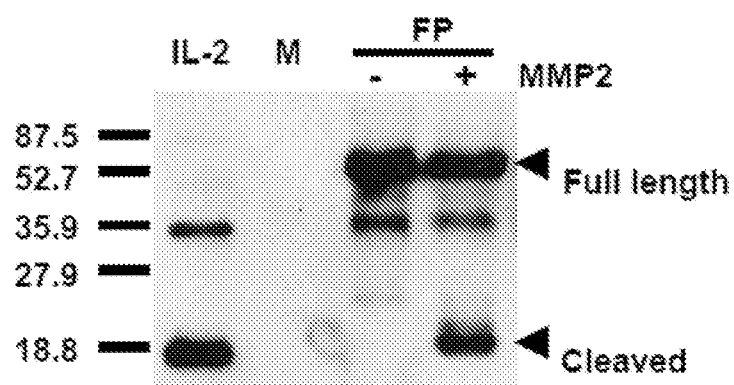
Figure 6B:
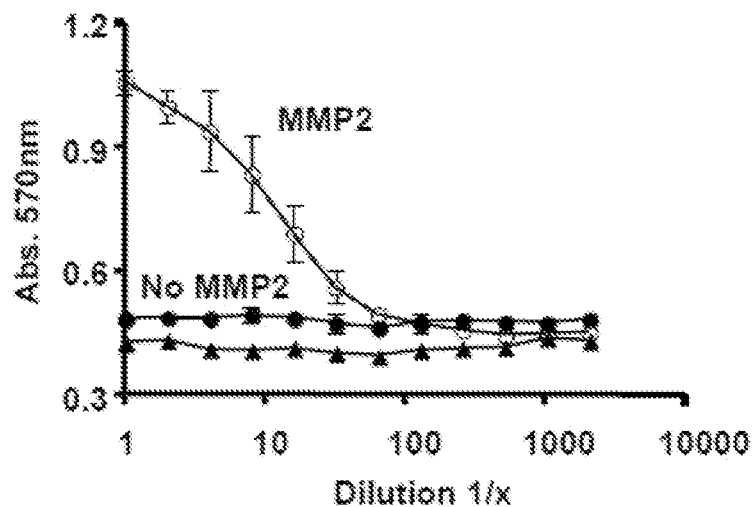
Figure 6C:
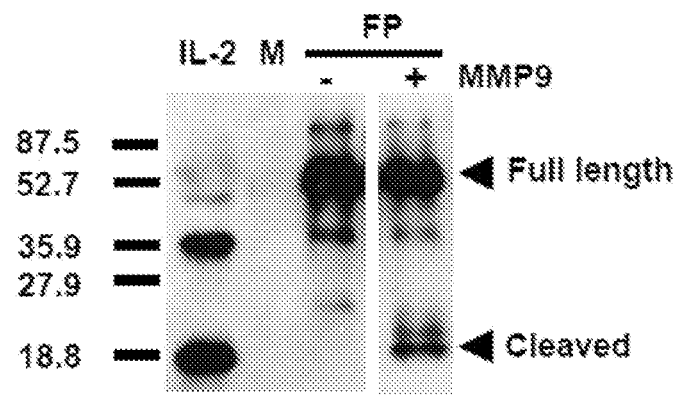
Figure 6D:
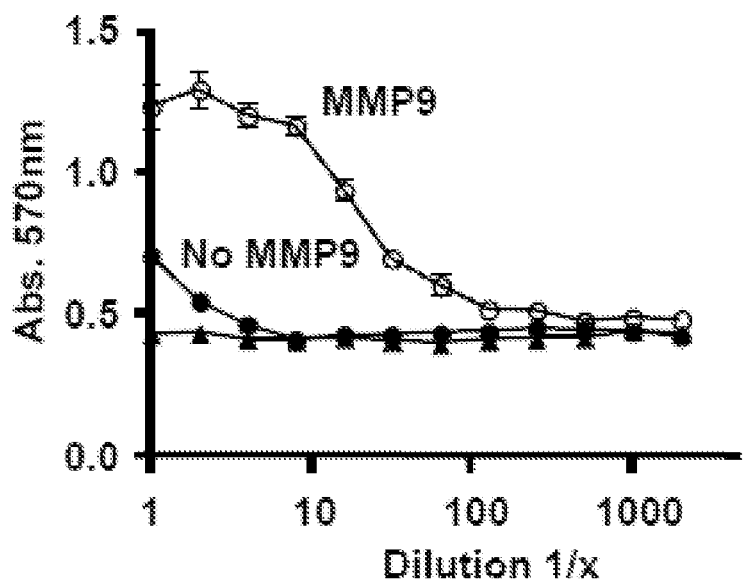
Figure 6E:
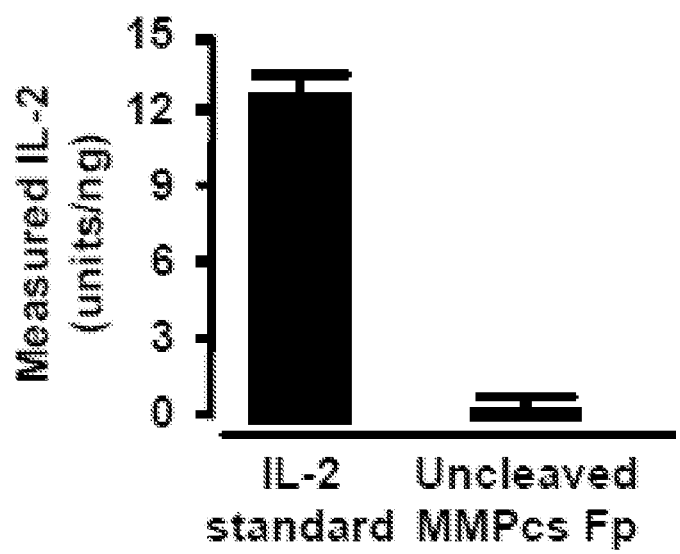

FIGS. 6A-6E show an evaluation of mouse IL-2/MMPcs/4× linker/IL-2Rα+6× His fusion proteins digested with MMP2 or MMP9. The fusion protein containing the MMP cleavage sequence was incubated with either MMP9 or MMP2 or buffer treated and the resulting material was tested by Western analysis for protein cleavage and the CTLL-2 assay for activity. FIG. 6A shows an immunoblot analysis of the fusion protein digested with MMP2 using an anti-IL-2 antibody. Bars and numbers indicate molecular weight markers. The full length and the predicted cleavage products containing IL-2 are indicated by arrowheads. Media control (M). FIG. 6B shows a graph of the fusion protein digests run in the CTLL-2 assay using equal amounts of fusion protein for the MMP2 treated or untreated fusion protein. Fusion protein plus MMP2 (○), fusion protein no treatment (●), media control (▲). FIG. 6C shows an immunoblot analyses of the fusion protein digested with MMP9 using an IL-2 antibody. Bars and numbers indicate molecular weight markers. The full length and the predicted cleavage product containing IL-2 are indicated by arrowheads. Note that the + and –MMP9 digest were run in the same gel and exposed for the same amount of time, but some intervening lanes were removed. FIG. 6D shows a graph of the fusion protein digests run in the CTLL-2 assay using equal amounts of fusion protein for the MMP9 treated or untreated fusion protein. Fusion protein plus MMP9 (○), fusion protein no treatment (●), media control (▲). In some cases error bars are not visible in CTLL-2 assay due to the size of symbols. FIG. 6E shows a graph of a CTLL-2 assay. Equal molar amounts of recombinant IL-2 standard and the untreated fusion protein were analyzed using the CTLL-2 assay, and the units/ng was calculated. Units were calculated by the dilution of the sample that gave half-maximal stimulation of the CTLL-2 cell line and represent the average and standard deviation of 6 samples. The error bars were made larger on the fusion proteins so that they are visible.

Figure 7A:
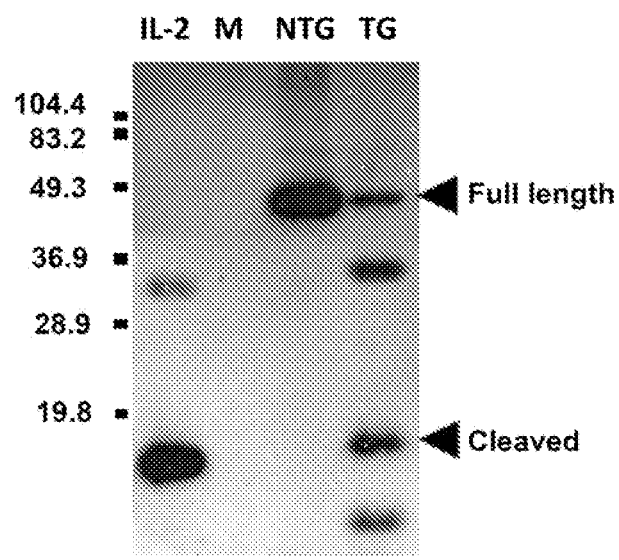
Figure 7B:
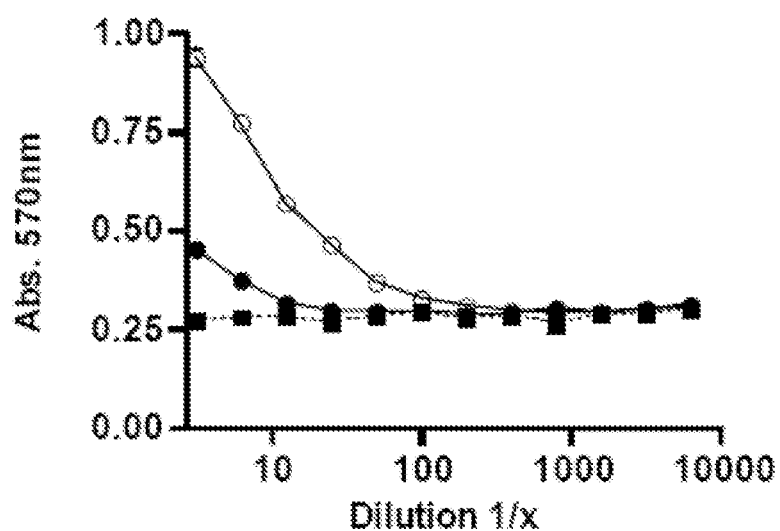

FIGS. 7A-7B shows prostate extracts from PSA transgenic mice can cleave the human IL-2/scFv-2 fusion protein and increase IL-2 bioactivity. FIG. 7A shows an image of an anti-human IL-2 immunoblot analysis of fusion protein treated with prostate extracts from PSA transgenic (TG) or nontransgenic mice (NTG) for 12 hours at 37° C. (M) indicates control media. Bars and numbers indicate molecular weight markers. Recombinant bacterially derived human IL-2 (10 ng) was used as a standard. Full-length fusion protein and the predicted cleavage fragment containing IL-2 have been denoted by arrowheads. The lowest molecular band in TG lane at ~12 kDa may represent a secondary degradation product. FIG. 7B shows a graph presenting the results of an IL-2 functional assay on aliquots of the same samples. TG extracts plus fusion protein (○), NTG extracts plus the fusion protein (●), media only (■). Equal amounts of Ni-NTA purified fusion protein loaded in first well for both conditions tested. Each point represents the average of 3 replicates. Error bars represent the standard deviation about the mean and cannot be seen in most cases because they are smaller than the symbols.

Figure 8A:
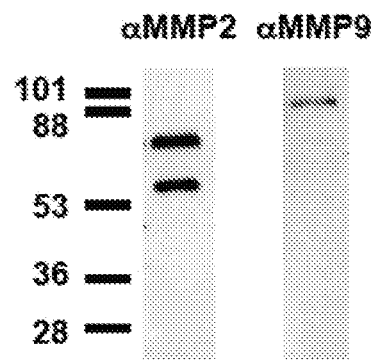
Figure 8B:
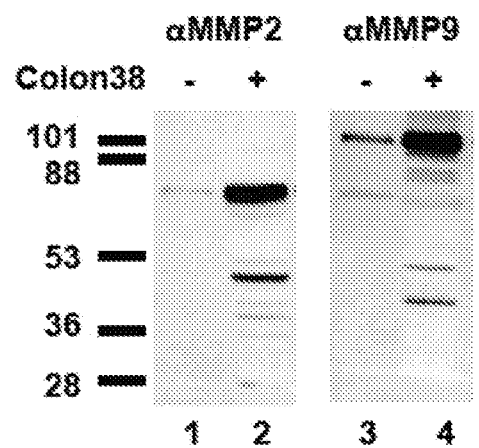
Figure 8C:
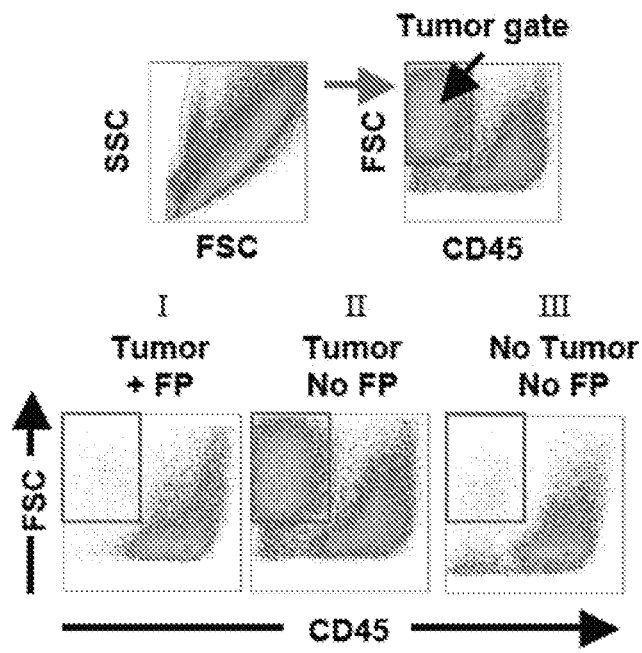
Figure 8D:
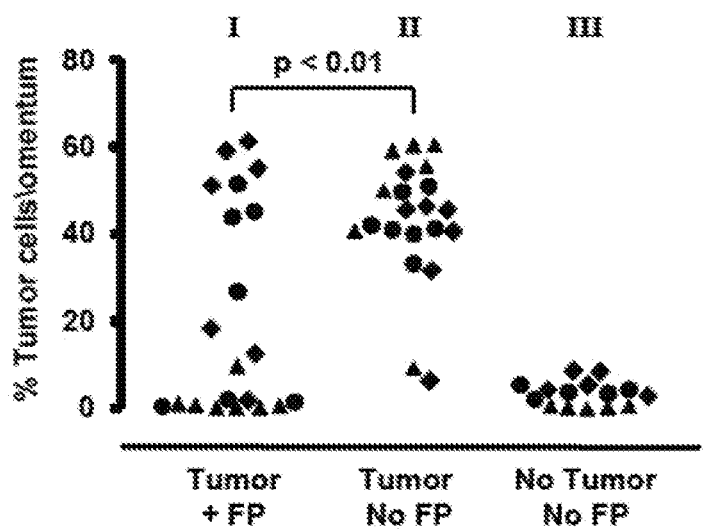
Figure 8E:
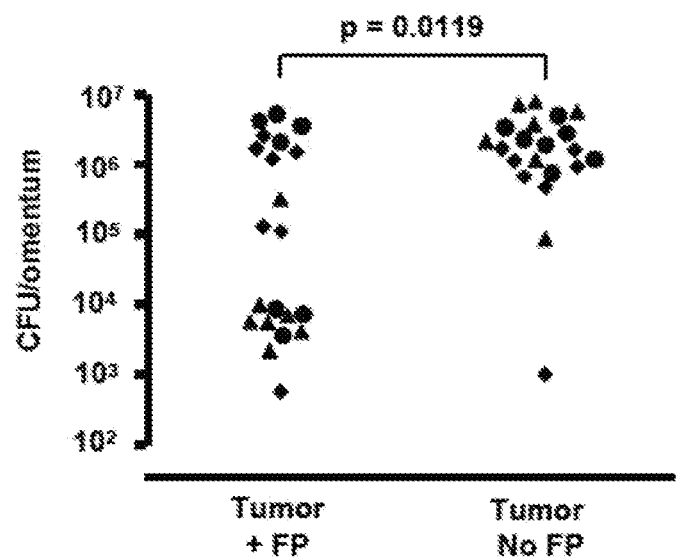

FIGS. 8A-8E show fusion protein treatment reduces Colon 38 tumor growth in vivo. FIG. 8A shows an immunoblot analyses of the in vitro expression of MMP2 and MMP9 using the Colon 38 tumor cell line. Immunoblot analyses were done on Colon 38 supernatants using the indicated antibodies. FIG. 8B shows an immunoblot analyses of the in vivo expression of MMP2 and MMP9 from omental lysates with and without Colon 38 tumor present. Lanes 1 and 2 were probed with the MMP2 antibody. Lane 1 contains omental lysates from an untreated mouse with no tumor. Lane 2 contains lysates from an omentum that had Colon 38 cells grown in vivo. Lanes 3 and 4 are replicates of lanes 1 and 2, except they were probed with a MMP9 antibody. Dashes and numbers indicate apparent molecular weights. Note lower molecular weight bands likely represent cleavage products. FIG. 8C shows the gating scheme and representative flow analyses used to identify tumor cells (high forward scatter, CD45 negative) growing in vivo on the omentum. Reconstitution experiments in which tumor cells were added to omental cells were used to establish the tumor gate which is indicated by the box. Bottom panels are examples of flow analyses of omentum from mice which received tumor and MMP fusion protein treatment (panel I: Tumor+FP), mice which had received tumor but no treatment with MMP fusion protein (panel II: Tumor, No FP), or mice which received neither tumor nor fusion protein (panel III: No Tumor, No FP). FIG. 8D shows compiled analyses of tumor cells detected on the omentum by flow cytometry. Each symbol represents an individual mouse. Different symbols indicate mice from three experiments. The P value between the indicated groups was calculated using the Kruskal-Wallis test. FIG. 8E shows the results of a colony forming assay. Viable tumor cells were determined using a colony forming assay. Symbols indicate individual mice. P value was calculated using the Mann Whitney test.

Figure 9:
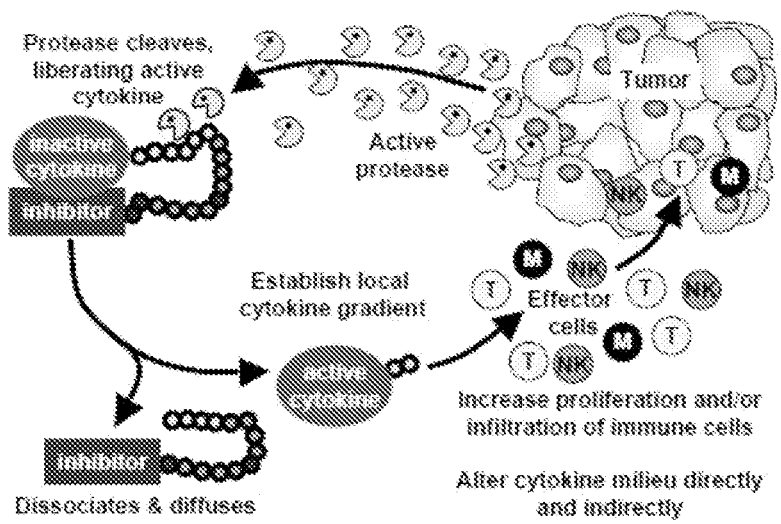

FIG. 9 shows a schematic model illustrating the general principle of the protease activated cytokine strategy and the subsequent immune effects. An active protease expressed by tumor cells cleaves the fusion protein and the cytokine is then no longer covalently bound to its inhibitor. As a result the cytokine can dissociate from its inhibitory binding moiety and thus becomes biologically active, establishing a locally high cytokine concentration gradient. In the case of IL-2, this should enhance the proliferation, survival and infiltration of immune cells such as T cells and NK cells within the tumor microenvironment. These effectors can have direct cytotoxic effects on the tumor and they may also produce additional cytokines changing the cytokine milieu thus altering the tumor microenvironment.

Figure 10:
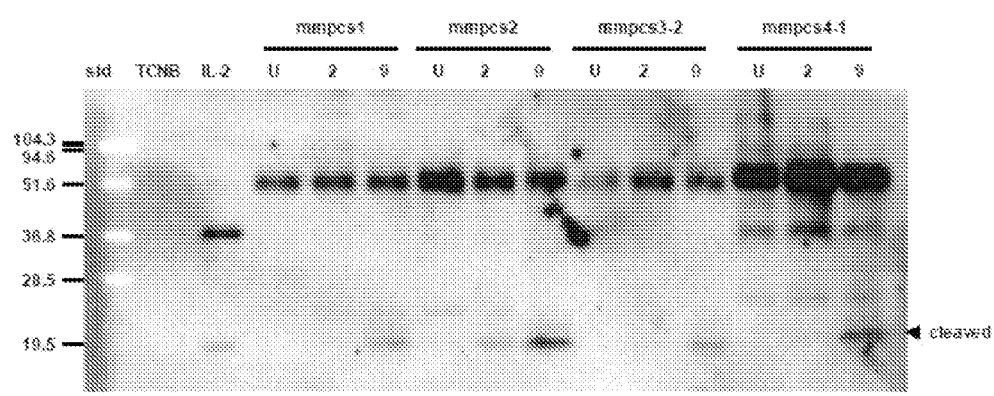

FIG. 10 shows an image of an immunoblot demonstrating that activated MMP-2 and MMP-9 cleave the mIL-2/mmpcs/ 4× linker/IL-2Rα+6His E1 purified fusion proteins. Treatment of fusion proteins with activated MMP-2 (2) and MMP-9 (9) results in a band corresponding to murine IL-2 but not in the untreated fusion protein samples (U). MMpcs1 (GPLGVRG (SEQ ID NO:2)), MMPcs2 (IPVSLRSG (SEQ ID NO:3)), MMPcs 3-2 (VPLSLYSG (SEQ ID NO:4)), and MMPcs 4-1 (SGESPAYYTA (SEQ ID NO:5)). These samples were tested for functional IL-2 activity using the IL-2 dependent cell line CTLL-2 and an increase in IL-2 function corresponded to the appearance of the IL-2 band (cleaved).

Figure 11A:
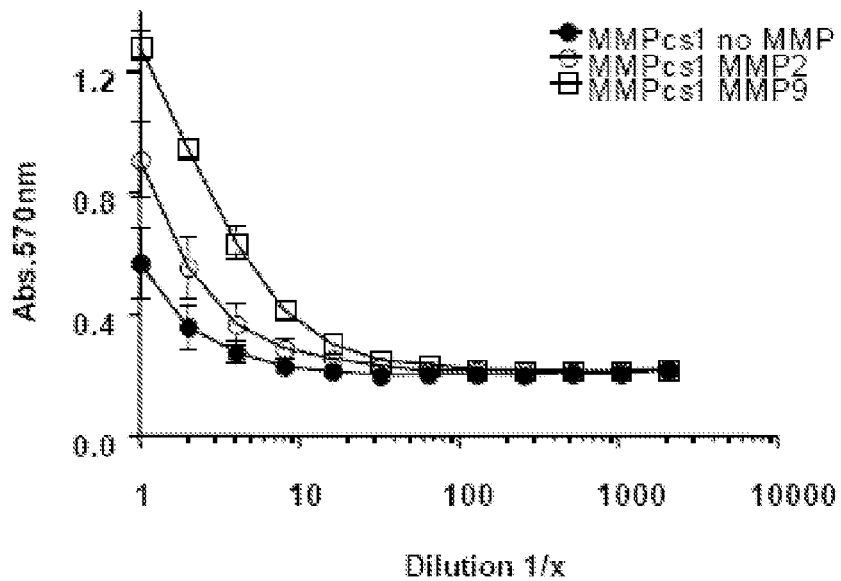
Figure 11B:
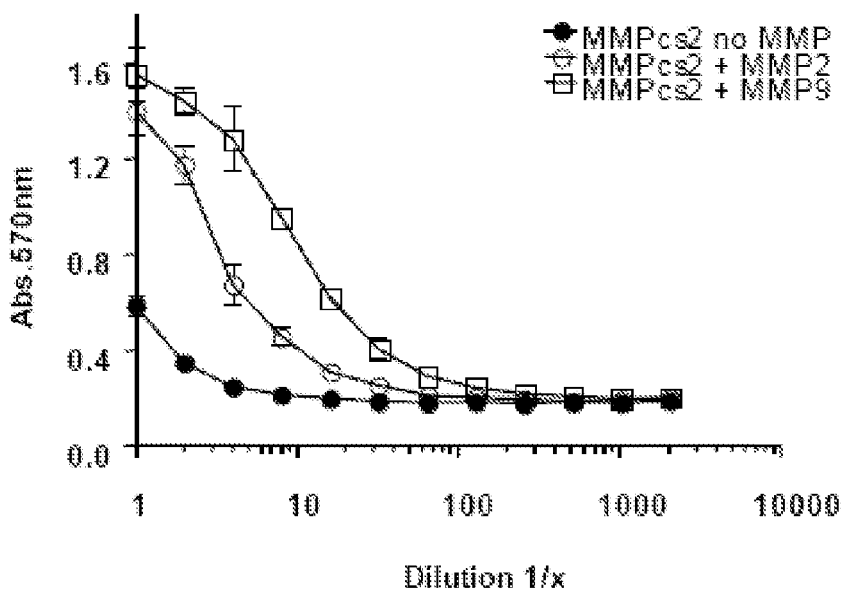
Figure 11C:
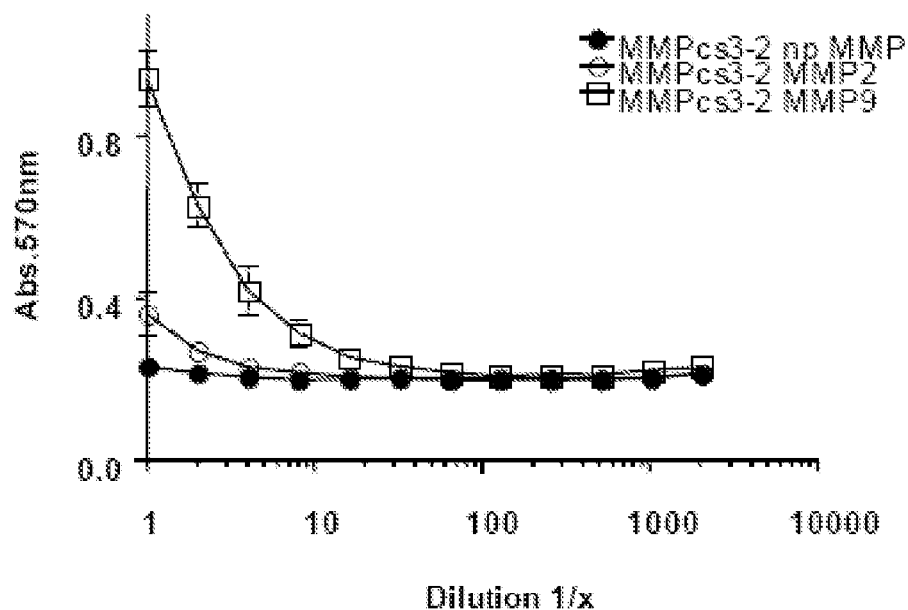
Figure 11D:
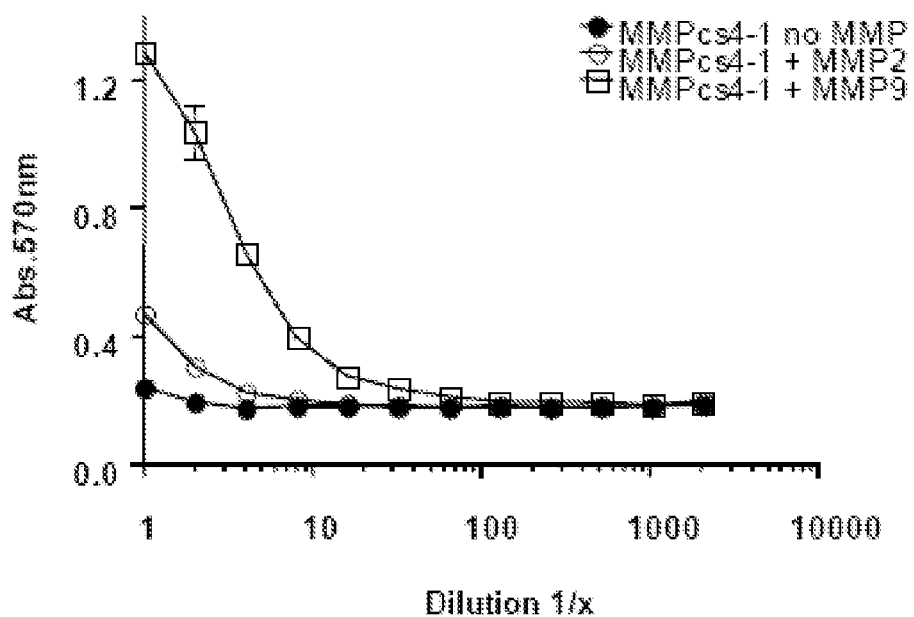

FIGS. 11A-11D show an increase in IL-2 function in the mIL-2/mmpcs/4× linker/IL-2Rα+6His purified fusion proteins treated with activated MMP-2 or MMP-9. The purified fusion proteins were untreated or treated with MMP-2 or MMP-9 for 1 hour at 37° C. FIG. 11A shows a graph demonstrating the increase in IL-2 function in the purified fusion protein with the MMPcs1 (GPLGVRG (SEQ ID NO:2)) cleavage sequence. FIG. 11B shows a graph demonstrating the increase in IL-2 function in the purified fusion protein with the MMPcs2 (IPVSLRSG (SEQ ID NO:3)) cleavage sequence. FIG. 11C shows a graph demonstrating an increase in IL-2 function in the purified fusion protein with the MMPcs 3-2 (VPLSLYSG (SEQ ID NO:4)) cleavage sequence. FIG. 11D shows a graph demonstrating the increase in IL-2 function in the purified fusion protein with the MMPcs 4-1 (SGESPAYYTA (SEQ ID NO:5)) cleavage sequence.

DETAILED DESCRIPTION

Provided herein are chimeric nucleic acid sequences encoding chimeric polypeptides. The chimeric nucleic acid sequences comprise a first nucleic acid sequence encoding an interleukin-2 (IL-2) cytokine polypeptide or a fragment thereof; a second nucleic acid sequence encoding an amino acid sequence, wherein the amino acid sequence is capable of being cleaved by a protease; and a third nucleic acid sequence encoding a polypeptide, wherein the polypeptide is capable of blocking the activity of the IL-2 cytokine polypeptide or fragment thereof.

Optionally, the second nucleic acid sequence encodes an amino acid sequence comprising HSSKLQ (SEQ ID NO:1), GPLGVRG (SEQ ID NO:2), IPVSLRSG (SEQ ID NO:3), VPLSLYSG (SEQ ID NO:4), or SGESPAYYTA (SEQ ID NO:5). The third nucleic acid can, for example, encode an alpha chain of the IL-2 receptor (IL2Rα) or a single-chain Fv (scFv) antibody fragment.

The chimeric nucleic acid sequences can further comprise a nucleic acid sequence encoding a linker sequence. The linker sequence serves to provide flexibility between the first and third polypeptides, such that the third polypeptide is capable of inhibiting the activity of the first polypeptide. The nucleic acid sequence encoding a linker sequence can be located between the first and second nucleic acid sequence or the second and third nucleic acid sequence. Optionally, the chimeric nucleic acid comprises at least one nucleic acid sequence encoding a linker sequence, two or more nucleic acid sequences encoding linker sequences, or four nucleic acid sequences encoding linker sequences. The at least one nucleic acid sequence, two or more nucleic acid sequences, or four nucleic acid sequences can encode the same or different linker sequences. Optionally, the linker sequence comprises GGGGS (SEQ ID NO:6), GSGSGS (SEQ ID NO:7), or G(SGGG)$_2$SGGT (SEQ ID NO:8). Optionally, the chimeric nucleic acid sequence further comprises a nucleic acid sequence encoding a histidine tag.

A histidine tag, as defined herein, is an amino acid sequence comprising two or more histidine residues that is added to a polypeptide for detection or purification of the polypeptide. The histidine tag can, for example, comprise six histidine residues. Optionally, the histidine tag can, for example, comprise ten histidine residues. Methods of detection or purification of a polypeptide with a histidine tag are well known in the art.

Provided herein are chimeric nucleic acid sequences encoding chimeric polypeptides. These chimeric nucleic acid sequences include all degenerate sequences related to a specific chimeric polypeptide sequence, i.e., all nucleic acids having a sequence that encodes one particular chimeric polypeptide sequence. Thus, while each particular nucleic acid sequence may not be written out herein, it is understood that each and every sequence is in fact disclosed and described herein through the disclosed chimeric polypeptide sequences.

Also provided are chimeric polypeptides. The chimeric polypeptides comprise a first polypeptide comprising an interleukin-2 (IL-2) cytokine polypeptide or a fragment thereof; a second polypeptide comprising an amino acid sequence, wherein the amino acid sequence is capable of being cleaved by a protease; and a third polypeptide comprising a polypeptide, wherein the polypeptide is capable of blocking the activity of the IL-2 cytokine polypeptide or fragment thereof. The third polypeptide can, for example, block the activity of the IL-2 cytokine or fragment thereof by binding the IL-2 cytokine or fragment thereof.

Optionally, the second polypeptide comprises HSSKLQ (SEQ ID NO:1), GPLGVRG (SEQ ID NO:2), IPVSLRSG (SEQ ID NO:3), VPLSLYSG (SEQ ID NO:4), or SGESPAYYTA (SEQ ID NO:5). The third polypeptide can, for example, comprise an alpha chain of IL-2 receptor (IL-2Rα) or a single-chain Fv (scFv) antibody fragment.

The chimeric polypeptide can further comprise a linker sequence. The linker sequence serves to provide flexibility between the first and third polypeptides, such that the third polypeptide is capable of inhibiting the activity of the first polypeptide. The linker sequence can be located between the first and second polypeptide or the second and third polypeptide. Optionally, the chimeric polypeptide comprises at least one linker sequence, two or more linker sequences, or four linker sequences. The at least one linker sequence, two or more linker sequences, or four linker sequences can be the same or different linker sequences. Optionally, the linker sequence comprises GGGGS (SEQ ID NO:6), GSGSGS (SEQ ID NO:7), or $G(SGGG)_2SGGT$ (SEQ ID NO:8). The chimeric polypeptide can further comprise an amino acid sequence comprising a histidine tag.

Proteases capable of cleaving amino acid sequences encoded by the chimeric nucleic acid sequences provided herein or the chimeric polypeptides herein can, for example, be selected from the group consisting of a prostate specific antigen (PSA), a matrix metalloproteinase (MMP), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Provided herein are chimeric polypeptides. As with all peptides, polypeptides, and proteins, including fragments thereof, it is understood that additional modifications in the amino acid sequence of the chimeric polypeptides can occur that do not alter the nature or function of the peptides, polypeptides, or proteins. Such modifications include conservative amino acid substitutions and are discussed in greater detail below.

The chimeric polypeptides provided herein have a desired function. The chimeric polypeptides are comprised of at least a first, second, and third polypeptide. The first polypeptide, e.g., IL-2, is provided to be an active agent. The second polypeptide, the protease cleavable polypeptide, is provided to be cleaved by a protease that is specifically expressed at the intended target of the active agent. The third polypeptide, e.g., the alpha chain of the IL-2 receptor (IL-2Rα) or the single chain Fv (scFv) antibody fragment, is provided to be a blocking agent. The third polypeptide serves to block the activity of the first polypeptide. Optionally, the third polypeptide blocks the activity of the first polypeptide by binding the first polypeptide. Optionally, the third polypeptide can be the active agent. For example, a chimeric polypeptide comprising a peptide mimetic that binds a scFv with low affinity, a protease cleavable polypeptide, and a scFv can be made. The scFv has a high affinity for a biologic, such as IL-2; however, due to the close proximity, the scFv is blocked by the peptide mimetic with low affinity. Upon cleavage by the protease, the peptide mimetic is released, allowing the scFv to act on its original target, IL-2, thus making the third polypeptide the active agent.

The polypeptides described herein can be further modified so long as the desired function is maintained. It is understood that one way to define any known modifications and derivatives or those that might arise, of the disclosed genes and proteins herein is through defining the modifications and derivatives in terms of identity to specific known sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides or chimeric nucleic acids provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to one of SEQ ID NOs:1-50. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g, by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the CDRs. Such random mutations can be introduced using a variety of techniques, including radiation, chemical mutagens or error-prone PCR. Multiple rounds of mutation and selection can be performed using, for example, phage display.

Further provided are methods of treating a subject with or at risk of developing a cancer. The methods comprise selecting a subject with or at risk of developing a cancer; and administering to the subject an effective amount of a chimeric polypeptide. The chimeric polypeptide comprises a first polypeptide comprising an interleukin-2 (IL-2) cytokine polypeptide or a fragment thereof; a second polypeptide comprising an amino acid sequence, wherein the amino acid sequence is capable of being cleaved by a protease expressed in the cancer; and a third polypeptide comprising a polypeptide, wherein the polypeptide is capable of blocking the activity of the IL-2 cytokine polypeptide or fragment thereof. The cancer can, for example, be selected from the group consisting of prostate cancer, lung cancer, colon cancer, breast cancer, skin cancer, and brain cancer.

Optionally, the second polypeptide comprises HSSKLQ (SEQ ID NO:1), GPLGVRG (SEQ ID NO:2), IPVSLRSG (SEQ ID NO:3), VPLSLYSG (SEQ ID NO:4), or SGESPAYYTA (SEQ ID NO:5). The third polypeptide can, for example, comprise an alpha chain of IL-2 receptor (IL-2Rα) or a single-chain Fv (scFv) antibody fragment.

The chimeric polypeptide can further comprise a linker sequence. The linker sequence serves to provide flexibility between the first and third polypeptides, such that the third polypeptide is capable of inhibiting the activity of the first polypeptide. The linker sequence can be located between the first and second polypeptide or the second and third polypeptide. Optionally, the chimeric polypeptide comprises at least one linker sequence, two or more linker sequences, or four linker sequences. The at least one linker sequence, two or more linker sequences, or four linker sequences can be the same or different linker sequences. Optionally, the linker sequence comprises GGGGS (SEQ ID NO:6), GSGSGS (SEQ ID NO:7), or G(SGGG)$_2$SGGT (SEQ ID NO:8). The chimeric polypeptide can further comprise an amino acid sequence comprising a histidine tag.

Further provided herein are methods of treating infections in a subject. The chimeric polypeptides provided herein can, for example, be designed to treat bacterial or viral infections (e.g., infections caused by *Pseudomonas* or infections with the Human Immunodeficiency Virus (HIV)). The infectious agents can express particular proteases. The chimeric polypeptides can be designed to contain a first polypeptide that serves as the active agent to treat the infection, a second polypeptide that is cleavable by a protease expressed by the infectious agent, and a third polypeptide that serves as a blocking agent by blocking the activity of the first polypeptide. The cleavage of the second polypeptide by the protease expressed by the infectious agent results in an increase in activity of the first polypeptide at the site of infection, thus, treating the infection locally. Treating an infection locally can minimize any side effects of the active agent in areas where there is no active infection.

Provided herein are methods of treating a subject with or at risk of developing a cancer or with or at risk of developing an infection. Such methods include administering an effective amount of a chimeric polypeptide. The chimeric polypeptide can be administered as a polypeptide or as a chimeric nucleic acid sequence encoding the chimeric polypeptide. Optionally, the chimeric polypeptides or chimeric nucleic acid sequences encoding the chimeric polypeptides are contained within a pharmaceutical composition.

Provided herein are compositions containing the chimeric polypeptides or chimeric nucleic acid sequences encoding the chimeric polypeptides and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism. For example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or infection) or during early onset (e.g., upon initial signs and symptoms of cancer or infection). Prophylactic administration can occur for several days to years prior to the manifestation of symptoms of cancer or infection. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or infection.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

General Methods

Mice.

C57BL/6J mice were purchased from the Jackson Laboratory (Bar Harbor, Me.). Human PSA transgenic mice were backcrossed onto the C57BL/6J background and were used as a source of PSA expressing prostate tissue (Wei et al., Proc. Natl. Acad. Sci. USA 94:6369-74 (1997).

Construction of the Mouse IL-2/Mip-1α Fusion Proteins.

Plasmids were constructed using a combination of PCR and standard molecular biology cloning techniques. The details of the primers used are presented in Table 2. In brief, the mouse IL-2/Mip1α fusion protein was derived from the mouse IL-2 containing plasmid pMUT-1 (ATCC; Manassas, Va.). The IL-2 cDNA was PCR amplified using a reverse primer encoding the PSA cleavage sequence (PSAcs) (HSSKLQ) (SEQ ID NO:1) and an EcoRI restriction site and a forward primer containing a SalI restriction site. This product was then cloned into the pBluescript II KS⁻ plasmid (Stratagene; La Jolla, Calif.). The Mip-1α portion of the fusion protein was PCR amplified using the pCLXSN parental plasmid containing Mip-1α (van Deventer et al., J. Immunol. 169:1634-9 (2002)) using primers to omit the Mip-1α leader sequence and add the EcoRI and BamHI restriction sites (Table 2). This was subsequently cloned into the EcoRI and BamHI sites of the pBluescript plasmid containing the mouse IL-2 and the PSA cleavage site. This plasmid was then verified by sequencing and subsequently cloned into pcDNA3.1 (Invitrogen; Carlsbad, Calif.) using the XhoI and BamHI restriction sites to obtain flanking restriction enzyme sites so that it could be shuttled into pVL1392 for expression in the BD BaculoGold™ transfer vector system (BD Biosciences; San Jose, Calif.) using the XbaI and BamHI sites.

TABLE 2

PCR primers for construction of fusion proteins.

| Construct | Primer Sequences |
|---|---|
| Mouse IL-2 (F) | 5'-CATAGGTCGACATGTACAGCATGCAGCTCGCATCC-3' (SEQ ID NO: 51) |
| (PSAcs Rev) | 5'-CATAGGGAATTCCTGCAGCTTGCTGCTGTGTTGAGGGCTTGTTGAGATGATGCT-3' (SEQ ID NO: 52) |
| (MMPcs Rev) | 5'-CCGCGCGAATTCACCTCTGACACCCAGAGGACCTTGAGGGCTTGTTGAGATGATGCT-3' (SEQ ID NO: 53) |
| Mouse MIP-1α (F) | 5'-CATAGGGAATTCGCGCCATATGGAGCTGACAC-3' (SEQ ID NO: 54) |
| (Rev) | 5'-CCTATGGGATCCGGCATTCAGTTCCAGGTCAG-3' (SEQ ID NO: 55) |
| Mouse IL-2Rα (F) | 5'-GCGCGGGTACCGAACTGTGTCTGTATGACCCACCC-3' (SEQ ID NO: 56) |
| (Rev) | 5'-CGGCCGGATCCTCATTATGCTACCTTATACTCCATTGT-3' (SEQ ID NO: 57) |
| (Rev) | 5'-CGGCCGGATCCTCATTAGTGGTGGTGGTGGTGGTGCTACCTTATACTCCATTGT-3' (SEQ ID NO: 58) |
| Human IL-2 (F) | 5'-GATACGTCGACATGTACAGGATGCAACTCCTG-3' (SEQ ID NO: 59) |
| (Rev) | 5'-TCGGAGAATTCCTGCAGCTTGCTGCTGTGAGTCAGTGTTGAGATGATGCT-3' (SEQ ID NO: 60) |

TABLE 2-continued

PCR primers for construction of fusion proteins.

| Construct | Primer Sequences |
|---|---|
| Linker Oligos (F) (Rev) | 5'-GGCCGGAATTCGGTGGCGGTGGCTCTGGTGGCGGTGGCTCTGGTGGCG GTGGCTCT-3' (SEQ ID NO: 61)<br>5'-GCGGGTACCAGAGCCACCGCCACCAGAGCCACCGCCACCAGAGCCAC CGCCACCAGAGCC-3' (SEQ ID NO: 62) |
| External primers | |
| Human scFv (F) (Rev) (Rev + 6His) | 5'-GCGCGGGTACCCAGTCTGTGCTGACTCAGCCA-3' (SEQ ID NO: 63)<br>5'-CCGGCGGATCCTGAGGAGACGGTGACCAGGGT-3' (SEQ ID NO: 64)<br>5'-CCGGCGGATCCGTGGTGGTGGTGGTGTGAGGAGACCAGGGT-3' (SEQ ID NO: 65) |
| Primers to insert stop codons and Not I site | |
| (F) | 5'-GCGCCGCGGCCGCGTCGACATGTACAGGATGCAACTC-3' (SEQ ID NO: 66) |
| (Rev) | 5'-GGCGCGGATCCTCATTATGAGGAGACGGTGACCAGGGTGCC-3' (SEQ ID NO: 67) |
| (Rev + 6His) | 5'-CGCGCGGATCCTCATTAGTGGTGGTGGTGGTGTGAGGAGACGGT GACCAGGGT-3' (SEQ ID NO: 68) |

F: forward, Rev: reverse; PSAcs: PSA protease cleavage sequence; MMPcs: Matrix metalloproteinase cleavage sequence; His: Histidine Construction of the Mouse IL-2/IL-2Rα Fusion Protein.

IL-2Rα in pcEVX-3 was PCR amplified using primers (Table 2) to add the KpnI and BamHI restriction sites, remove the hydrophobic transmembrane region, and for some constructs, addition of a 6× Histidine tag. This product was cloned into pBluescript (pBluescript IL-2Rα). The (GGGGS)$_x$ (SEQ ID NO:6) linker of various repeat lengths was either synthesized (GENEART Inc.; Toronto, ON, Canada) or was made by annealing primers from complimentary oligonucleotides (Table 1) and then cloned into pBluescript using the EcoRI and KpnI restriction sites. The (GGGGS)$_x$ (SEQ ID NO:6) linker was excised and cloned into the pBluescript IL-2Rα plasmid. The linker and IL-2Rα were excised using the EcoRI and BamHI sites and directionally cloned into the pBluescript IL-2/PSAcs plasmid containing murine IL-2 and the PSA cleavage sequence (HSSKLQ) (SEQ ID NO:1) resulting in the pBluescript IL-2/PSAcs/linker/IL-2Rα plasmid. This insert was then shuttled to pcDNA 3.1 and cloned into pVL1392 as described above.

Construction of Mouse IL-2/MMPcs/IL-2Rα Fusion Protein.

To change the cleavage sequence from HSSKLQ (SEQ ID NO:1) (PSAcs) to SGESPAYYTA (SEQ ID NO:5) (MMPcs) the pBluescript plasmid containing the mouse IL-2 and the PSAcs portion of the fusion protein was linearized using NotI and PCR was performed using the IL-2 forward primer and the MMPcs reverse primer (Table 2). This PCR product was then digested with SalI and EcoRI restriction endonucleases and cloned into pBluescript to create the pBluescript IL-2/MMPcs plasmid. The pVL1392 vector containing the mouse IL-2/PSAcs/(GGGGS)$_4$/IL-2Rα+6× His fusion protein was digested with EcoRI and BamHI and the fragment containing the (GGGGS)$_4$ (SEQ ID NO:10) linker and IL-2Rα was isolated and cloned into the pBluescript IL-2/MMPcs plasmid using the EcoRI and BamHI sites. The fragment encoding the entire fusion protein was then shuttled into pcDNA3.1 using the XhoI and BamHI sites and subsequently shuttled into pVL1392 using XbaI and BamHI for expression. All constructs made are listed below in Table 3.

TABLE 3

Summary of IL-2 fusion protein constructs.

Mouse Fusion Protein Constructs

*PSA Fusion Proteins* mIL-2/PSAcs/2x linker/mIL-2Rα
mIL-2/PSAcs/2x linker/mIL-2Rα + 6His
mIL-2/PSAcs/4x linker/mIL-2Rα
mIL-2/PSAcs/4x linker/mIL-2Rα + 6His

*MMP Fusion Proteins* mIL-2/MMP1cs/4x linker/mIL-2Rα + 6His
mIL-2/MMP2cs/4x linker/mIL-2Rα + 6His
mIL-2/MMP3-2cs/4x linker/mIL-2Rα + 6His
mIL-2/MMP4-1cs/4x linker/mIL-2Rα + 6His

Human Fusion Protein Constructs

*PSA Fusion Proteins* hIL-2/PSAcs/2x linker/hIL-2Rα (A)
hIL-2/PSAcs/3x linker/hIL-2Rα (A)
hIL-2/PSAcs/3x linker/hIL-2Rα + 6His (A)
hIL-2/PSAcs/3x linker/hIL-2Rα (B)
hIL-2/PSAcs/3x linker/hIL-2Rα + 6His (B)
hIL-2/PSAcs/5x linker/hIL-2Rα (B)
hIL-2/PSAcs/2x linker/scFv
hIL-2/PSAcs/2x linker/scFv + 6His
hIL-2/PSAcs/3x linker/scFv
hIL-2/PSAcs/3x linker/scFv + 6His
hIL-2/PSAcs/4x linker/scFv
hIL-2/PSAcs/4x linker/scFv + 6His IL-2: Interleukin 2; PSA: Prostate Specific Antigen; cs: cleavage sequence; IL-2Rα: alpha chain of IL-2 receptor; MMP: matrix metalloproteinase; His: Histidine; scFv: single chain fragment of antibody.
Two putative forms of the soluble hIL-2Rα: (A) = hIL-2Rα ends at amino acid glutamine 219; (B) = hIL-2Rα ends at amino acid alanine 221.

Use of Human Phage Display Library to Identify and Characterize Human IL-2 Reactive scFv.

A human phage display library constructed from peripheral blood lymphocytes was used to screen for phage expressing single chain fragments of antibodies capable of binding to human IL-2 on their surface (phscFvs). The library was generated in the pAP-III6 vector, (Haidaris et al., J. Immunol. Methods 257:185-202 (2001); Malone and Sullivan, J. Mol. Recognit. 9:738-45 (1996)) a monovalent display vector, by PCR amplification of VL and VH immunoglobulin domains from peripheral blood lymphocyte cDNA prepared from approximately 100 donors. The variable regions were PCR amplified with primers that encode a 14 amino acid linker between the VL and VH domains, and then cloned into pAP-III6. The library consists of approximately $2 \times 10^9$ independent transformants and was screened using a modified ELISA assay basically as described (Haidaris et al., J. Immunol. Methods 257:185-202 (2001)) using recombinant human IL-2 (Peprotech; Rocky Hill, N.J.) adsorbed to plates as the target antigen. After several rounds of phage panning purification, a small panel of phage expressing scFv (phscFv) was tested for the ability to bind human IL-2 in the presence of a neutralizing anti-human IL-2 monoclonal antibody (eBioscience; San Diego, Calif.). A recombinant form of a *P. falciparum* protein (accession number XM_001347271) and the phscFv SGPP that reacts with it (Mehlin et al., Mol. Biochem. Parasitol. 148:144-60 (2006)), was used as a control to check for specificity of inhibition with the anti-human IL-2 neutralizing antibody. In brief, 0.5n/ml of human IL-2 or SGPP in PBS were used to coat the ELISA plate, the wells were washed and 2 μg/ml anti-human IL-2 neutralizing antibody (MQ1-17H12) (eBioscience) or blocking buffer was added. Supernatants containing individual phscFv clones were then added and phage binding was detected using an anti-M13 phage HRP-conjugated antibody (GE Healthcare; Buckinghamshire, UK). The ELISA plate was developed by adding 50 μl O-phenylenediamine (OPD) (Sigma-Aldrich; St. Louis, Mo.) in 0.1M Citrate pH 4.5 and 0.04% $H_2O_2$, stopped by adding 50 μl/well 2N $H_2SO_4$ and the absorbance was read at 490 nm. The DNA from phscFv-2 was isolated and used as the starting material for the construction of the scFv human IL-2 fusion construct.

Construction of the Human IL-2/Human scFv Fusion Protein.

The human IL-2 cDNA in pBR322 (ATCC) was PCR amplified using primers (Table 2) which added an amino terminal SalI site, the PSAcs (HSSKLQ) (SEQ ID NO:1) and a carboxyl terminal EcoRI restriction site. This insert was then directionally cloned into pBluescript (Stratagene) using the SalI and EcoRI restriction sites. The $(GGGGS)_x$ (SEQ ID NO:6) linker of various repeat lengths (as described earlier) was cloned into pBluescript using the EcoRI and KpnI restriction sites. The human IL-2 scFv was PCR amplified (Table 2) from the M13 phage DNA from the phage clone scFv-2 and the 6× His tag and the Kpn I and BamHI restriction sites were added. This insert was then cloned into the pBluescript Kpn I minus plasmid containing the human IL-2/PSAcs/linker using the Kpn I and Bam HI sites. Then an external Not I site, stop codons, and a Bam HI site were added by PCR, and the entire fusion protein was subsequently cloned into pVL1392 using the Not I and Bam HI sites.

Virus Production of Fusion Protein.

The generation of recombinant baculoviruses for expression of proteins in insect cells have been described previously (Rose et al., J. Gen. Virol. 75:2445-9 (1994); Rose et al., J. Gen. Virol. 71:2725-9 (1990)). Recombinant viruses were created using the pVL1392 transfer vector and the BD BaculoGold™ transfer vector system (BD Biosciences) as described by the manufacturer. Initial virus production was performed in *Spodoptera frugiperda* (Sf-9) cells cultured in Sf-900 II SFM media (Gibco®/Invitrogen; Carlsbad, Calif.) and after several passages a high titer stock was obtained. For final production of fusion proteins, *Trichoplusia ni* (*T. ni.*) cells (Invitrogen) cultured in Express Five® SFM media (Gibco®/Invitrogen) plus 2 mM L-Glutamine High Five™ were propagated in 300 ml shaking cultures in 1 L flasks (125 RPM, 27° C.) and were infected with the high titer stock and incubated with shaking for 72 hours at 27° C. The supernatant was used directly after clarification in some experiments, or in some cases, the fusion proteins were purified via the 6× Histidine tag using Nickel-NTA agarose beads (Qiagen; Valencia, Calif.) and Poly-Prep® Chromatography columns (BioRad; Hercules, Calif.) using the manufacturer's recommendations.

Detection of Mouse IL-2 and IL-2Rα in Fusion Proteins by ELISA.

IL-2 or the IL-2Rα chain was detected using either the anti-IL-2 monoclonal (JES6-1A12) (BD Pharmingen; San Jose, Calif.) or the anti-mouse IL-2Rα monoclonal (PC61) antibodies (BD Pharmingen). Wells of a 96-well plate were coated with either antibody (2.5 μg/ml) in PBS. Wells were blocked with 5% non-fat milk in PBS with 0.2% Tween (PBS-M-Tw) and fusion proteins were added for 1-2 hours at 37° C. After washing, an anti-mouse IL-2 biotin-labeled antibody (JES5H4) (BD Pharmingen) was added and binding was detected using Strepavidin HRP (Southern Biotechnology Associates; Birmingham, Ala.). The ELISA plate was developed by adding 50 μl O-phenylenediamine (OPD) (Sigma-Aldrich) in 0.1M Citrate pH 4.5 and 0.04% $H_2O_2$, stopped by adding 50 μl/well 2N $H_2SO_4$ and the absorbance was read at 490 nm.

Mouse IL-2, IL-2Rα and 6× Histidine Immunoblot Analyses.

Immunoblot analyses were performed as reported previously with minor modifications (Turner et al., J. Immunol. Methods 256:107-19 (2001)). The following monoclonal antibodies were used: rat anti-mouse IL-2 antibody (JES6-1A12) (BD Pharmingen), rat anti-mouse IL-2Rα (PC61) (BD Pharmingen), and mouse anti-6× His monoclonal antibody (MM5-156P) (Covance; Princeton, N.J.). Detection was done using a goat anti-rat HRP conjugated antibody (Jackson Immuno Research; West Grove, Pa.) and developed using the Amersham ECL Plus western blotting detection reagent (GE Healthcare) using the manufacturer's recommendations. A determination of fusion protein concentration was established using immunoblot analyses and quantitative densitometry and compared to recombinant IL-2. For MMP immunoblot analyses, extracts or supernatants were probed with goat anti-mouse-MMP2 or MMP9 antibodies (R & D Systems, Minneapolis, Minn.).

In Vitro Digestion Conditions for Fusion Proteins.

Fusion proteins were digested with PSA (Cortex Biochem; San Leandro, Calif.) in 50 mM Tris, 100 mM NaCl pH 7.8 at 37° C. For digestion of the fusion protein containing the MMP cleavage sequence, MMP9 or MMP2 (R & D Systems) was activated with p-aminophenylmercuric acetate (APMA) and this activated protease or equivalent amount of activating solution without the protease was used to digest the fusion protein for one hour at 37° C. for MMP9 and 10 minutes for MMP2. Aliquots of digests were loaded on 15% Laemmli gels for western analysis. The rat anti-mouse IL-2 primary antibody (JES6-1A12) (BD Pharmingen) and goat anti-rat HRP conjugated secondary antibody (Jackson Immuno Research) were used and blots were developed as described above. Aliquots of digests were also used in the IL-2 functional assay described below.

IL-2 Functional Assay.

Functional IL-2 measured using CTLL-2 cells (ATCC) as described (Mosmann, J. Immunol. Methods 65:55-63 (1983)) with minor modifications. In brief, digested samples were serially diluted 1:2, then 50 μl of test supernatant was added to $3.5-5.0 \times 10^4$ CTLL-2 cells/well in 100 μl of media in a 96-well plate and incubated at 37° C. in 5% $CO_2$ for 18-22 hours. Then 75n/well Thiazolyl Blue Tetrazolium Bromide (MTT) (Sigma-Aldrich) was added and the plate was incubated for 8 hours at 37° C. in 5% $CO_2$. Cells were lysed with 100 μl/well 10% SDS (Gibco®/Invitrogen) acidified with HCl, incubated at 37° C. in 5% $CO_2$ overnight, and absorbance 570 nm was read (Young et al., Toxicol In Vitro 19:1051-9 (2005)). Recombinant human IL-2 standard (Peprotech) was serially diluted with 0.5 ng delivered to CTLL-2 cells in the first well.

Prostate Explant Cultures and Preparation of Prostate Extracts.

Ventral prostates from wild type C57BL/6J (Jackson) (NTG) and PSA transgenic C57BL/6J (TG) mice were surgically removed and placed in 600 μl DMEM media (Gibco®/Invitrogen) supplemented with 0.005 mg/ml bovine insulin (Sigma-Aldrich), 10 nM trans-Dehydroandrosterone (Sigma-Aldrich), 5% fetal calf serum (Hyclone; Logan Utah), 5% Nu-serum IV (BD Biosciences), and 0.05% penicillin/streptomycin (Sigma-Aldrich). Fusion protein was added to explant culture and incubated at 37° C. in 5% $CO_2$ and 100 μl aliquots were removed at 1, 12, 24 and 48 hours and stored at −20° C. for use. Prostate extracts were made using ventral prostates homogenized in a Dounce homogenizer in 100 μl of 50 mM Tris, 100 mM NaCl pH 7.8. Extracts were centrifuged to remove debris and the supernatants stored at −20° C. Total protein concentration was determined using the Bio Rad Protein Assay (Bio Rad) according to the manufacturer's recommendation and equal amounts of protein extracts were used for fusion protein digestions described earlier. PSA in culture supernatants or in the prostate extracts was detected using a capture ELISA as described previously (Fisher et al., Prostate 51:153-65 (2002)) with minor modifications.

Detection of Human IL-2 by Immunoblot Analyses.

Human IL-2 was detected by standard western technique using a rabbit anti-human IL-2 antibody (Leinco; St. Louis, Mo.) (1.0 μg/ml) in TBS-M-Tw followed by a goat anti-rabbit HRP conjugated antibody (Leinco) (0.2 μg/ml) in TBS-M-Tw. The blot was developed using the Amersham ECL Plus western blotting detection system (GE Healthcare) according to manufacturer's recommendations.

Tumor Growth Experiments.

For the tumor growth experiments, $5 \times 10^5$ Colon 38 cells were injected intraperitoneally into syngeneic mice and allowed to attach for 24 hours. Groups of mice were treated daily for 6 days with fusion protein, treated with vehicle, or untreated as indicated in the description of figures. On day 7, the animals were sacrificed, omenta removed and treated with collagenase. The collagenase-treated samples were stained for flow cytometry, as described with minor modifications (Sorenson et al., Immunol Res. (2009)). Preliminary experiments were performed using normal omental cells, tumor cells and a reconstructed mixture of tumor cells, and omental cells to establish the gates shown. Colony forming assays were performed as previously described (Lord and Burkhardt, Cell Immunol. 85:340-50 (1984)). Statistical analyses testing for significance were performed as indicated.

Example 1

Construction of Cleavable Fusion Proteins

Figure 1B:
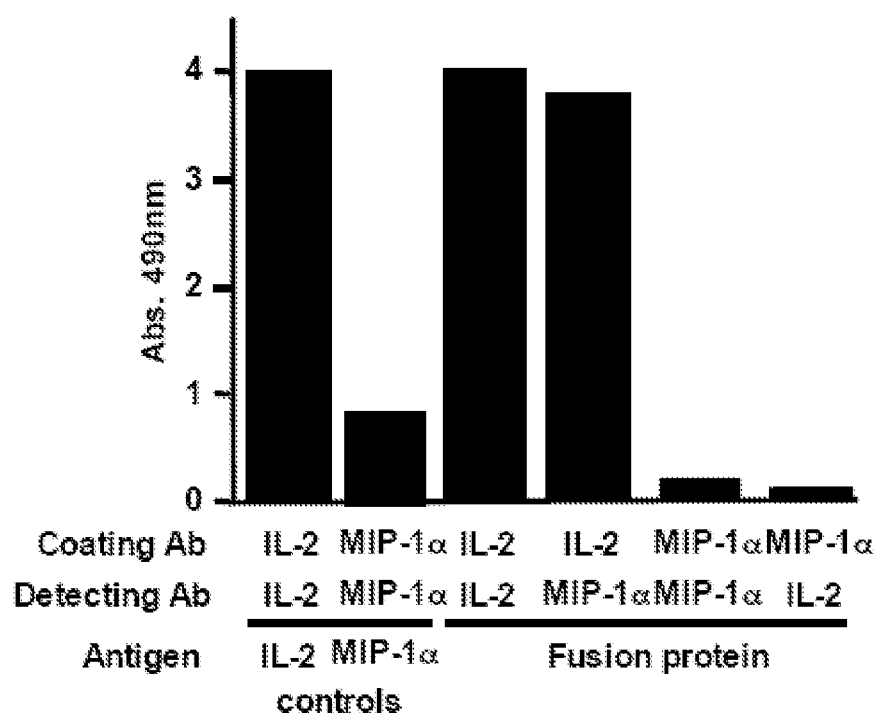
Figure 1C:
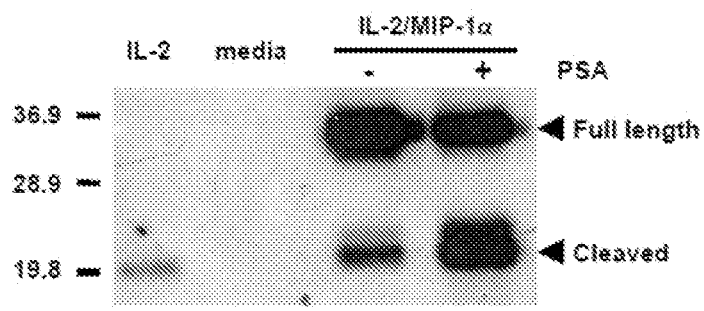
Figure 1D:
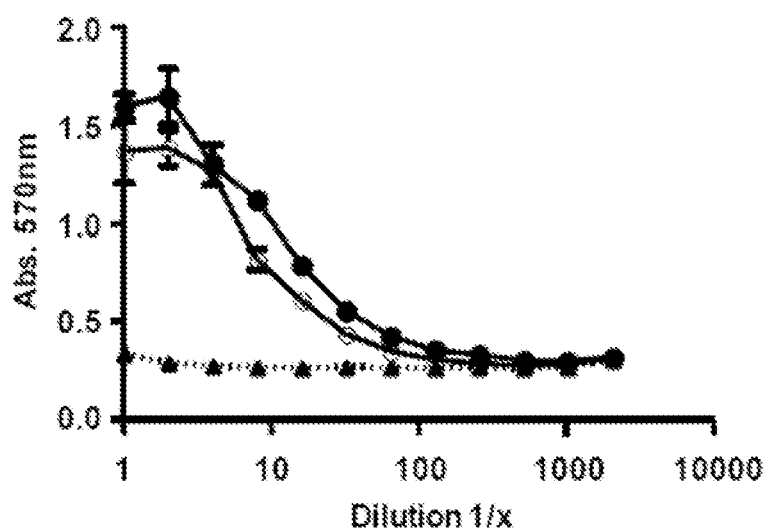

The initial strategy employed to create a cytokine fusion protein that could be cleaved by a tumor cell expressed protease was based on steric hindrance, and used two biologically active molecules (specifically the cytokine IL-2 and the inflammatory chemokine Macrophage inflammatory protein 1 alpha (Mip1α)) separated by a very short peptide sequence recognized by the prostate specific protease PSA (Denmeade et al., Cancer Res. 57:4924-30 (1997)). It was hypothesized that the immunomodulatory proteins would be largely inactive in the fusion protein owing to their close proximity but would become more active if the fusion protein could be successfully cleaved, thereby separating the two proteins. An IL-2/Mip1α construct was made and expressed in insect cells using the baculovirus system (FIG. 1A). A capture antibody ELISA revealed that some of the epitopes of Mip1-α in the fusion protein were inaccessible, suggesting the antibody was sterically hindered from binding to the uncleaved fusion protein (FIG. 1B). While the IL-2/Mip1α fusion protein could be cleaved by PSA, it was found that after cleavage there was a slight decrease in the functional activity of IL-2, rather than the expected increase (FIGS. 1C and 1D). These data illustrated that the fusion protein containing both IL-2 and Mip1-α was expressed and could be cleaved by PSA. However, it also illustrated that inhibiting cytokine function in a predictable fashion using a steric hindrance approach was not straightforward. It was reasoned that if a molecule was constructed in which the putative inhibitory portion of the fusion protein bound the cytokine specifically, it would be more likely to inhibit its activity, yet increase cytokine function after cleavage. As described below, two distinct strategies were utilized to inhibit the biological activity of the cytokine. The first strategy employed a cytokine receptor, the second used an antibody fragment (scFv).

Example 2

Construction of IL-2/IL-2 Receptor Alpha (IL-2/IL-2Rα) Fusion Proteins

Figure 2A:
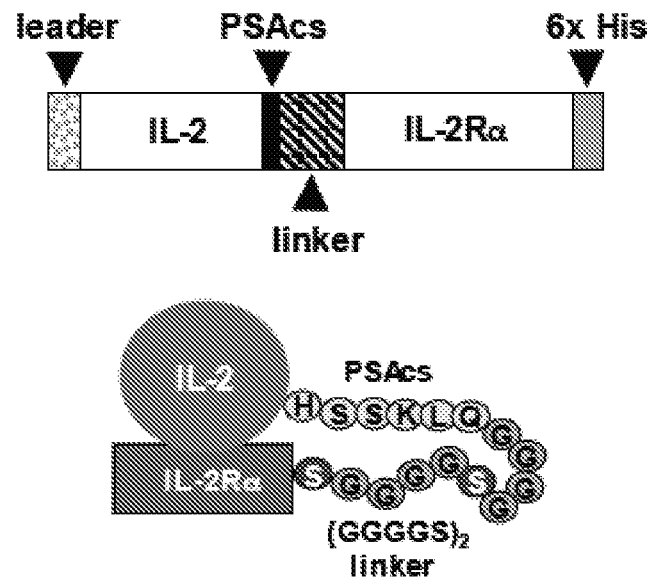
Figure 2B:
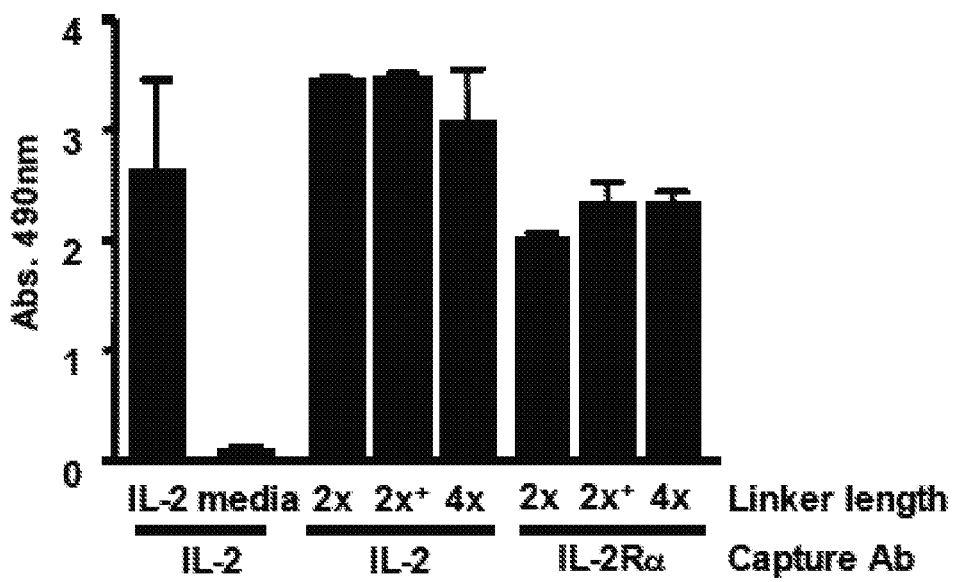
Figure 2C:
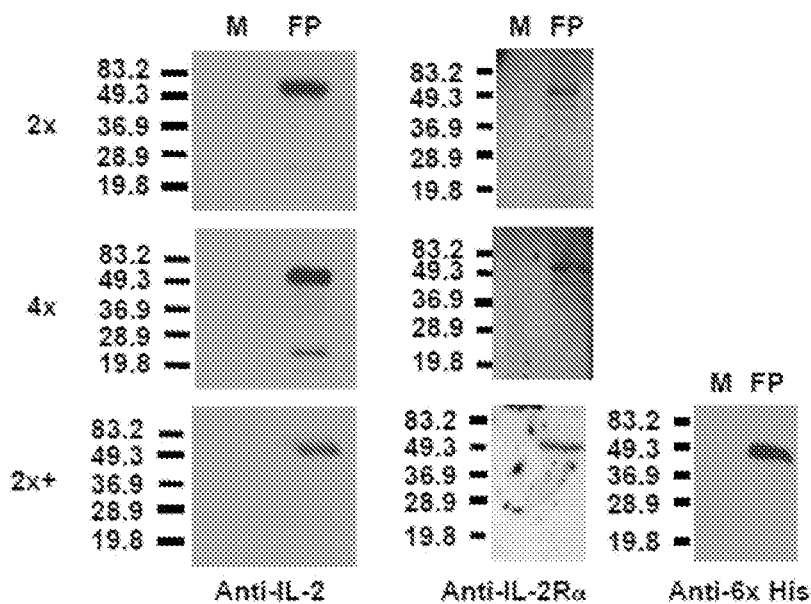

The first strategy using specific inhibition employed IL-2 and a portion of the IL-2 receptor is illustrated schematically in FIG. 2A. The mouse IL-2 cDNA was used as described above, and the alpha chain of the IL-2 receptor (IL-2Rα), which can bind IL-2 in the absence of the other subunits (β and γ) of the high affinity IL-2 receptor, was used as well (Minami et al., Ann. Rev. Immunol. 11:245-68 (1993)). In this construct, the transmembrane region of the IL-2Rα chain was removed, creating a soluble form of the receptor. To increase flexibility and allow the IL-2Rα portion of the molecule to fold back and inhibit IL-2, a repeating Gly-Ser linker consisting of $(GGGGS)_2$ (designated 2×) (SEQ ID NO:9), or $(GGGGS)_4$ (designated 4×) (SEQ ID NO:10) were introduced (Trinh et al., Mol. Immunol. 40:717-22 (2004)). In some cases, a 6× His tag was also added. These plasmids were used to construct recombinant baculoviruses to mediate expression in insect cells. As shown in FIG. 2B, the fusion proteins were examined with a capture ELISA using antibodies reactive with IL-2Rα and IL-2. These data show that the fusion proteins are produced, secreted, and contain both IL-2 and IL-2Rα on the same molecule. The immunoblot analysis in FIG. 2C reveals that the fusion protein is at the predicted apparent molecular weight of approximately 50 kDa and is reactive with anti-IL-2, IL-2Rα, and 6× His antibodies.

Example 3

PSA Cleavage of the IL-2/IL-2Rα Fusion Proteins Results in Increased Accessibility to Antibodies and Biologically Active IL-2

The IL-2/IL-2Rα fusion proteins were biochemically characterized before and after cleavage with the protease PSA.

Figure 3A:
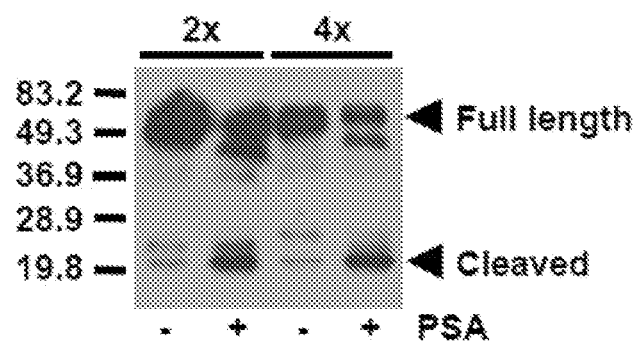
Figure 3B:
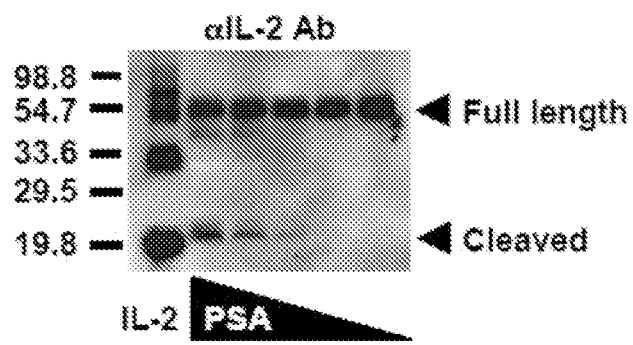
Figure 3C:
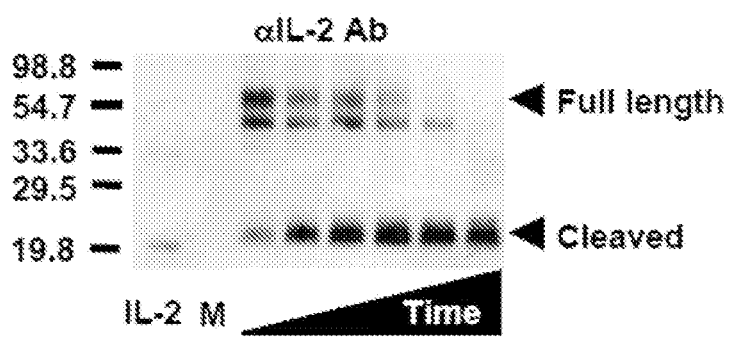
Figure 3D:
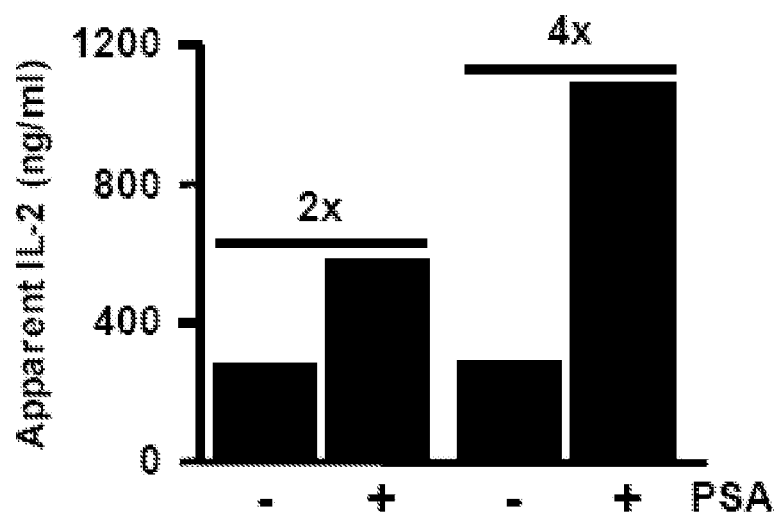
Figure 3E:
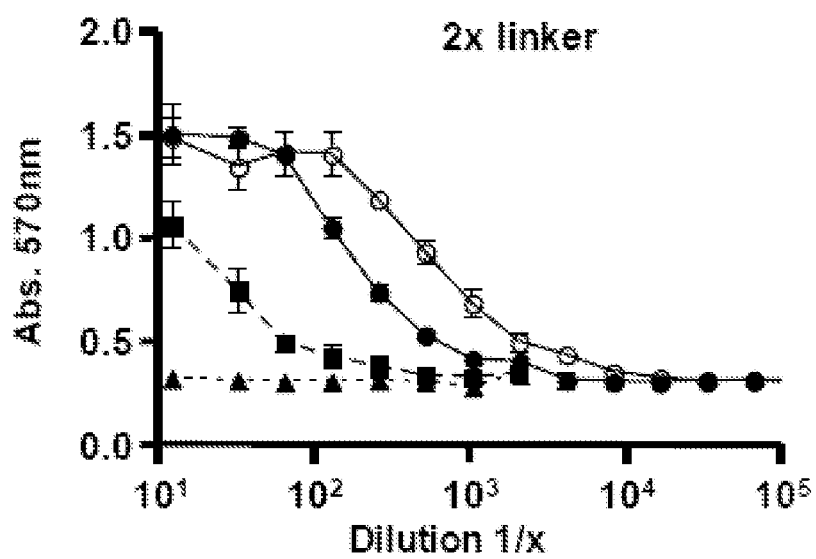
Figure 3F:
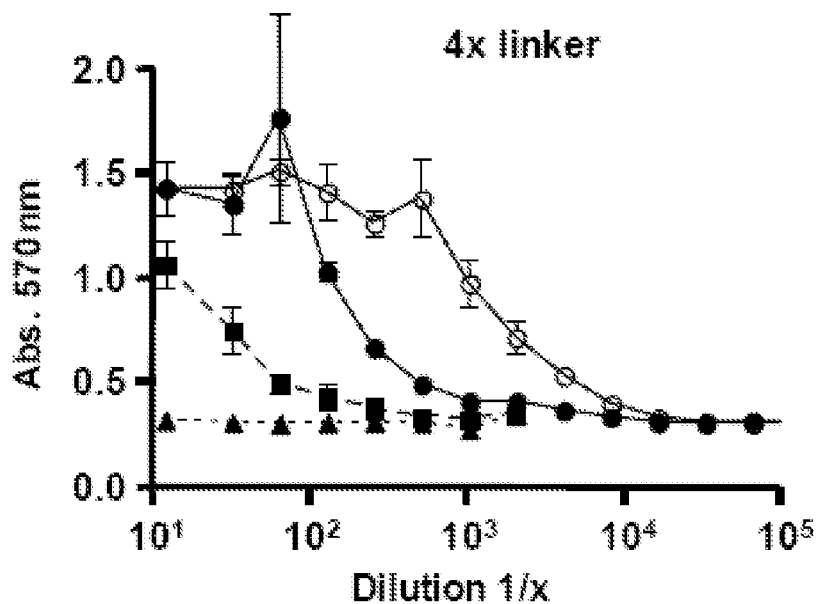

Immunoblot analyses revealed that the fusion proteins could be cleaved by PSA and that there was an increase in intensity of the predicted low molecular weight cleavage product of approximately 20 kDa reactive with an anti-IL-2 antibody after treatment of the samples with PSA (FIG. 3A). The degree of cleavage was dependent upon the amount of PSA as well as the time of incubation (FIGS. 3B and 3C). Interestingly, when the fusion protein was analyzed before and after PSA treatment by ELISA, it was found that the apparent amount of IL-2 was increased after PSA cleavage (FIG. 3D). In this experiment, there was an approximately 2 or 4-fold increase in the apparent amount of IL-2 detected using this sandwich ELISA depending on the construct, suggesting that the antibody binding was partially hindered in the intact fusion protein. Aliquots of the same samples shown in FIG. 3A were also analyzed after PSA treatment using the CTLL-2 cell line that requires IL-2 for growth and survival and the viability of cells can be ascertained using the colorimetric MTT assay. In this assay, the more a supernatant can be diluted the more biologically active IL-2 it contains, and as seen in FIGS. 3E and 3F there is an increase in the amount of biologically active IL-2 after PSA cleavage. The amount of IL-2 increased approximately 3.5-fold for the fusion protein with the 2× linker and 9-fold for the fusion protein with the 4× linker. Thus, the above data showed that after PSA cleavage there is an increase in the predicted low molecular weight cleavage fragment of approximately 20 kDa reactive with an anti-IL-2 antibody, an increase in antibody accessibility, and most importantly, an increase in the amount of biologically active IL-2. Because the 4× linker fusion protein had a larger increase in biologically active IL-2, this fusion protein was used in subsequent experiments.

Example 4

Prostate Explants or Extracts Expressing Human PSA can Cleave the IL-2/PSAcs/4× Linker/IL-2Rα Fusion Protein and Increase the Biological Activity of IL-2

To examine the cleavage of the fusion protein in the context of prostate tissue that expresses a complex mixture of proteases, transgenic (TG) mice that express human PSA in prostate explants were used (Wei et al., Proc. Natl. Acad. Sci. USA 94:6369-74 (1997)). Because conventional mice do not express PSA or any close homolog of human PSA, nontransgenic (NTG) mouse prostates served as a control for the expression of other proteases produced in the prostates that might cleave the fusion protein. The prostates were removed from TG and their NTG counterparts and placed into culture medium containing the IL-2/PSAcs/IL-2Rα fusion protein. At various times, aliquots were removed and analyzed biochemically and functionally. Supernatants from the explant cultures were analyzed for PSA expression using a specific PSA ELISA and it was shown that the media from explants from TG mice contained PSA whereas those from NTG mice did not (FIG. 4A). These same explant culture supernatants were also analyzed by immunoblot using the anti-IL-2 monoclonal antibody JES6-1A12 and by functional analysis using the IL-2-dependent cell line CTLL-2. In FIG. 4B, a lower apparent molecular weight band of approximately 20 kDa reactive with anti-IL-2 (cleaved) increased with time of culture in the TG explant cultures, but not in the NTG cultures. These data demonstrated other proteases that might be expressed by prostate cells did not cleave the IL-2/PSAcs/IL-2Rα fusion protein effectively but that human PSA derived from the prostate cells in the TG mouse could cleave the fusion protein. These same supernatants were also analyzed for functional IL-2 activity (FIG. 4C). The amount of biologically active IL-2 was approximately 8-fold higher in the TG explant cultures compared to the NTG cultures. This experiment has been repeated three times with the degree of enhancement of IL-2 activity ranging from 5 to 10-fold. As an additional, and perhaps more stringent test of specific cleavage of the fusion protein by PSA but not by other proteases found in the prostate, extracts of prostates from PSA TG and NTG mice were made, and the ability of these extracts to cleave the fusion protein in the absence of any protease inhibitors that might be found in fetal calf serum was examined. As shown in FIG. 4D, the TG prostate extracts contain large amounts of PSA in comparison to the NTG extracts. As can be seen in the immunoblot analysis in FIG. 4E, the extracts from the PSA TG mice effectively cleaved the fusion protein, whereas the NTG extracts did not. Importantly, there was an increase in the functional activity of the IL-2 assessed by the CTLL-2 assay after incubation with the PSA-containing TG extracts compared with the NTG extracts (FIG. 4F).

Example 5

Construction and Analysis of Human IL-2/PSAcs/Human scFv Fusion Proteins

A second strategy for specifically inhibiting a cytokine exploited a single chain Fv antibody fragment (scFv) to bind and inhibit IL-2. The constructs developed are outlined schematically in FIG. 5A. A scFv phage display library previously constructed using human VH and VL (Haidaris et al., J. Immunol. Methods 257:185-202 (2001); Malone and Sullivan, J. Mol. Recognit. 9:738-45 (1996)) was used. Since this phage display library expressed human scFv, it was used to identify phages (phscFv) that bound human IL-2 so that the components of the fusion protein constructed would all be derived from one species. From the small panel of phscFv that bound human IL-2 in a modified ELISA assay, a phage (scFv-2) whose binding to IL-2 could be inhibited by a neutralizing anti-IL-2 antibody (FIG. 5B) was chosen; the rationale for this choice was that the scFv-2 might also recognize a neutralizing epitope. The anti-IL-2 antibody blocked the binding of the scFv-2 phage by approximately 70%. As a control, it was found that this same anti-IL-2 neutralizing monoclonal antibody did not block the binding of another phscFv to its cognate antigen (designated SGPP), thereby illustrating that the antibody blocking observed was indeed specific for human IL-2 (FIG. 5B). The antibody variable regions of scFv-2 were sub-cloned and used to create the fusion proteins outlined in FIG. 5A which were then expressed in insect cells via recombinant baculoviruses. Analogous to the IL-2Rα chain constructs, the scFv-2 fusion proteins with 2× and 4× linker lengths were made. Since preliminary experiments suggested the fusion protein with the 2× and 4× linker length were similar in terms of their expression and their ability to be cleaved, for subsequent experiments the fusion protein containing the scFv-2 with the 2× linker length was used. As can be seen in FIG. 5C using the human IL-2/PSAcs/human scFv-2 with the 2× linker fusion protein, a lower molecular weight fragment of approximately 20 kDa reactive with an anti-IL-2 antibody resulted after cleavage with purified PSA.

The IL-2 dependent cell line CTLL-2 and the MTT assay to assess the biological effect of PSA cleavage on the same samples was also used. Samples were incubated with or without purified PSA and assessed for functional activity. The cleavage of the scFv-2 fusion protein with PSA resulted in an increase in bioactive IL-2 (FIG. 5D). The ability of this fusion protein to be cleaved in the context of other proteases that might be expressed by prostate cells was further investigated. Prostate extracts were made from normal NTG mice as well as from PSA-expressing TG mice as before. The immunoblot shown in FIG. 7A illustrates that the fusion protein containing the scFv-2 can be cleaved using prostate extracts from TG mice expressing PSA whereas NTG prostate extracts did not cleave the fusion protein. This cleavage results in an increase in the functional activity of IL-2 as determined with the CTLL-2 bioassay for IL-2 (FIG. 7B). This suggests that the PSA in the prostate was responsible for cleaving the fusion protein and that the other proteases expressed in the prostate were not. In summary, the human IL-2/PSAcs/human scFv-2 fusion protein can be cleaved by PSA and this cleavage results in increased biologically active IL-2.

Example 6

Alteration of the Protease Cleavage Site: Use of an MMP Cleavage Sequence

Whether this concept might be applied to other proteases was also investigated. For this purpose, an MMP cleavage site (SGESPAYYTA (SEQ ID NO:5)) that can be cleaved by several MMPs including MMP2 and MMP9 (Bremer et al., Nat. Med. 7:743-8 (2001)) was substituted in place of the PSA cleavage site used in the IL-2/PSAcs/IL-2Rα fusion protein. This construct encoding the MMP cleavage sequence was expressed using the baculovirus system in insect cells and the resulting fusion protein was tested for its ability to be cleaved using MMP9 and MMP2 and analyzed by immunoblot analyses. As can be seen in FIGS. 6A and 6C, the fusion protein can be cleaved by MMP2 or MMP9. After incubation with the proteases, a low apparent molecular weight product of approximately 20 kDa reactive with an anti-IL-2 antibody (JES6-1A12) was observed, consistent with the release of IL-2 from the fusion protein. FIGS. 6B and 6D compare the functional activity of the fusion protein before and after cleavage with MMP2 or MMP9 and illustrate that the functional level of IL-2 assessed by CTLL-2 is increased after cleavage. In another complementary experiment, the level of IL-2 activity of the intact fusion protein to a matched molar amount of free IL-2 was compared using the CTLL-2 bioassay. It was found that recombinant IL-2 exhibited 13.1±2.0 SD units/ng protein, whereas the fusion protein had only 0.198±0.2 SD units/ng protein (FIG. 6E). Thus, the level of IL-2 biologic activity is markedly attenuated (more than 60-fold) in the intact uncleaved fusion protein compared to the equivalent amount of free IL-2. Taken together, these data show that the specific inhibitory moiety can markedly inhibit the functional activity of the cytokine in the intact fusion protein, but the cytokine activity increases upon protease cleavage.

Additional MMP cleavage sites were also tested, which were selected from the group consisting of GPLGVRG (SEQ ID NO:2), IPVSLRSG (SEQ ID NO:3), or VPLSLYSG (SEQ ID NO:4). These cleavage sites were also capable of being cleaved using activated MMP2 and MMP9 (FIG. 10). Cleavage of the fusion proteins resulted in the release and activation of IL-2 (FIG. 11). These data illustrated that it is possible to change the protease cleavage site as a functional module.

Example 7

In Vivo Delivery of a Protease Activated Fusion Protein Results in Decreased Tumor Growth Next, the fusion protein was examined to determine if it could have biological effects in vivo. For these experiments, a system developed previously was used, in which tumor cells injected intraperitoneally rapidly and preferentially attach and grow initially on the milky spots, a series of organized immune aggregates found on the omentum (Gerber et al., Am. J. Pathol. 169:1739-52 (2006)). This system offers a convenient way to examine the effects of fusion protein treatment on tumor growth since fusion protein can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, was used (FIG. 8A). The omental tissue normally expresses a relatively small amount of MMP2 and MMP9, but, when Colon 38 tumor is present on the omentum, MMP levels increase (FIG. 8B). Using this tumor model, the ability of IL-2/MMPcs/IL-2Rα fusion proteins to affect tumor growth was examined. Colon 38 cells were injected intraperitoneally, allowed to attach and grow for 1 day, and then treated daily with fusion protein interaperitoneally. At day 7, the animals were sacrificed and the omenta examined for tumor growth using flow cytometry and by a colony-forming assay (FIGS. 8C, 8D, and 8E). FIG. 8C illustrates the gating scheme employed to analyze the tumor population present on the omentum by flow cytometry and panels I, II, and III represent plots of single mice from each of the three test groups studied. FIG. 8D illustrates the compiled flow cytometry data obtained from the individual mice.

It was found that treatment with the fusion protein can reduce tumor growth in vivo. In the mice that received tumor and fusion protein treatment (group I), there was a significant decrease (p<0.01) in the percentage of tumor cells detected on the omenta compared to the mice which were inoculated with a tumor but not treated with fusion protein (group II, FIG. 8D). There was a substantial fraction of cells in the tumor gate in mice that received tumor but were not treated with fusion protein (FIG. 8C, panel II) and a very low fraction of cells in the tumor gate of mice that did not receive the tumor (FIG. 8C, panel III). Very similar results were obtained when the presence of tumor cells were assessed using a colony-forming assay (Lord and Burkhardt, Cell Immunol. 85:340-50 (1984)) in which cells isolated from the omentum were tested for their ability to form colonies in vitro. These compiled data are shown in FIG. 8E. A significant difference was observed (p=0.0119) between the fusion protein treated mice and the vehicle treated mice in the number of viable tumor cells present on the omenta. Thus, in both the flow cytometry and the colony forming assays there was a clear decrease in the tumor burden with fusion protein treatment, although it should be noted that the decrease was not evident in all the treated animals. Taken together, these data illustrate that the fusion protein can affect tumor growth in vivo.

What is claimed is:

1. A method of treating a subject with a cancer, the method comprising:
   (a) selecting a subject with cancer; and
   (b) administering to the subject an effective amount of a chimeric polypeptide, wherein the chimeric polypeptide comprises (i) a first polypeptide comprising an interleukin-2 (IL-2) polypeptide or a fragment of an IL-2 polypeptide; (ii) a second polypeptide comprising a protease-cleavable sequence; and (ii) a third polypeptide comprising a blocking polypeptide, wherein the blocking polypeptide blocks the activity of the IL-2 polypeptide or fragment of the IL-2 polypeptide, wherein the protease cleavable sequence is cleaved by PSA or a matrix metalloproteinase (MMP), wherein the cancer is selected from the group consisting of prostate cancer, lung cancer, colon cancer, breast cancer and skin cancer and wherein the chimeric polypeptide is selected from the group consisting of SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; a chimeric polypeptide comprising SEQ ID NO: 45, wherein amino acids 154-171 of SEQ ID NO: 45 are replaced with amino acids 170-201 of SEQ ID NO: 38; and a chimeric polypeptide comprising SEQ ID NO: 48, wherein amino acids 154-176 of SEQ ID NO: 48 are replaced with amino acids 170-201 of SEQ ID NO: 38.

2. The method of claim 1, wherein the blocking polypeptide is an alpha chain of the IL-2 receptor (IL-2Rα).

3. The method of claim 1, wherein the chimeric polypeptide further comprises a histidine tag.

4. The method of claim 1, wherein the chimeric polypeptide comprises a linker sequence.

5. The method of claim 4, wherein the linker sequence is selected from the group consisting of GGGGS (SEQ ID NO:6), GSGSGS (SEQ ID NO:7), and G(SGGG)$_2$SGGT (SEQ ID NO:8).

6. The method of claim 1, wherein the MMP is matrix metalloproteinase 2 (MMP2) or matrix metalloproteinase 9 (MMP9).

* * * * *